US 7,999,741 B2

(12) United States Patent
Graves et al.

(10) Patent No.: US 7,999,741 B2
(45) Date of Patent: Aug. 16, 2011

(54) SYSTEMS AND METHODS FOR FACILITATING A FIRST RESPONSE MISSION AT AN INCIDENT SCENE USING PRECISION LOCATION

(75) Inventors: Alan Graves, Kanata (CA); Jeffrey Fitchett, Kanata (CA); Laurence Beaulieu, Kanata (CA); Brian Vezza, Allen, TX (US)

(73) Assignee: Avaya Inc., Basking Ridge, NJ (US)

( * ) Notice: Subject to any disclaimer, the term of this patent is extended or adjusted under 35 U.S.C. 154(b) by 451 days.

(21) Appl. No.: 12/213,675

(22) Filed: Jun. 23, 2008

(65) Prior Publication Data
US 2009/0140923 A1 Jun. 4, 2009

Related U.S. Application Data

(60) Provisional application No. 60/992,182, filed on Dec. 4, 2007.

(51) Int. Cl.
G01S 1/00 (2006.01)
(52) U.S. Cl. .................. 342/463; 342/457; 342/465
(58) Field of Classification Search .......... 342/463–465, 342/457
See application file for complete search history.

(56) References Cited

U.S. PATENT DOCUMENTS

| | | |
|---|---|---|
| 4,601,064 A | 7/1986 | Shipley |
| 5,291,399 A | 3/1994 | Chaco |
| 5,434,775 A | 7/1995 | Sims et al. |
| 5,465,082 A | 11/1995 | Chaco |
| 5,534,851 A | 7/1996 | Russek |
| 5,544,661 A | 8/1996 | Davis et al. |
| 5,594,786 A | 1/1997 | Chaco et al. |
| 5,610,596 A | 3/1997 | Petitclerc |
| 5,689,229 A | 11/1997 | Chaco et al. |
| 5,822,544 A | 10/1998 | Chaco et al. |
| 5,877,675 A | 3/1999 | Rebstock et al. |

(Continued)

FOREIGN PATENT DOCUMENTS

CA 2263428 A1 2/1998

(Continued)

OTHER PUBLICATIONS

Office Action mailed on May 16, 2008 in connection with U.S. Appl. No. 11/065,396.

(Continued)

*Primary Examiner* — Thomas H Tarcza
*Assistant Examiner* — Fred H Mull

(57) ABSTRACT

Systems and methods for facilitating a first response mission at an incident scene, such as an accident site, a natural or human-made disaster site, or any other first response site. One system is for locating a plurality of portable modules at an incident scene. The system comprises a plurality of receivers transportable to the incident scene. The system also comprises a processing entity configured to: determine a location of a first one of the portable modules based on first data derived from a wireless signal transmitted by the first one of the portable modules and received by at least three receivers of the plurality of receivers; and determine a location of a second one of the portable modules based on the location of the first one of the portable modules and second data derived from a wireless signal transmitted by the second one of the portable modules and received by the first one of the portable modules. For example, the system enables precision location of first responders, patients and equipment at the incident scene.

26 Claims, 18 Drawing Sheets

U.S. PATENT DOCUMENTS

| | | |
|---|---|---|
| 5,901,172 A | 5/1999 | Fontana et al. |
| 5,910,776 A | 6/1999 | Black |
| 5,911,687 A | 6/1999 | Sato et al. |
| 5,942,986 A | 8/1999 | Shabot et al. |
| 6,009,333 A | 12/1999 | Chaco |
| 6,026,125 A | 2/2000 | Larrick, Jr. et al. |
| 6,046,706 A * | 4/2000 | Vargas .................... 343/883 |
| 6,054,950 A | 4/2000 | Fontana |
| 6,211,790 B1 | 4/2001 | Radomsky et al. |
| 6,239,741 B1 | 5/2001 | Fontana et al. |
| 6,259,355 B1 | 7/2001 | Chaco et al. |
| 6,262,662 B1 | 7/2001 | Back et al. |
| RE37,531 E | 1/2002 | Chaco et al. |
| 6,344,794 B1 | 2/2002 | Ulrich et al. |
| 6,462,656 B2 | 10/2002 | Ulrich et al. |
| 6,539,393 B1 | 3/2003 | Kabala |
| 6,577,238 B1 | 6/2003 | Whitesmith et al. |
| 6,662,068 B1 | 12/2003 | Ghaffari |
| 6,690,741 B1 | 2/2004 | Larrick, Jr. et al. |
| 6,753,671 B1 | 6/2004 | Harvey |
| 6,773,396 B2 | 8/2004 | Flach et al. |
| 6,812,884 B2 | 11/2004 | Richley et al. |
| 6,823,199 B2 | 11/2004 | Gough |
| 6,825,763 B2 | 11/2004 | Ulrich et al. |
| 6,870,916 B2 | 3/2005 | Henrikson et al. |
| 6,876,303 B2 | 4/2005 | Reeder et al. |
| 6,958,677 B1 | 10/2005 | Carter |
| 6,958,706 B2 | 10/2005 | Chaco et al. |
| 6,972,683 B2 | 12/2005 | Lestienne et al. |
| 7,042,337 B2 | 5/2006 | Borders et al. |
| 7,080,061 B2 | 7/2006 | Kabala |
| 7,154,397 B2 | 12/2006 | Zerhusen et al. |
| 7,242,306 B2 | 7/2007 | Wildman et al. |
| 7,283,037 B2 | 10/2007 | Diorio et al. |
| 2001/0044731 A1 | 11/2001 | Coffman et al. |
| 2002/0044043 A1 | 4/2002 | Chaco et al. |
| 2002/0044059 A1 | 4/2002 | Reeder et al. |
| 2002/0147912 A1 | 10/2002 | Shmueli et al. |
| 2002/0183078 A1 | 12/2002 | Hase |
| 2002/0183979 A1 | 12/2002 | Wildman |
| 2003/0078810 A1 | 4/2003 | Cole et al. |
| 2003/0078811 A1 | 4/2003 | Cole et al. |
| 2003/0132845 A1 | 7/2003 | McDaniel, III |
| 2004/0001446 A1 | 1/2004 | Bhatia et al. |
| 2004/0004460 A1 | 1/2004 | Fitch et al. |
| 2004/0008114 A1 | 1/2004 | Sawyer |
| 2004/0034284 A1 | 2/2004 | Aversano et al. |
| 2004/0078219 A1 | 4/2004 | Kaylor et al. |
| 2004/0100376 A1 | 5/2004 | Lye et al. |
| 2004/0108954 A1 | 6/2004 | Richley et al. |
| 2004/0153344 A1 | 8/2004 | Bui et al. |
| 2004/0178947 A1 | 9/2004 | Richley et al. |
| 2004/0186357 A1 | 9/2004 | Soderberg et al. |
| 2004/0193449 A1 | 9/2004 | Wildman et al. |
| 2004/0252015 A1 | 12/2004 | Galperin et al. |
| 2004/0257224 A1 | 12/2004 | Sajkowsky |
| 2005/0017864 A1 | 1/2005 | Tsoukalis |
| 2005/0024269 A1 * | 2/2005 | Kotzin et al. ................ 343/702 |
| 2005/0027465 A1 | 2/2005 | Pozsgay et al. |
| 2005/0035862 A1 | 2/2005 | Wildman et al. |
| 2005/0148831 A1 | 7/2005 | Shibata et al. |
| 2005/0151641 A1 | 7/2005 | Ulrich et al. |
| 2005/0153681 A1 | 7/2005 | Hanson |
| 2005/0168341 A1 | 8/2005 | Reeder et al. |
| 2005/0188095 A1 | 8/2005 | Gardiner et al. |
| 2005/0201345 A1 | 9/2005 | Williamson |
| 2005/0228613 A1 * | 10/2005 | Fullerton et al. .............. 342/463 |
| 2005/0283382 A1 | 12/2005 | Donoghue et al. |
| 2006/0006999 A1 | 1/2006 | Walczyk et al. |
| 2006/0143043 A1 | 6/2006 | McCallie, Jr. et al. |
| 2006/0282459 A1 | 12/2006 | Kabala |

FOREIGN PATENT DOCUMENTS

| | | |
|---|---|---|
| CA | 2362635 A1 | 8/2000 |
| CA | 2373241 A1 | 11/2000 |
| CA | 2434714 A1 | 8/2002 |
| EP | 0 369 662 A2 | 5/1990 |
| EP | 1 101 437 A1 | 5/2001 |
| EP | 1 156 336 A1 | 11/2001 |
| EP | 0 973 316 A3 | 6/2002 |
| EP | 1 536 306 A1 | 6/2005 |
| GB | 2320397 A | 6/1998 |
| GB | 2355889 A | 5/2001 |
| JP | 2002157040 A | 5/2002 |
| JP | 2003189359 A | 7/2003 |
| WO | WO 95/01617 | 1/1995 |
| WO | WO 99/04685 | 2/1999 |
| WO | WO 99/64974 A1 | 12/1999 |
| WO | WO 00/52498 | 9/2000 |
| WO | WO 2004/032019 A3 | 4/2004 |
| WO | WO 2004/042563 A3 | 5/2004 |
| WO | WO 2004/102457 A2 | 11/2004 |
| WO | WO 2005/043402 A1 | 5/2005 |
| WO | PCT/CA2006/000203 | 1/2006 |
| WO | PCT/CA2006/000204 | 2/2006 |
| WO | PCT/CA2006/000195 | 5/2006 |
| WO | PCT/CA2006/000196 | 5/2006 |
| WO | PCT/CA2006/000197 | 5/2006 |
| WO | PCT/CA2006/000205 | 5/2006 |
| WO | WO 2006/049728 A1 | 5/2006 |
| WO | PCT/CA2006/000198 | 6/2006 |
| WO | PCT/CA2006/001479 | 12/2006 |

OTHER PUBLICATIONS

Jonathan Collins, "RFID Remedy for Medical Errors", RFID Journal, http://www.rfidjournal.com/article/view/961, May 28, 2004, 3 pages.

Claire Swedberg, "Ford Deploys RFID-Enabled Chargers", RFID Journal, http://www.rfidjournal.com/article/articleview/1348/1/1/, Jan. 19, 2005, 3 pages.

Parco Merged Media Corporation, "The Parco Real Time Location System", http://www.parcomergedmedia.com/whcs_pgis.html, downloaded Feb. 2005, 5 pages.

Parco Merged Media Corporation, "Improving the Availability of Information", www.parcowireless.com, downloaded Jan. 2005, 8 pages.

Parco Merged Media Corporation, "The Parco Wireless Health Care System (WHCS)", www.parcowireless.com, downloaded Aug. 2004, 8 pages.

Robert J. Fontana, Ph.D., "Experimental results from an ultra wideband precision geolocation system", www.multispectral.com, downloaded Aug. 2004, 9 pages.

Robert J. Fontana et al., "Ultra-wideband precision asset location system", www.multispectral.com, downloaded Aug. 2004, 5 pages.

Robert J. Fontana et al., "Commercialization of an ultra wideband precision asset location system", www.multispectral.com, downloaded Aug. 2004, 5 pages.

Dr. Zeev Weissman, "Indoor Location", Tadlys Ltd., www.tadlys.com, downloaded Jul. 2004, 15 pages.

Chronaki et al, "WebOnCOLL: Medical Collaboration in Regional Healthcare Netwoks", IEEE Transactions on Information Technology in Biomedicine, vol. 1, No. 4, Dec. 1997, pp. 257-269.

Rodriquez et al., "Location-Aware Access to Hospital Information and Services", IEEE Transactions on Information Technology in Biomedicine, vol. 8, No. 4, Dec. 2004, pp. 448-455.

The OODA "Loop" Sketch, downloaded from http://www.d-n-i.net/boyd_ooda_loop.ppt, © Kettle Creek Corporation, Mar. 13, 2008, downloaded on Sep. 18, 2008.

Laxmisan et al, The multitasking clinician: Decision-making and cognitive demand during and after team handoffs in emergency care, Int'l J of Med Info 76, Sep. 27, 2006, pp. 801-811.

EHRS Blueprint—an interoperable EHR framework—Infoway Architecture Update—Canada Health infoway, Mar. 2006, Solution Architecture Group, 136 pages.

Graves, Alan et al., Applications and Solutions for Healthcare-Hospitals, A Perspective on ECAS, Version 1.0, Dec. 20, 2006, © Nortel Networks 2006, 226 pages.

Project MESA: An Update, Making Progress Toward an International PPDR Standard, IEEE Personal, Indoor, and Mobile Radio Conference, Beijing, China, Sep. 2003, 7 pages.

* cited by examiner

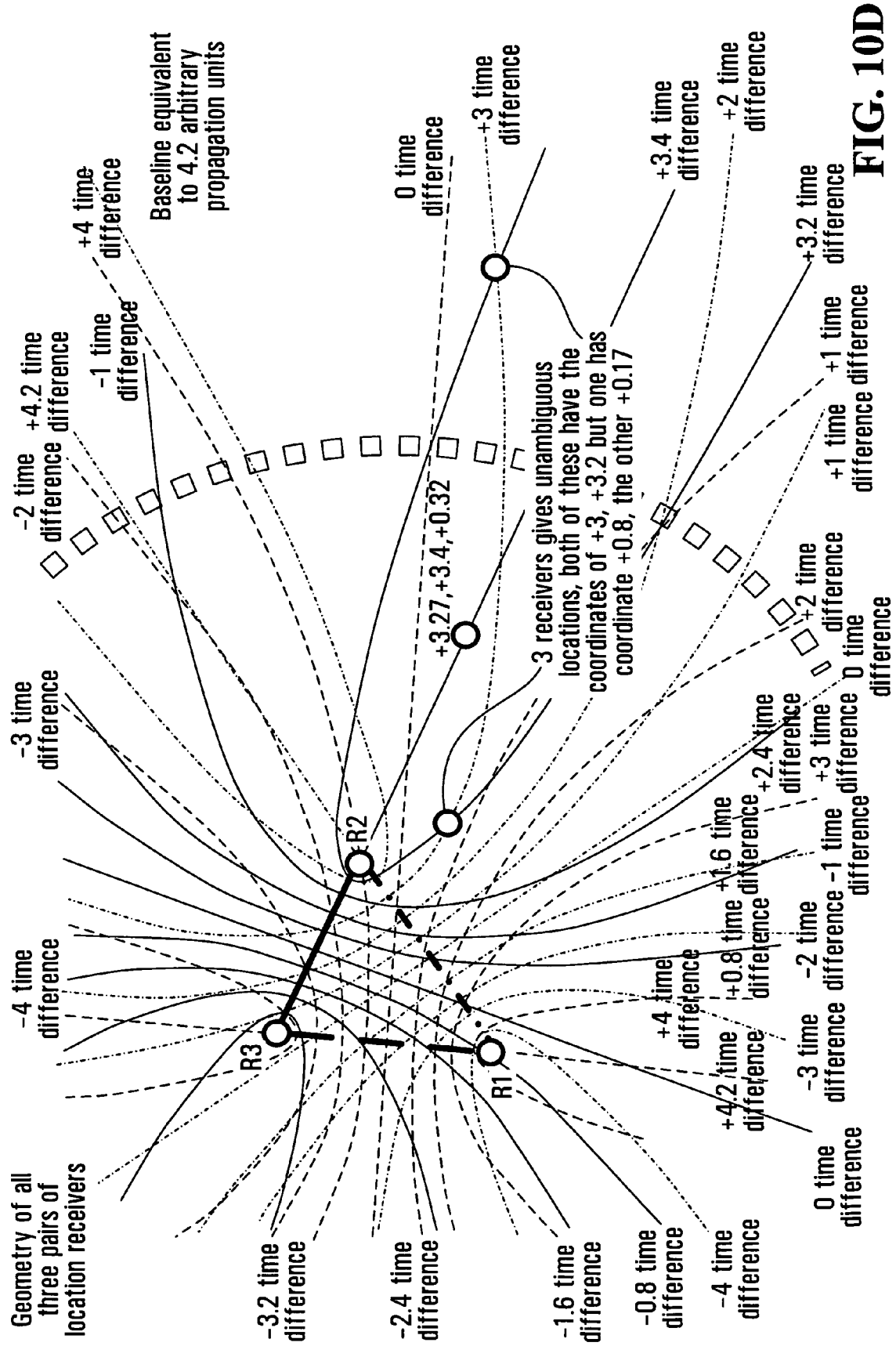

SYSTEMS AND METHODS FOR FACILITATING A FIRST RESPONSE MISSION AT AN INCIDENT SCENE USING PRECISION LOCATION

CROSS-REFERENCE TO RELATED APPLICATION

This application claims the benefit under 35 U.S.C. §119(e) of U.S. Provisional Patent Application No. 60/992,182 filed on Dec. 4, 2007 by Graves et al. and hereby incorporated by reference herein.

FIELD OF THE INVENTION

The invention relates generally to first response services and, more particularly, to systems and methods for facilitating a first response mission at an incident scene.

BACKGROUND

First responders such as emergency medical service (EMS) workers, police officers or firefighters deployed at an incident scene have limited connectivity to hospitals and other places remote from the incident scene. In particular, first responders have limited connectivity to the emergency room (ER) of the hospital to which they are delivering and do not know the status of the ER, nor does the ER know their status. Adding to this the fact that only limited medical information, if any, can be passed backward and forward between the first responders and the hospital, the ER treatment typically starts with a patient assessment when the emergency vehicle arrives at the hospital, instead of being a continuous process from the moment when the first responders arrive at the incident scene.

Furthermore, the incident scene may encompass multiple casualties who have to be triaged and stabilized on-site if their number threatens to overwhelm the first responders. Those who are beyond hope and those who will survive without treatment take backstage to those where treatment makes a difference for survival.

In addition, the incident scene itself may be hazardous, both to the casualties and to the first responders. Unknown or undetected conditions or changes therein at the incident scene may present serious risks for both the casualties and the first responders.

While certain technologies have been developed to assist first responders, they are unsatisfactory in many respects. For example, existing technologies are typically point solutions and lack in terms of an integrated approach which takes into account information from a variety of sources. Also, existing technologies tend to not be rapidly deployable (i.e., seconds, not minutes or hours) and are thus often of limited effectiveness where time is crucial. Furthermore, while it may often be useful to know where the first responders and/or the casualties are located, existing technologies may only provide inadequate or insufficient precision in locating them (e.g., civilian grade global positioning system (GPS) technology typically offers accuracies of about 9 to 15 meters (30 to 50 feet)., due to the user equivalent range errors (UEREs) of ionospheric effects, ephemeris errors, satellite clock errors, multipath distortion, and tropospheric effects).

Accordingly, there is a need for solutions facilitating a first response mission at an incident scene, and particularly for solutions providing first responders with bidirectional communication capability, real-time support for their information needs, and knowledge about their environment as they stabilize and transport patients under what may be hazardous conditions, solutions enabling the patients to be monitored, and solutions enabling precise location of the first responders and patients at the incident scene.

SUMMARY OF THE INVENTION

According to a first broad aspect, the invention provides a method for locating a plurality of portable modules at an incident scene. The method comprises: receiving first data derived from a wireless signal transmitted by a first one of the portable modules and received by at least three receivers of a plurality of receivers transported to the incident scene; determining a location of the first one of the portable modules based on the first data; receiving second data derived from a wireless signal transmitted by a second one of the portable modules and received by the first one of the portable modules; and determining a location of the second one of the portable modules based on the second data and the location of the first one of the portable modules.

According to a second broad aspect, the invention provides a system for locating a plurality of portable modules at an incident scene. The system comprises a plurality of receivers transportable to the incident scene. The system also comprises a processing entity configured to: determine a location of a first one of the portable modules based on first data derived from a wireless signal transmitted by the first one of the portable modules and received by at least three receivers of the plurality of receivers; and determine a location of a second one of the portable modules based on the location of the first one of the portable modules and second data derived from a wireless signal transmitted by the second one of the portable modules and received by the first one of the portable modules.

According to a third broad aspect, the invention provides computer-readable media containing computer-readable program code executable by a computing apparatus to implement a process for locating a plurality of portable modules at an incident scene. The computer-readable program code comprises: first program code for causing the computing apparatus to be attentive to receipt of first data derived from a wireless signal transmitted by a first one of the portable modules and received by at least three receivers of a plurality of receivers transported to the incident scene; second program code for causing the computing apparatus to determine a location of the first one of the portable modules based on the first data; third program code for causing the computing apparatus to be attentive to receipt of second data derived from a wireless signal transmitted by a second one of the portable modules and received by the first one of the portable modules; and fourth program code for causing the computing apparatus to determine a location of the second one of the portable modules based on the second data and the location of the first one of the portable modules.

These and other aspects of the invention will now become apparent to those of ordinary skill in the art upon review of the following description of embodiments of the invention in conjunction with the accompanying drawings.

BRIEF DESCRIPTION OF THE DRAWINGS

A detailed description of embodiments of the invention is provided below, by way of example only, with reference to the accompanying drawings, in which:

FIGS. 10A to 10D show an example of a geometry associated with a location determination process based on a differential time of arrival solution.

It is to be expressly understood that the description and drawings are only for the purpose of illustrating certain embodiments of the invention and are an aid for understanding. They are not intended to be a definition of the limits of the invention.

DETAILED DESCRIPTION OF EMBODIMENTS

Figure 1:
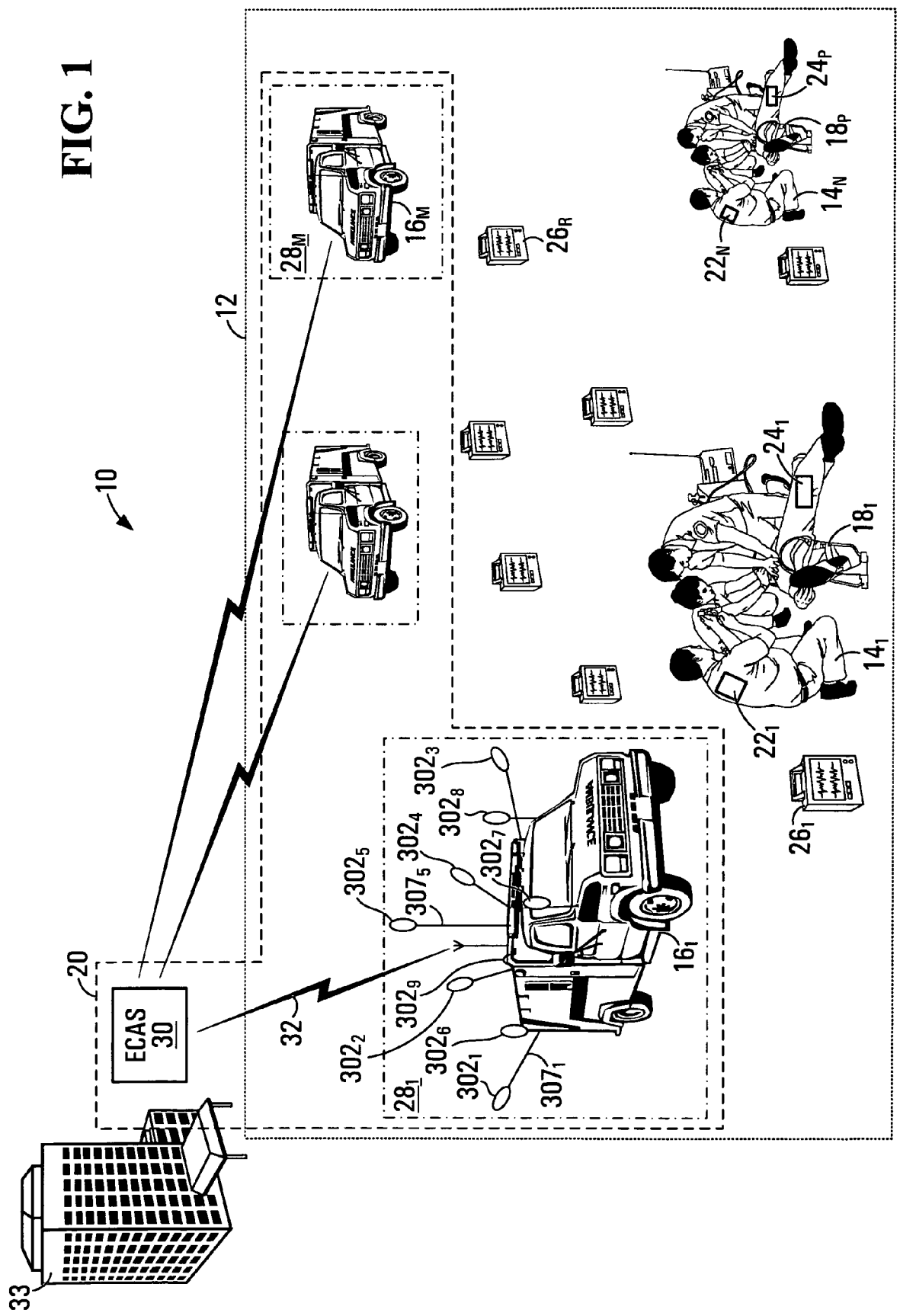
FIG. 1 shows a first response support system for facilitating a first response mission at an incident scene, in accordance with an embodiment of the invention.

FIG. 1 shows a first response support system 10 for facilitating a first response mission at an incident scene 12 (e.g., an accident site, a natural or human-made disaster site, or any other first response site), in accordance with an embodiment of the invention. In this case, the first response mission involves a plurality of first responders $14_1 \ldots 14_N$ arriving at the incident scene 12 via a plurality of first response vehicles $16_1 \ldots 16_M$ to perform various tasks at the incident scene 12, including providing first response aid to a plurality of patients $18_1 \ldots 18_P$ at the incident scene 12, potentially prior to transporting some or all of them to a healthcare facility 33, which may be a hospital or other healthcare establishment. Each of the patients $18_1 \ldots 18_P$ is an individual casualty at the incident scene 12 awaiting or receiving care and treatment, such as medical care and treatment, from one or more of the first responders $14_1 \ldots 14_N$ and/or awaiting transportation or being transported to the healthcare facility 33 or another healthcare facility. In this example, the first responders $14_1 \ldots 14_N$ are emergency medical service (EMS) workers (e.g., paramedics) and the first response vehicles $16_1 \ldots 16_M$ are ambulances, whereas in other examples the first responders $14_1 \ldots 14_N$ may include police officers, firefighters or other types of first responders and the first response vehicles $16_1 \ldots 16_M$ may include police vehicles, firefighter trucks or other types of emergency vehicles.

The first response support system 10 comprises a plurality of "packs" carried by the first responders $14_1 \ldots 14_N$ when arriving at the incident scene 12. Each of these packs is a portable electronic module that is embodied as a single portable device or combination of portable devices carried by a given one of the first responders $14_1 \ldots 14_N$ at the incident scene 12 (e.g., manually carried and/or worn by that first responder). More particularly, in this embodiment, these packs include a plurality of first responder packs $22_1 \ldots 22_N$ each personally kept by a respective one of the first responders $14_1 \ldots 14_N$ at the incident scene 12, a plurality of patient packs $24_1 \ldots 24_P$ each personally associated with a respective one of the patients $18_1 \ldots 18_P$, and a plurality of drop packs $26_1 \ldots 26_R$ which can be placed by the first responders $14_1 \ldots 14_N$ at various locations at the incident scene 12.

As further discussed later on, the packs $22_1 \ldots 22_N$, $24_1 \ldots 24_P$, $26_1 \ldots 26_R$ are configured to transmit wireless signals from which can be derived various data regarding the incident scene 12, such as: location data indicative of a location of each of the first responders $14_1 \ldots 14_N$, the patients $18_1 \ldots 18_P$ and the drop packs $26_1 \ldots 26_R$ at the incident scene 12; physical data indicative of physical parameters (e.g., surrounding temperature, pressure, vibrations, chemical concentrations, radiation levels, etc.) sensed by these packs; physiological data indicative of physiological parameters (e.g., vital signs such as heart rate, blood pressure, body temperature, oxygenation level, breathing rate; toxin levels; etc.) of the patients $18_1 \ldots 18_P$; data derived from input made by the first responders $14_1 \ldots 14_N$ using their first responder packs $22_1 \ldots 22_N$; etc.

The first responder packs $22_1 \ldots 22_N$ also enable the first responders $14_1 \ldots 14_N$ to wirelessly communicate with one another and/or with remote clinicians (e.g., physicians, radiologists, pharmacists, interns, nurses, laboratory technicians or other individuals whose duties relate to patient diagnosis and/or treatment) and to wirelessly receive information relevant to their tasks (e.g., information regarding actions to be performed, such as administering certain medical treatment to one or more of the patients $18_1 \ldots 18_P$, transporting one or more of the patients $18_1 \ldots 18_P$ to a given healthcare facility, moving himself/herself or one or more of the patients $18_1 \ldots 18_P$ to a different location, etc.).

In addition, the first response support system 10 comprises a processing system 20 to receive and process the wireless signals transmitted by the packs $22_1 \ldots 22_N$, $24_1 \ldots 24_P$, $26_1 \ldots 26_R$ in order to determine actions to be taken with respect to the first response mission for optimizing communications involving the first responders $14_1 \ldots 14_N$ and increasing first responder effectiveness, quality of care to patients, patient/first responder safety, speed of processing and overall first response site safety. Examples of such actions include: administration of certain medical treatment to one or more of the patients $18_1 \ldots 18_P$; movement of one or more of the patients $18_1 \ldots 18_P$ and/or the first responders $14_1 \ldots 14_N$; communication of one or more of the first responders $14_1 \ldots 14_N$ with one or more doctors, nurses or other clinicians remote from the incident scene 12; transportation of one or more of the patients $18_1 \ldots 18_P$ to one or more healthcare facilities (e.g., transportation of different ones of the patients $18_1 \ldots 18_P$ to different healthcare facilities for load sharing between the different healthcare facilities); preparation of resources (e.g., equipment and clinicians) at one or more healthcare facilities for arrival of one or more of the patients $18_1 \ldots 18_P$; etc.

More particularly, in this embodiment, the processing system 20 comprises a remote processing subsystem 30 located remotely from the incident scene 12 and a plurality of local processing stations $28_1 \ldots 28_M$ transported to the incident scene 12 by respective ones of the first response vehicles $16_1 \ldots 16_M$. In this example, the remote processing subsystem 30 is located at a healthcare facility 33, which may be a hospital or other healthcare establishment. Each of the local processing stations $28_1 \ldots 28_M$ can communicate with the remote processing subsystem 30 via a wireless communication link 32, which may be established over an emergency services network and/or a communications provider network (e.g., a cellular, WiMax or other public or dedicated emergency services wireless network).

As further described later, in this embodiment, the remote processing subsystem 30 implements, and will hereinafter be referred to as, an "environment- and context-aware system" (ECAS) configured to determine which actions should be taken with respect to the first response mission when certain "situations" are deemed to occur, based on data derived from wireless signals transmitted by the packs $22_1 \ldots 22_N$, $24_1 \ldots 24_P$, $26_1 \ldots 26_R$ at the incident scene 12. The ECAS 30 can be viewed as a smart (e.g., artificially intelligent) communication and information handling system which operates to achieve specific objectives set by applicable policies or guidelines/targets that it invokes on a basis of its deducing situations deemed to occur from its environmental and other contextual information sources and deductions. In regards to the first response mission considered in this example, the policies or guidelines/targets address optimization of communications involving the first responders $14_1 \ldots 14_N$ and increasing first responder effectiveness, quality of care to patients, patient/first responder safety, speed of processing and overall first response site safety.

For their part, the local processing stations $28_1 \ldots 28_M$ are transported to the incident scene 12 by respective ones of the first response vehicles $16_1 \ldots 16_M$ and provide communication, data processing and other functionality between the packs $22_1 \ldots 22_N$, $24_1 \ldots 24_P$, $26_1 \ldots 26_R$ and the ECAS 30 (and other resources within the healthcare facility 33). In that sense, the local processing stations $28_1 \ldots 28_M$ will be referred to as "ECAS outstations".

Generally speaking, the packs $22_1 \ldots 22_N$, $24_1 \ldots 24_P$, $26_1 \ldots 26_R$, the ECAS outstations $28_1 \ldots 28_M$ and the ECAS 30 can cooperate to provide information, communication and protective (against hazardous conditions) support to the first responder vehicles $16_1 \ldots 16_M$, the first responders $14_1 \ldots 14_N$ and the patients $18_1 \ldots 18_P$ at the incident scene 12 during first triage and treatment, stabilization and preparation for transport to bring the patients $18_1 \ldots 18_P$ into a clinical treatment system which, in this example, is centered at the healthcare facility 33 (and possibly one or more other healthcare facilities as may be involved).

The ECAS outstations $28_1 \ldots 28_M$ transported to the incident scene 12 and the packs $22_1 \ldots 22_N$, $24_1 \ldots 24_P$, $26_1 \ldots 26_R$ deployed by the first responders $14_1 \ldots 14_N$ at the incident scene 12 enable capabilities of the ECAS 30 to be extended into a first response area at the incident scene 12. For example, some of the capabilities of the ECAS 30 that may be extended into the first response area include:

i. Precision location (absolute location or relative location/proximity) for the first response vehicles $16_1 \ldots 16_M$, the first responders $14_1 \ldots 14_N$ and the patients $18_1 \ldots 18_P$ at the incident scene 12;

ii. Automated monitoring of environmental conditions across the incident scene 12 for purposes of detecting inclement, adverse or potentially hazardous situations;

iii. An ability for the first responders $14_1 \ldots 14_N$ to be clinically integrated into workflows and resources of the healthcare facility 33, particularly its emergency room (ER), during the stabilization and preparation for transport of the patients $18_1 \ldots 18_P$ so that the healthcare facility's staff and clinical resources and databases to which the ECAS 30 has access can provide support as needed to the first responders $14_1 \ldots 14_N$ and so that the healthcare facility 33 can be provided with advance information on conditions of incoming ones of the patients $18_1 \ldots 18_P$;

iv. An ability for the ECAS 30 and/or remote clinicians to remotely track the locations of the patients $18_1 \ldots 18_P$ and monitor the patients $18_1 \ldots 18_P$ (including unattended ones) for key medical data and life sign characteristics; and v. Automatic association of the first responders $14_1 \ldots 14_N$ with different ones of the patients $18_1 \ldots 18_P$ that they are treating or responsible for.

These and other capabilities of the ECAS 30 which can be extended into the first response area at the incident scene 12 can enhance the effectiveness, productivity and/or safety of the first responders $14_1 \ldots 14_N$ and the quality of care, speed of response and care, and/or safety of the patients $18_1 \ldots 18_P$.

The aforementioned components of the first response support system 10 will now be discussed in more detail.

Packs $22_1 \ldots 24_N$, $24_1 \ldots 24_P$, $26_1 \ldots 26_R$

The packs $22_1 \ldots 22_N$, $24_1 \ldots 24_P$, $26_1 \ldots 26_R$ communicate with the ECAS outstations $28_1 \ldots 28_M$ and the ECAS 30 of the processing system 20 to perform various functions, including: providing an accurate precision location capability across the incident scene 12, which allows the first responders $14_1 \ldots 14_N$ and the patients $18_1 \ldots 18_P$ to be tracked and associations to be established therebetween; providing location-aware sensor information about environmental conditions at the incident scene 12, which allows hazardous or adverse conditions to be detected; and facilitating communications, including communication between the first responders $14_1 \ldots 14_N$ and remote clinicians at the healthcare facility 33 as well as access to clinical information (which may be suitably profiled for first response use) from an institutional information system of the healthcare facility 33.

a) First Responder Packs $22_1 \ldots 22_N$

Figure 2:
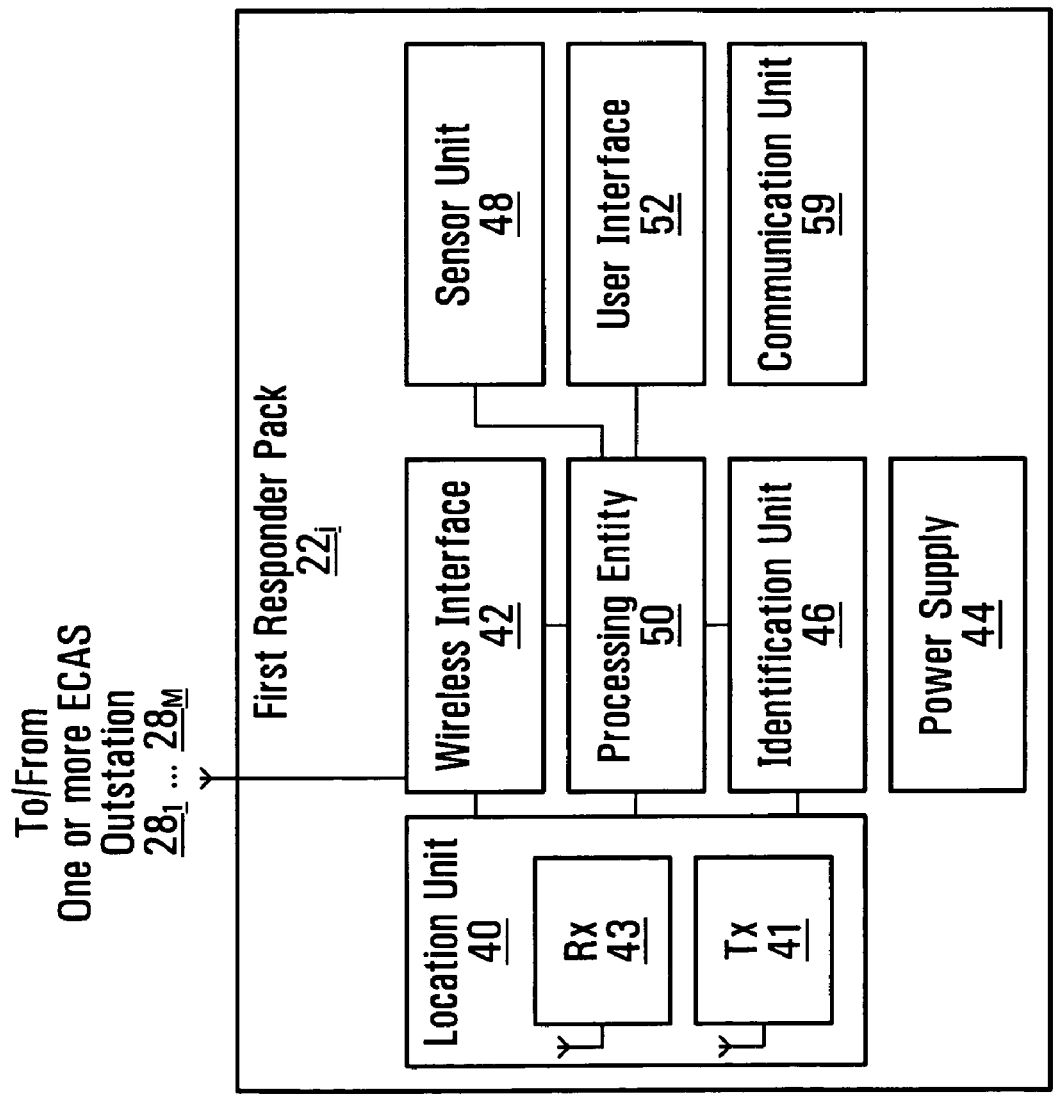
FIG. 2 shows a first responder pack of the first response support system, in accordance with an embodiment of the invention.

FIG. 2 shows an embodiment of a first responder pack $22_j$ of the first responder packs $22_1 \ldots 22_N$ that is kept by a first responder $14_j$ of the first responders $14_1 \ldots 14_N$ at the incident scene 12. Other ones of the first responder packs $22_1 \ldots 22_N$ may be similarly constructed.

The first responder pack $22_j$ comprises suitable hardware and software (which may include firmware) for implementing a plurality of functional components, including, in this embodiment, a location unit 40, an identification unit 46, a sensor unit 48, a wireless interface 42, a user interface 52, a communication unit 59, a processing entity 50 and a power supply 44. These functional components may be embodied as a single portable device or combination of portable devices carried by the first responder $14_j$. For example, the single portable device or combination of portable devices constituting the first responder pack $22_j$ may be manually carried by the first responder $14_j$ and/or worn by the first responder $14_j$ (e.g., strapped or otherwise attached on the first responder $14_j$ or integrated with his/her clothing). The first responder pack $22_j$ may be assigned to or associated with the first responder $14_j$ before or upon arrival at the incident scene 12 by various means (e.g., by entering an identity of the first responder $14_j$ and/or a password confirming this identity and/or by biometric association).

The location unit 40 enables the processing system 20 to determine a location of the first responder $14_j$. To that end, the location unit 40 comprises a location transmitter (e.g., a location pinger) 41 to transmit a wireless location signal that allows the processing system 20 to determine the location of the first responder pack $22_j$ and, thus, of the first responder $14_j$. For example, the wireless location signal may be a short (e.g., nanosecond scale) radio frequency (RF) burst or series of short RF bursts. The processing system 20 can determine the location of the first responder $14_j$ based on data derived from the wireless location signal, i.e., data conveyed by that signal and/or data generated upon reception of that signal such as data related to a time of arrival of that signal at a receiver having a known location. More particularly, in this embodiment, the processing system 20 determines the location of the first responder $14_j$ based on three or more times of arrival of the wireless location signal at three or more location receivers (described later on) having known locations that are distributed among some of the ECAS outstations $28_1 \ldots 28_M$ and/or other ones of the packs $22_1 \ldots 22_N$, $26_1 \ldots 26_R$, $24_1 \ldots 24_P$. For instance, the processing system 20 may apply triangulation techniques (e.g., multilateration or trilateration) to determine the location of the first responder $14_j$ based on the times of arrival of the wireless location signal at these three of more location receivers. Such triangulation techniques, which can be based on times of arrival either explicitly (i.e., on the times of arrival themselves) or implicitly (i.e., on differences between the times of arrival), are well known and need not be described here. In other embodiments, rather than allow the processing system 20 to effect location computations based on times of arrival of the wireless location signal transmitted by the location transmitter 41, the wireless location signal may convey other location data that indicates or can be used to compute the location of the first responder $14_j$.

In addition, in this embodiment, once the first responder pack $22_j$ has been located, the location unit 40 enables the processing system 20 to determine locations of other ones of the packs $22_1 \ldots 22_N$, $26_1 \ldots 26_R$, $24_1 \ldots 24_P$ that are within range of the first responder pack $22_j$. To that end, the location unit 40 comprises a location receiver (e.g., a location sensor) 43 to receive wireless location signals from location transmitters of other ones of the packs $22_1 \ldots 22_N$, $26_1 \ldots 26_R$, $24_1 \ldots 24_P$ that are within range of the first responder pack $22_j$. As further discussed later on, once it has been located by the processing system 20, the first responder pack $22_j$ may transmit a wireless signal to the processing system 20 on a basis of the wireless locations signals it receives from these location transmitters in order to allow the processing system 20 to determine locations of those packs $22_1 \ldots 22_N$, $26_1 \ldots 26_R$, $24_1 \ldots 24_P$ from which the first responder pack $22_j$ received the wireless location signals.

Generally speaking, in this embodiment, and in accordance with a "cascaded location process" that is further discussed later on, the locations of the packs $22_1 \ldots 22_N$, $26_1 \ldots 26_R$, $24_1 \ldots 24_P$ are determined in multiple stages by the processing system 20, whereby those packs whose locations are known are used to receive wireless location signals from other packs whose locations are unknown and transmit wireless signals to the processing system 20 on a basis of the wireless location signals that they receive in order to enable the locations of these other packs to be determined. This is particularly useful in that it allows the first response support system 10 to extend its location-awareness across the incident scene 12 by using packs which have been located in order to locate further packs that may be beyond the range of location receivers of the ECAS outstations $28_1 \ldots 28_M$.

In order for the cascaded location process to precisely locate the packs $22_1 \ldots 22_N$, $26_1 \ldots 26_R$, $24_1 \ldots 24_P$, error propagation through the stages of the process should be minimized. To that end, the location unit 40 of each of the first responder packs $22_1 \ldots 22_N$, similar location units of the drop packs $26_1 \ldots 26_R$ and the patient packs $24_1 \ldots 24_P$ (described later on), and similar location units of the ECAS outstations $28_1 \ldots 28_M$ (also described later on), may employ wireless technology allowing a location of each of these components to be determined with an excessive level of precision, such as 1 m or better (e.g., 50 cm or even less), to permit a build-up of tolerances in a concatenated location approach to maintain an adequate final level of accuracy (e.g., this may be on the order of 1 m, for instance, to locate people, but may be much more precise, in some cases less than 30 cm, to allow automated associations between people or between people and equipment). For example, in this embodiment, the location units may employ ultra-wideband (UWB) technology (e.g., UWB tags) which offers increased precision, down to tens of centimeters or less (e.g., dependent upon "burst" envelope rise and fall times and receiver clock accuracy). In addition to permitting an expanded range of applications, such as associating a pack with a person near it, or two people together such as one of the first responders $14_1 \ldots 14_N$ and one of the patients $18_1 \ldots 18_P$, the increased precision of UWB technology helps to minimize error propagation through the stages of the cascaded location process (where positional errors can be cumulative in a complex but deterministic manner).

The identification unit 46 provides identification data serving to identify the first responder pack $22_j$. The identification data may comprise one or more identifiers, such as an alphanumeric code (e.g., a UWB tag code, a serial number associated with the first responder pack $22_j$, etc.). The wireless location signal transmitted by the location unit 40 of the first responder pack $22_j$ may comprise the identification data (or data derived therefrom) to allow the processing system 20 to identify the first responder pack $22_j$ it is locating. In this respect, while they are shown as separate components, it will be recognized that in some embodiments functionality of the identification unit 46 and the location unit 40 (and particularly its location transmitter 41) may be implemented by a common component (e.g., a UWB tag).

In some embodiments, the identification unit 46 may also provide data identifying the first responder $14_j$ to allow the processing system 20 to identify the first responder $14_j$ associated with the first responder pack $22_j$. For example, the identification unit 46 may store an identifier such as name of the first responder $14_j$. The identifier, which may be provided in the identification unit 46 in various ways such as by coding at issue to the first responder $14_j$ or by a process of identification and authentication while in transit to or at arrival at to the incident scene 12 (e.g., a fingerprint scan or entry of the identifier and possibly a password using the user interface 52), can be used to identify the first responder $14_j$ to the ECAS 30 both for first responder/patient association and for ECAS-enabled access to clinical services and communications (e.g., allowing remote clinicians at the healthcare facility 33 to know which first responder, which patient—by proximity—and any collected data so they can provide better support). In cases where the identification unit 46 does not provide data explicitly identifying the first responder $14_j$, the processing system 20 may already store an association between the identification data provided by the identification unit 46 and an identity of the first responder $14_j$ (e.g., further to a provisioning phase where the first responder pack $22_j$ was assigned to the first responder $14_j$).

The sensor unit 48 enables the processing system 20 to understand physical conditions of the incident scene 12 around the first responder $14_j$. This allows detection of various inclement, adverse or hazardous conditions which the first responder $14_j$ (and possibly one or more patients he/she may be handling) may face and alerting the first responder $14_j$ when such conditions are detected (e.g., notifying the first responder $14_j$ to evacuate its current location, either directly when a predetermined threshold is exceeded or in response to a message received from the ECAS 30), thereby improving his/her safety (and that of the one or more patients he/she may be handling).

More particularly, the sensor unit 48 comprises one or more physical sensors for sensing one or more physical parameters (e.g., temperature, pressure, chemical concentration, electromagnetic radiation level such as light intensity or hard radiation level, vibration level, etc.) and/or other physical activity (e.g., motion of a person or object) around the first responder pack $22_j$ and for generating physical data indicative of these one or more physical parameters and/or other physical activity. For example, the sensor unit 48 may comprise one or more of: temperature/heat sensors (e.g., to detect surrounding temperature); pressure sensors (e.g., to detect atmospheric pressure); chemical sensors (e.g., to sense concentrations or traces of chemicals, such as explosive substances); mass/weight sensors (e.g., to sense mass/weight of persons or objects); vibration sensors (e.g., to sense ground vibrations); movement sensors (e.g., to sense movement of persons or objects); sound sensors (e.g., to sense voices, mechanical sounds, sounds from movement); visible light sensors (e.g., to sense visible light intensity); infrared light sensors (e.g., to sense infrared light emitted by persons or objects or effect video surveillance); RF sensors (e.g., to sense RF emissions or interference); hard radiation sensors (e.g., to sense x-rays, gamma rays or other hard radiation to effect Geiger counter/detection of nuclear decay, hidden object sensing); biotoxin sensors (e.g., to sense airborne or surface toxins, bacteria or viruses); cameras (e.g., to detect movement or identify person or objects, for instance, to effect video surveillance or provide imagery of a nearby patient to remote clinicians at the healthcare facility 33); liquid sensors (e.g., to sense presence of water or other liquids); and gas/vapor sensors (e.g., to sense presence of hazardous or harmful gases such as $H_2S$, CO, methane or propane, and/or hazardous or harmful vapors or gases such as chlorine, fluorine, bromine or petroleum vapors; to sense inadequate levels of oxygen, or presence of smoke or combustion products; etc). These examples are presented for illustrative purposes only as the sensor unit 48 may comprise sensors with various other sensing capabilities.

In addition to its location and sensing functions, the first responder pack $22_j$ can serve as a remote field-located communications terminal linked to the ECAS 30 and other resources of the healthcare facility 33, enabling the first responder $14_j$ to be treated as a clinician with a specific set of services and access rights, as appropriate to first responders and adapted by the ECAS 30 understanding the first responder's context.

More specifically, the user interface 52 enables the first responder $14_j$ to exchange information with the ECAS 30. It comprises a display and possibly one or more other output elements (e.g., a speaker, etc.) enabling the first responder pack $22_j$ to present information to the first responder $14_j$, as well as one or more input elements (e.g., a keyboard, a microphone, a pointing device, a touch sensitive surface, a stylus perhaps built into a glove finger, etc.) enabling the first responder $14_j$ to input information into the first responder pack $22_j$. These input and output elements of the user interface 52 may be adapted for rough and hostile outside conditions and/or various levels of illumination from direct sunlight to near-darkness in which the first responder $14_j$ may evolve at the incident scene 12, and be able to be operated by the first responder $14_j$ when in appropriate protective clothing (e.g., a heavy coat and gloves in winter conditions).

Various exchanges of information may take place between the first responder $14_j$ and the ECAS 30 using the user interface 52. For example, the first responder $14_j$ may: pull up any available information from an electronic healthcare record, such as an electronic health record (EHR), electronic patient record (EPR) or electronic medical record (EMR), of a patient he/she is treating should it exist and should the patient have been identified; open up and populate a medical data file with information about the patient, such as personal information, his/her condition and/or what has been done to the him/her by the first responder $14_j$, by a semi-automated process (which may involve the patient's patient back as discussed below), the medical data file being integrated into the patient's EHR, EPR or EMR if it can be cross-referenced thereto or being delivered as a stand-alone record; use decision information support tools (DIST) or other applications implemented by the ECAS 30; and/or receive information regarding actions to be performed, such as administering certain medical treatment to one or more of the patients $18_1 \ldots 18_P$, transporting one or more of the patients $18_1 \ldots 18_P$ to a given healthcare facility, moving himself/herself or one or more of the patients $18_1 \ldots 18_P$ to a different location, etc, based on determinations made by the ECAS 30. In this respect, the first responder pack $22_j$ may interact with the ECAS 30 to identify and authenticate the first responder $14_j$ and to provide him/her with a broad range of services and capabilities based upon his/her authorization profile, but adapted by the ECAS's computed current situational and institutional context surrounding the first responder $14_j$.

The communication unit 59 is configured to enable the first responder $14_j$ to wirelessly communicate with other parties, such as other ones of the first responders $14_1 \ldots 14_N$, individuals remote from the incident scene 12 such as doctors or other clinicians at the healthcare facility, and/or automated speech, text and/or image processing systems. In particular, the communication unit 59 enables the first responder $14_j$ to communicate with clinicians at the healthcare facility 33, especially those in its receiving ER, both to allow these clinicians to assist in stabilizing a patient treated by the first responder $14_j$ and to allow these clinicians to better prepare to receive that patient. To achieve its function, the communication unit 59 comprises a microphone and possibly other input elements (e.g., a keypad, touch sensitive surface) as well as a speaker and possibly other output elements (e.g., a display) to allow the first responder $14_j$ to communicate. The communication unit 59 also comprises a transmitter and a receiver to send and receive wireless signals establishing communications involving the first responder $14_j$. In some embodiments, the communication unit 59 may be integrated with one or more other devices of the first responder pack $22_j$, in particular, it may be implemented by the processing entity 50, the wireless interface 42 and the user interface 52. In other embodiments, the communication unit 59 may be implemented as a communication device (e.g., a mobile phone, including a wireless-enabled personal digital assistant (PDA)) which may be separate from the user interface 52 and the wireless interface 42 of the first responder pack $22_j$ and which may linked to an emergency wireless network or a service provider wireless network.

The wireless interface 42 provides a bidirectional communication capability to connect the first responder pack $22_j$ to the ECAS outstations $28_1 \ldots 28_M$ (e.g., to report location and sensor information) and, in embodiments where it is used to implement the communication unit 59, to provide a bidirectional communication channel for the first responder $14_j$.

More particularly, the wireless interface 42 comprises a wireless transmitter to transmit wireless signals destined for one or more of the ECAS outstations $28_1 \ldots 28_M$ and conveying data generated by the first responder pack $22_j$, such as data derived from a wireless location signal received by its location receiver 43 (e.g., data related to a time of arrival of that signal), data generated by its sensor unit 48 and/or data derived from input made by the first responder $14_j$ via the user interface 52. Also, the wireless interface 42 comprises a wireless receiver to receive wireless signals from one or more of the ECAS outstations $28_1 \ldots 28_M$ and conveying data destined for the first responder pack $22_j$, such as data representing information to be presented to the first responder $14_j$ via the user interface 52 (e.g., information regarding actions to be performed, such as administering certain medical treatment to one or more of the patients $18_1 \ldots 18_P$, transporting one or more of the patients $18_1 \ldots 18_P$ to a given healthcare facility, moving himself/herself or one or more of the patients $18_1 \ldots 18_P$ to a different location, etc.) and/or data indicative of commands to be executed by the first responder pack $22_j$ (e.g., commands to activate/deactivate the location receiver 43 and/or one or more sensors of the sensor unit 48).

The processing entity 50 performs various processing operations to implement functionality of the first responder pack $22_j$. For example, these processing operations may include operations to: process data generated by the sensor unit 48, data derived from a wireless location signal received by the location receiver 43 (e.g., data related to a time of arrival of that signal), and data derived from input made by the first responder $14_j$ via the user interface 52; activate/deactivate components of the first responder pack $22_j$ (e.g., the location receiver 43 and/or one or more sensors of the sensor unit 48); cause the wireless interface 42 to transmit a wireless signal conveying data derived from a wireless location signal received by the location receiver 43 (e.g., data related to a time of arrival of that signal), data generated by the sensor unit 48 and/or data derived from input made by the first responder $14_j$ via the user interface 52; cause the user interface 52 to present (e.g., display) to the first responder $14_j$ information derived from a wireless signal received via the wireless interface 42; etc.

The processing operations may also implement a timing and synchronization function to ensure that the location transmitter 41 transmits wireless location signals at precise instants and that times of arrival of wireless locations signals at the location receiver 43 are accurately measured. This measurement may be made based on an absolute timing reference that can be distributed amongst the packs $22_1 \ldots 22_N$, $24_1 \ldots 24_P, 26_1 \ldots 26_R$ and the ECAS outstations $28_1 \ldots 28_M$. Alternatively, the measurement may be made relative to a local timing of the location transmitter 41, in which case a "relative" time of reception at the location receiver 43 of a wireless location signal transmitted by an unlocated one of the packs $22_1 \ldots 22_N, 24_1 \ldots 24_P, 26_1 \ldots 26_R$ can be captured and forwarded to the processing system 20. Since it knows the times of reception of wireless location signals transmitted by the location transmitter 41 and has computed the location of that transmitter, the processing system 20 can compute the distance to and hence time of flight from the location receiver 43 and thus can determine, from the measured and reported relative time, the actual time of arrival at the location receiver 43 of the wireless location signal transmitted by the unlocated pack. (For example, considering a case in which the pack 14 $22_j$ is 114 ft away from the ECAS outstation $28_k$ and receives a wireless location signal from a further away unlocated pack, say pack X, at 85 ns before its own wireless location signal is transmitted and passes this data on to the ECAS outstation $28_k$, the ECAS outstation $28_k$ may look at the timing of the located pack's signals (say an arbitrary 405 ns reference its own time datum) and subtract the time of flight of 114 ns from that to determine that the pack $22_j$ transmitted at 291 ns and subtract 85 ns from that to determine that the unlocated pack's signal was received at the located pack $22_j$ at 206 ns. If this is compared with the results from two other located packs, say packs B and C, for instance, yielding results of 222 ns and 175 ns then the differential differences are pack B—pack $22_j$=222−206=16 ns, pack B—pack C=222−175=47 ns and pack $22_j$—pack C=206−175=31 ns, placing the unlocated pack X at 16 ft further from pack B than pack $22_j$, 47 ft further from pack B than pack C and 31 ft further from pack C than pack B. Knowing the locations of the packs $22_j$, B, C, the processing system 20 can "draw" the lines of location which meet the criterion of being 16 ft further from pack B than the pack $22_j$, another set of lines of location which meet the criterion of being 47 ft further from pack B than pack C and yet another set of lines which meet the criterion of being 31 ft further from pack A than pack C. These lines intersect at only one point, which corresponds to the location of the unlocated pack.)

The processing entity 50 comprises one or more processors to perform its various processing operations. A given one of these one or more processors may be a general-purpose processor having access to a storage medium (e.g., semiconductor memory, including one or more ROM and/or RAM memory devices) storing program code for execution by that processor to implement the relevant processing operations. Alternatively, a given one of these one or more processors may be a specific-purpose processor comprising one or more pre-programmed hardware or firmware elements (e.g., application-specific integrated circuits (ASICs), electrically erasable programmable read-only memories (EEPROMs), etc.) or other related elements to implement the relevant processing operations.

The power supply 44 comprises one or more batteries and/or other power storage elements to supply power to the various components of the first responder pack $22_j$. The power supply 44 has a power capacity enabling the first responder pack $22_j$ to be used as long as possible for purposes of the first response mission at the incident scene 12 (e.g., about sixteen hours to handle cases where the first responder $14_j$ works a double shift). The power supply 44 may also have charging circuitry to facilitate its recharging. The power supply 44 may also provide power by other means. For example, it may comprise powering elements to provide power based on solar or vibrational energy, which can be used to supplement its primary energy source.

While in this embodiment the first responder pack $22_j$ comprises various components, in other embodiments, it may not comprise all of these components and/or may comprise different components.

b) Patient Packs $24_1 \ldots 24_P$

Figure 3:
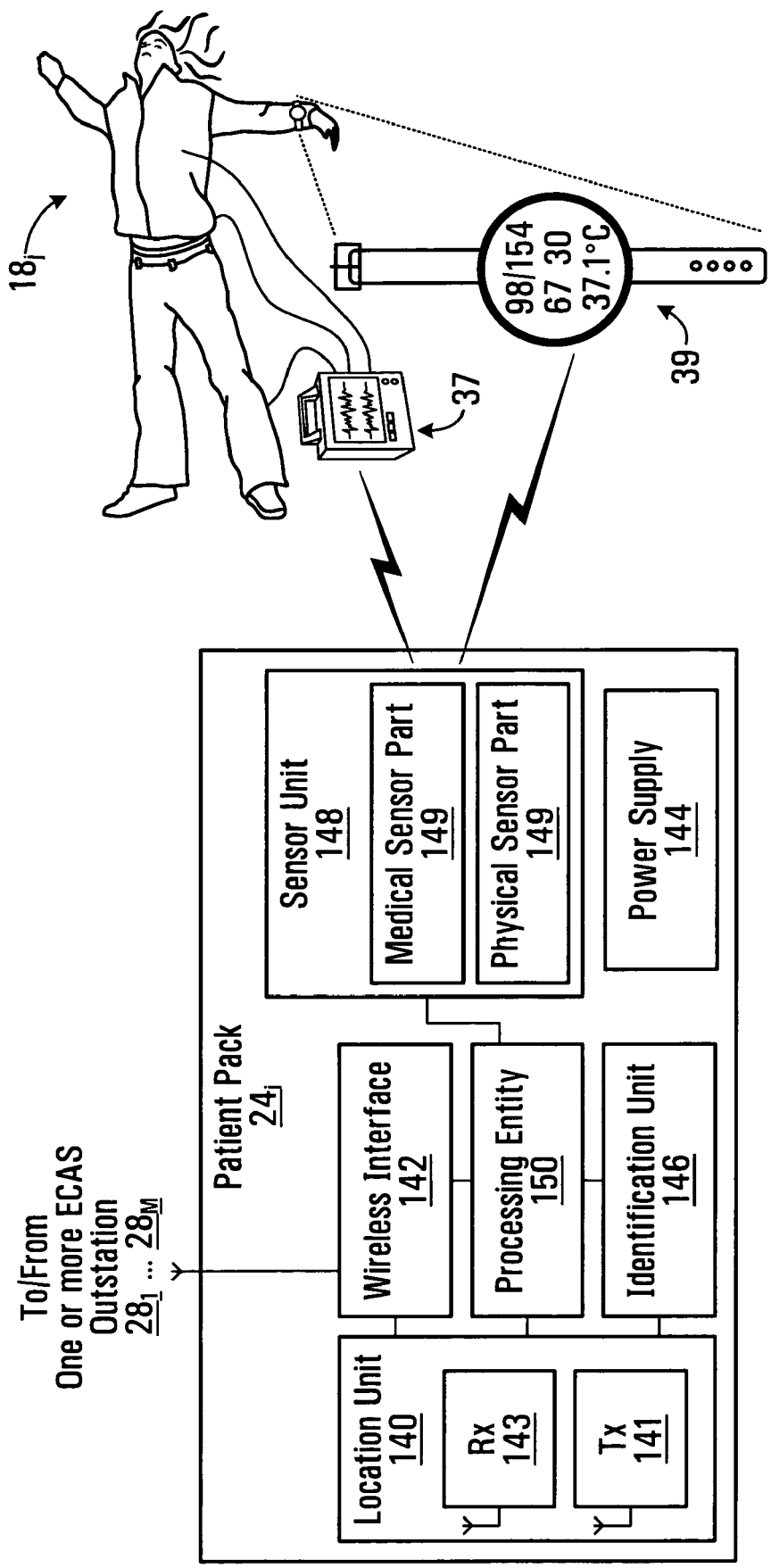
FIG. 3 shows a patient pack of the first response support system, in accordance with an embodiment of the invention.

FIG. 3 shows an embodiment of a patient pack $24_j$ of the patient packs $24_1 \ldots 24_P$ that is personally associated with a patient $18_j$ of the patients $18_1 \ldots 18_P$ at the incident scene 12. Other ones of the patient packs $24_1 \ldots 24_P$ may be similarly constructed.

The patient pack $24_j$ comprises suitable hardware and software (which may include firmware) for implementing a plurality of functional components, including, in this embodiment, a location unit 140, an identification unit 146, a sensor unit 148, a wireless interface 142, a processing entity 150 and a power supply 144. These functional components may be embodied as a single portable device or combination of portable devices carried by a first responder $14_k$ of the first responders $14_1 \ldots 14_N$ at the incident scene 12 until he/she reaches the patient $18_j$ and associates the single portable device or combination of portable devices with the patient $18_j$. For example, the single portable device or combination of portable devices constituting the patient pack $18_j$ may be strapped or otherwise fixed to the patient $18_j$ and/or may be placed adjacent to the patient $18_j$ (e.g., in cases where the patient $18_j$ is expected to remain immobile, for instance, due to injury) by the first responder $14_k$.

The location unit 140 enables the processing system 20 to determine a location of the patient $18_j$. To that end, the location unit 140 comprises a location transmitter (e.g., pinger) 141 to transmit a wireless location signal that allows the processing system 20 to determine the location of the patient pack $24_j$ and, thus, of the patient $18_j$. For example, the wireless location signal may be a short RF burst or series of short RF bursts. More particularly, in this embodiment, the processing system 20 determines the location of the patient $18_j$ based on three or more times of arrival of the wireless location signal at three of more location receivers having known locations that are distributed among some of the ECAS outstations $28_1 \ldots 28_M$ and/or other ones of the packs $22_1 \ldots 22_N$, $26_1 \ldots 26_R$, $24_1 \ldots 24_P$ using triangulation techniques. In other embodiments, rather than allow the processing system 20 to effect location computations based on times of arrival of the wireless location signal transmitted by the location transmitter 141, the wireless location signal may convey other location data that indicates or can be used to compute the location of the patient $18_j$.

In addition, in this embodiment, once the patient pack $24_j$ has been located, the location unit 140 enables the processing system 20 to determine locations of other ones of the packs $22_1 \ldots 22_N$, $26_1 \ldots 26_R$, $24_1 \ldots 24_P$ that are within range of the patient pack $24_j$. To that end, the location unit 140 comprises a location receiver (e.g., a location sensor) 143 to receive wireless location signals from location transmitters of other ones of the packs $22_1 \ldots 22_N$, $26_1 \ldots 26_R$, $24_1 \ldots 24_P$ that are within range of the patient pack $24_j$. As part of the aforementioned cascaded location process (which is further discussed later on), once it has been located by the processing system 20, the patient pack $24_j$ may transmit a wireless signal to the processing system 20 on a basis of the wireless location signals it receives from these location transmitters in order to allow the processing system 20 to determine locations of those packs $22_1 \ldots 22_N$, $26_1 \ldots 26_R$, $24_1 \ldots 24_P$ from which it received the wireless location signals. As mentioned above, in order to minimize error propagation through the stages of the cascaded location process, the location unit 140 may employ wireless technology allowing a location of those packs within its range to be determined with an excessive level of precision, such as 1 m or better (e.g., 50 cm or even less), to permit a build-up of tolerances in a concatenated location approach to maintain an adequate final level of accuracy. For example, in this embodiment, the location unit 140 may employ UWB technology (e.g., a UWB tag) which offers increased accuracy, down to tens of centimeters or less.

The identification unit 146 provides identification data serving to identify the patient pack $24_j$. The identification data may comprise one or more identifiers, such as an alphanumeric code (e.g., a UWB tag code, a serial number associated with the patient pack $24_j$, etc.). The wireless location signal transmitted by the location unit 140 of the patient pack $24_j$ may comprise the identification data (or data derived therefrom) to allow the processing system 20 to identify the patient pack $24_j$ it is locating. In this respect, while they are shown as separate components, it will be recognized that in some embodiments functionality of the identification unit 146 and the location unit 140 (and particularly its location transmitter 141) may be implemented by a common component (e.g., a UWB tag).

In some embodiments, the identification unit 146 may also store data identifying the patient $18_j$ and/or data indicative of his/her status (e.g., his/her condition and/or priority/treatment) to allow the processing system 20 to identify the patient $18_j$ associated with the patient pack $24_j$ and/or know his/her status. For example, the identification unit 146 may store a name and/or healthcare card registration number of the patient $18_j$ and/or a triage code (e.g., a triage color code) assigned to the patient $18_j$. This information may initially be input into the identification unit 146 by the first responder $14_k$ who associates the patient pack $24_j$ with the patient $18_j$. For example, in some cases, the patient pack $24_j$ may comprise a user interface (not shown) comprising a display and possibly one or more other output elements (e.g., a speaker, etc.) and one or more input elements (e.g., a keyboard, a microphone, a pointing device, a touch sensitive surface, a stylus, etc.) to enable the first responder $14_k$ to enter the patient's name (and/or other identifier) and/or the triage code into the identification unit 146. As an alternative, the first responder $14_k$ may activate a predetermined identifier for the patient pack $24_j$, which becomes the identifier associated with data regarding the patient $18_j$ (e.g., patient clinical and non-clinical data) until a patient identity is made/added, either at activation or at a subsequent time. In other cases, the first responder $14_k$ may use the user interface 52 of his/her first responder pack $22_k$ to enter the patient's name and/or the triage code into the identification unit 146 of the patient pack $24_j$. For instance, each of the first responder pack $22_k$ and the patient pack $24_j$ may comprise a short-range data exchange interface (e.g., an infrared data exchange interface) via which the patient's name and/or the triage code entered into the first responder pack $22_k$ by the first responder $14_k$ may be transferred to the identification unit 146 of the patient pack $24_j$. Alternatively, upon establishment of a proximate state between the patient pack $24_j$ and first responder pack $22_k$, the processing system 20 may create an association between the first responder $14_k$ and the patient $18_j$ and, as soon as the first responder $14_k$ captures an identity for the patient (e.g. "Mr. John Smith III of 17 Crestview Drive, Richmond", patient with health card registration # 023-6043-507321, or just unknown casualty #17) using his/her first responder pack $22_k$, this identity is added to the association and from there is downloaded into the patient pack $24_j$ via a given one of the ECAS outstation $28_1 \ldots 28_M$ and the wireless interface 142.

Alternatively or additionally, in some embodiments, the first responder $14_k$ may place an ID bracelet on the patient $18_j$ and use this ID bracelet to provide information identifying the patient $18_j$ to the processing system 20. The ID bracelet may have a readable identifier (e.g., a barcode, an alphanumeric code, etc.) which the first responder $14_k$ may associate with the identification data stored in the identification unit 146 of the patient pack $24_j$ in order to allow the processing system 20 to identify the patient $18_j$ associated with the patient pack $24_j$.

For example, in one embodiment, the readable identifier of the ID bracelet may be a machine-readable identifier (e.g., a barcode), the patient pack $24_j$ may be provided with a machine-readable identifier conveying part or all of the identification data stored in the identification unit 146 (e.g., a UWB tag code), and the first responder pack $22_k$ may comprise a suitable reader (e.g., a barcode reader) to read each of these two identifiers. Upon using this reader to read the two identifiers, the first responder $14_k$ may use the user interface 52 of the first responder pack $22_k$ to enter the patient's name and triage code and/or other status data. In order to expedite this data entry process, the processing entity 50 of the first responder pack $22_k$ may implement a data entry application including a database of common first and last names and/or a list of triage codes and/or other codes indicative of frequent medical condition or necessities (e.g., "immobilize patient before transportation", for instance, in case of a severe neck injury), whereby the first responder $14_k$ can rapidly enter the patient's name by entering starting letters and selecting from a list of candidate names from the database and/or can quickly select a desired triage code or other relevant code from the list of codes. Once this information is entered, the first responder pack $22_k$ may transmit a wireless signal conveying the identifier read from the ID bracelet and the identifier read from the patient pack $24_j$, as well as the patient's name and/or the triage or other code, to the processing system 20 via its wireless interface 42 in order to allow the processing system 20 to identify the patient $18_j$ associated with the patient pack $24_j$ and know his/her status.

As another example, in one embodiment, the readable identifier of the ID bracelet may be a human-readable identifier (e.g., an alphanumeric code) and the patient pack $24_j$ may be provided with a human-readable identifier conveying part or all of the identification data stored in the identification unit 146 (e.g., a UWB tag code or a code associated therewith in the processing system 20). In this case, the first responder $14_k$ may use the user interface 52 of his/her first responder pack $22_k$ to enter each of these two identifiers as well as the patient's name and triage code or other status data, and, once this information is entered, the first responder pack $22_k$ may transmit a wireless signal conveying this information to the processing system 20 via its wireless interface 42 in order to allow the processing system 20 to identify the patient $18_j$ associated with the patient pack $24_j$.

In other examples, the processing system 20 may identify the patient $18_j$ associated with the patient pack $24_j$ in various other ways, based on an association between the readable identifier of the ID bracelet and the identification data stored in the identification unit 24 of the patient pack $24_j$. Also, in other examples, other types of wearable identification elements (e.g., badges, stickers, etc.) having a readable identifier may be placed on the patient $18_j$ instead of an ID bracelet.

In view of the foregoing, when the first responder $14_k$ associates the patient pack $24_j$ with the patient $18_j$, the processing system 20 detects proximity of the first responder $14_k$ to the patient $18_j$ and, based on this proximity, proceeds to create an association between the first responder $14_k$ and the patient $18_j$. In cases where the first responder $14_k$ ascertained the identity of the patient $18_j$, the first responder $14_k$ may be able to access any pre-existing EHR, EMR or EPR information for the patient $18_j$, suitably filtered for first response use, using his/her first responder pack $22_k$ and the healthcare facility 33 may be able to better prepare for receiving the patient $18_j$ since it can both track the patient's context, status and progress as he/she is handled coming out of the incident scene en route to its ER. The first responder $14_k$ and/or remote clinicians at the healthcare facility 33 can thus be made aware (from the patient EHR as well as field data) of pre-existing special circumstances surrounding the patient $18_j$. For example, if the patient $18_j$ is comatose from his/her injuries and may also be diabetic, his/her blood sugar may be monitored closely. As another example, if the patient $18_j$ is known to have a pre-existing heart condition and has a crushed left leg resulting from events at the incident scene 12, he/she has an increased chance of dying due to stress-induced heart failure and so must be treated differently than a healthy person with the same injury. In cases where the patient $18_j$ cannot readily be medically identified and associated with medical records, he/she may still be allocated a unique but arbitrary identifier to track their progress and treatment until they arrive at the healthcare facility 33.

The sensor unit 148 enables the processing system 20 to understand physical conditions of the incident scene 12 around the patient $14_j$, allowing detection of various inclement, adverse or hazardous conditions surrounding the patient $14_j$, thereby improving his/her safety. In addition, the sensor unit 148 enables monitoring of a medical condition of the patient $14_j$ that is reported to the ECAS 30. This allows the ECAS 30 to continuously monitor the patient $14_j$ at the incident scene 12, even if no first responder can be with him/her (e.g., in cases where there are more casualties than first responders). This can also allow the ECAS 30, which may have access to EHR, EMR or EPR information of the patient $14_j$, to detect potential flag-able impairments based on the patient's condition, and signal same back to the first responder $14_k$. To that end, the sensor unit 148 comprises a physical sensor part 147 and a medical sensor part 149.

The physical sensor part 147 comprises one or more physical sensors for sensing one or more physical parameters (e.g., temperature, pressure, chemical concentration, electromagnetic radiation level such as light intensity or hard radiation level, vibration level, etc.) and/or other physical activity (e.g., motion of a person or object) around the patient pack $24_j$ and for generating data indicative of these one or more physical parameters and/or other physical activity. For example, the sensor unit 148 may comprise one or more of: temperature/heat sensors (e.g., to detect surrounding temperature); pressure sensors (e.g., to detect atmospheric pressure); chemical sensors (e.g., to sense concentrations or traces of chemicals, such as explosive substances); mass/weight sensors (e.g., to sense mass/weight of persons or objects); vibration sensors (e.g., to sense ground vibrations); movement sensors (e.g., to sense movement of persons or objects); sound sensors (e.g., to sense voices, mechanical sounds, sounds from movement); visible light sensors (e.g., to sense visible light intensity) infrared light sensors (e.g., to sense infrared light emitted by persons or objects or effect video surveillance); RF sensors (e.g., to sense RF emissions or interference); hard radiation sensors (e.g., to sense x-rays, gamma rays or other hard radiation to effect Geiger counter/detection of nuclear decay, hidden object sensing); biotoxin sensors (e.g., to sense airborne or surface toxins, bacteria or viruses); cameras (e.g., to detect movement or identify person or objects, for instance, to effect video surveillance or provide imagery of the patient $18_j$ to remote clinicians at the healthcare facility 33); liquid sensors (e.g., to sense presence of water or other liquids); and gas/vapor sensors (e.g., to sense presence of hazardous or harmful gases such as $H_2S$, CO, methane or propane, and/or hazardous or harmful vapors or gases such as chlorine, fluorine, bromine or petroleum vapors; to sense inadequate levels of oxygen, or presence of smoke or combustion products; etc). These examples are presented for illustrative purposes only as the physical sensor part 147 may comprise sensors with various other sensing capabilities.

The medical sensor part 149 comprises one or more physiological sensors for sensing one or more physiological parameters of the patient $18_j$ and for generating data indicative of these one or more physiological parameters. For example, the sensor unit 148 may comprise one or more sensors for sensing a heart rate, blood pressure, body temperature, oxygenation level, breathing rate, or toxin level of the patient $18_j$, or for sensing any other physiological parameter relevant to evaluating the patient's medical condition (in that sense, the physiological parameters sensed by the medical sensor part 149 can also be referred to as "medical parameters"). Each physiological sensor of the medical sensor part 149 may be strapped (e.g., to a wrist) or otherwise externally fixed on the patient's body and/or may be partially or entirely inserted into the patient's body (e.g., intradermally, intravenously). For instance, in some embodiments, various physiological sensors of the medical sensor part 149 may be included in a wrist bracelet 39 worn by the patient $18_j$ (which can also serve as an ID bracelet) and a patient monitor 37 wired to the patient $18_j$, both wirelessly connected (e.g., via a Bluetooth® or equivalent short-range wireless link) to a wireless receiver of the medical sensor part 149.

The wireless interface 142 provides a bidirectional communication capability to connect the patient pack $24_j$ to the ECAS outstations $28_1 \ldots 28_M$ (e.g., to report location and sensor information). More particularly, the wireless interface 142 comprises a wireless transmitter to transmit wireless signals destined for one or more of the ECAS outstations $28_1 \ldots 28_M$ and conveying data generated by the patient pack $24_j$, such as data derived from a wireless location signal received by its location receiver 143 (e.g., data related to a time of arrival of that signal) and/or data generated by its sensor unit 148. Also, the wireless interface 142 comprises a wireless receiver to receive wireless signals from one or more of the ECAS outstations $28_1 \ldots 28_M$ and conveying data destined for the patient pack $24_j$, such as data indicative of commands to be executed by the patient pack $24_j$ (e.g., commands to activate/deactivate the location receiver 143 and/or one or more sensors of the sensor unit 148).

The processing entity 150 performs various processing operations to implement functionality of the patient pack $24_j$. For example, these processing operations may include operations to: process data generated by the sensor unit 148 and data derived from a wireless location signal received by the location receiver 143 (e.g., data related to a time of arrival of that signal); activate/deactivate components of the patient pack $24_j$ (e.g., the location receiver 143 and/or one or more sensors of the sensor unit 148); cause the wireless interface 142 to transmit a wireless signal conveying data generated by the sensor unit 148 and/or data derived from a wireless location signal received by the location receiver 143 (e.g., data related to a time of arrival of that signal); etc.

The processing operations may also implement a timing and synchronization function to ensure that the location transmitter 141 transmits wireless location signals at precise instants and that times of arrival of wireless locations signals at the location receiver 143 are accurately measured. This measurement may be made based on an absolute timing reference that can be distributed amongst the packs $22_1 \ldots 22_N$, $24_1 \ldots 24_P$, $26_1 \ldots 26_R$ and the ECAS outstations $28_1 \ldots 28_M$. Alternatively, the measurement may be made relative to a local timing of the location transmitter 141, in which case a "relative" time of reception at the location receiver 143 of a wireless location signal transmitted by an unlocated one of the packs $22_1 \ldots 22_N$, $24_1 \ldots 24_P$, $26_1 \ldots 26_R$ can be captured and forwarded to the processing system 20. Since it knows the times of reception of wireless location signals transmitted by the location transmitter 141 and has computed the location of that transmitter, the processing system 20 can compute the distance to and hence time of flight from the location receiver 143 and thus can determine, from the measured and reported relative time, the actual time of arrival at the location receiver 143 of the wireless location signal transmitted by the unlocated pack.

The processing entity 150 comprises one or more processors to perform its various processing operations. A given one of these one or more processors may be a general-purpose processor having access to a storage medium (e.g., semiconductor memory, including one or more ROM and/or RAM memory devices) storing program code for execution by that processor to implement the relevant processing operations. Alternatively, a given one of these one or more processors may be a specific-purpose processor comprising one or more pre-programmed hardware or firmware elements (e.g., ASICs, EEPROMs, etc.) or other related elements to implement the relevant processing operations.

The power supply 144 comprises one or more batteries and/or other power storage elements to supply power to the various components of the patient pack $24_j$. The power supply 144 has a power capacity enabling the patient pack $24_j$ to be used as long as possible for purposes of the first response mission at the incident scene 12 (e.g., a few hours to allow sufficient time to provide proper treatment to the patient $18_j$ and/or transport him/her to the healthcare facility 33). The power supply 144 may also have charging circuitry to facilitate its recharging. The power supply 144 may also provide power by other means. For example, it may comprise powering elements to provide power based on solar or vibrational energy, which can be used to supplement its primary energy source.

While in this embodiment the patient pack $24_j$ comprises various components, in other embodiments, it may not comprise all of these components and/or may comprise different components. For example, in some embodiments, the patient pack $24_j$ may comprise a communication unit enabling the patient $18_j$ to wirelessly communicate with the first responders $14_1 \ldots 14_N$ and/or remote clinicians or support staff at the healthcare facility 33 via the ECAS outstations $28_1 \ldots 28_M$ and/or an emergency wireless network or a service provider wireless network (e.g., a system analogous to a hospital nurse-call system), when left unattended.

c) Drop Packs $26_1 \ldots 26_R$

The drop packs $26_1 \ldots 26_R$ are optional components of the first response support system 10 that can serve to improve the system's coverage and resolution at the incident scene 12, both in terms of location-awareness and physical conditions sensing, irrespective of whether the first responders $14_1 \ldots 14_N$ remain at locations where they are dropped. For example, in cases where the first response vehicles $16_1 \ldots 16_M$ have to stop some distance away from a "main action area" of the incident scene 12, the first responders $14_1 \ldots 14_N$ may place multiple ones of the drop packs $26_1 \ldots 26_R$ between the first response vehicles $16_1 \ldots 16_M$ and the main action area to allow a concatenated extension of the location-awareness capability out to the main action area. As another example, multiple ones of the drop packs $26_1 \ldots 26_R$ can be placed around or near anticipated sources of hazardous conditions such as burning buildings or vehicles, leaking tanks of hazardous or combustible materials, etc. As yet another example, multiple ones of the drop packs $26_1 \ldots 26_R$ can also be used to provide more data location data points and physical conditions data points at the incident scene 12 (e.g., additional drop packs may be placed around a burning building before first responders such as firemen enter the building so as to provide very high location coverage through the building's walls to track the locations of these firemen).

Figure 4:
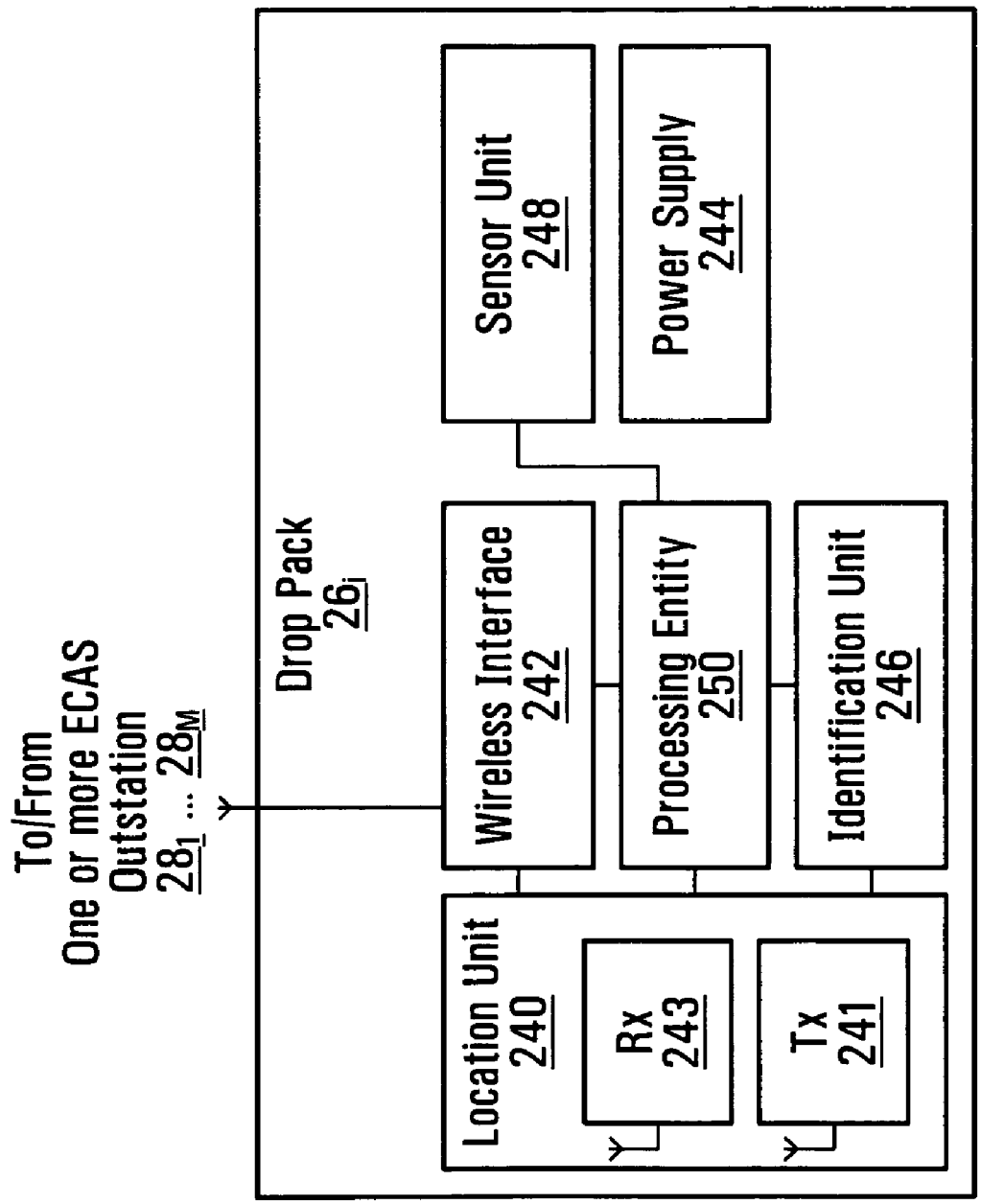
FIG. 4 shows a drop pack of the first response support system, in accordance with an embodiment of the invention.

FIG. 4 shows an embodiment of a drop pack $26_j$ of the drop packs $26_1 \ldots 26_R$ that is "dropped" (i.e., placed) at any suitable location at the incident scene 12. Other ones of the drop packs $26_1 \ldots 26_R$ may be similarly constructed.

The drop pack $26_j$ comprises suitable hardware and software (which may include firmware) for implementing a plurality of functional components, including, in this embodiment, a location unit 240, an identification unit 246, a sensor unit 248, a wireless interface 242, a user interface 252, a processing entity 250 and a power supply 244. These functional components may be embodied as a single portable device or combination of portable devices carried by a first responder 14$_i$ of the first responders 14$_1$ ... 14$_N$ at the incident scene 12 until it is dropped by the first responder 14$_i$ at any suitable location at the incident scene 12. For example, the single portable device or combination of portable devices constituting the drop pack 26$_j$ may be arranged as a portable case to be carried by the first responder 14$_i$ until it is dropped at the incident scene 12. A decision to drop the drop pack 26$_j$ at a given location may be made by the first responder 14$_i$ or by the processing system 20 which detects that the first responder 14$_i$ is approaching limits of its active location area and commands the drop pack 26$_j$ to be dropped at that given location. Exact placement of the drop pack 26$_j$ is not required since its location will be determined by the processing system 20. In some cases, one or more other drop packs may be carried by the first responder 14$_i$ in addition to the drop pack 26$_j$ (e.g., inside a single portable housing) and dropped at various locations at the incident scene 12.

The location unit 240 enables the processing system 20 to determine a location of the drop pack 26$_j$. To that end, the location unit 240 comprises a location transmitter (e.g., pinger) 241 to transmit a wireless location signal that allows the processing system 20 to determine the location of the drop pack 26$_j$. For example, the wireless location signal may be a short RF burst or series of short RF bursts. More particularly, in this embodiment, the processing system 20 determines the location of the drop pack 26$_j$ based on three or more times of arrival of the wireless location signal at three or more location receivers having known locations that distributed among some of the ECAS outstations 28$_1$ ... 28$_M$ and/or other ones of the packs 22$_1$ ... 22$_N$, 26$_1$ ... 26$_R$, 24$_1$ ... 24$_P$ using triangulation techniques. In other embodiments, rather than allow the processing system 20 to effect location computations based on times of arrival of the wireless location signal transmitted by the location transmitter 241, the wireless location signal may convey other location data that indicates or can be used to compute the location of the drop pack 26$_j$.

In addition, in this embodiment, once the drop pack 26$_j$ has been located, the location unit 240 enables the processing system 20 to determine locations of other ones of the packs 22$_1$ ... 22$_N$, 26$_1$ ... 26$_R$, 24$_1$ ... 24$_P$ that are within range of the drop pack 26$_j$. To that end, the location unit 240 comprises a location receiver (e.g., a location sensor) 243 to receive wireless location signals from location transmitters of other ones of the packs 22$_1$ ... 22$_N$, 26$_1$ ... 26$_R$, 24$_1$ ... 24$_P$ that are within range of the drop pack 26$_j$. As part of the aforementioned cascaded location process (which is further discussed later on), once it has been located by the processing system 20, the drop pack 26$_j$ may transmit a wireless signal to the processing system 20 on a basis of the wireless location signals it receives from these location transmitters in order to allow the processing system 20 to determine locations of those packs 22$_1$ ... 22$_N$, 26$_1$ ... 26$_R$, 24$_1$ ... 24$_P$ from which it received the wireless location signals. As mentioned above, in order to minimize error propagation through the stages of the cascaded location process, the location unit 240 may employ wireless technology allowing a location of those packs within its range to be determined with an excessive level of precision, such as 1 m or better (e.g., 50 cm or even less), to permit a build-up of tolerances in a concatenated location approach to maintain an adequate final level of accuracy. For example, in this embodiment, the location unit 240 may employ UWB technology (e.g., a UWB tag) which offers increased accuracy, down to tens of centimeters or less.

The identification unit 246 provides identification data serving to identify the drop pack 26$_j$. The identification data may comprise one or more identifiers, such as an alphanumeric code (e.g., a UWB tag code, a serial number associated with the drop pack 26$_j$, etc.). The wireless location signal transmitted by the location unit 240 of the drop pack 26$_j$ may comprise the identification data (or data derived therefrom) to allow the processing system 20 to identify the drop pack 26$_j$ it is locating. In this respect, while they are shown as separate components, it will be recognized that in some embodiments functionality of the identification unit 246 and the location unit 240 (and particularly its location transmitter 241) may be implemented by a common component (e.g., a UWB tag).

The sensor unit 248 enables the processing system 20 to understand physical conditions of the incident scene 12 around the drop pack 26$_j$, allowing detection of various inclement, adverse or hazardous conditions surrounding the drop pack 26$_j$, which may improve safety of individuals such as one or more of the first responders 14$_1$ ... 14$_N$ or patients 18$_1$ ... 18$_P$ who may be near the pack or heading or expected to head towards it.

More particularly, the sensor unit 248 comprises one or more physical sensors for sensing one or more physical parameters (e.g., temperature, pressure, chemical concentration, electromagnetic radiation level such as light intensity or hard radiation level, vibration level, etc.) and/or other activity (e.g., motion of a person or object) around the drop pack 26$_j$ and for generating data indicative of these one or more physical parameters and/or other physical activity. For example, the sensor unit 248 may comprise one or more of: temperature/heat sensors (e.g., to detect surrounding temperature); pressure sensors (e.g., to detect atmospheric pressure); chemical sensors (e.g., to sense concentrations or traces of chemicals, such as explosive substances); mass/weight sensors (e.g., to sense mass/weight of persons or objects); vibration sensors (e.g., to sense ground vibrations); movement sensors (e.g., to sense movement of persons or objects); sound sensors (e.g., to sense voices, mechanical sounds, sounds from movement); visible light sensors (e.g., to sense visible light intensity) infrared light sensors (e.g., to sense infrared light emitted by persons or objects or effect video surveillance); RF sensors (e.g., to sense RF emissions or interference); hard radiation sensors (e.g., to sense x-rays, gamma rays or other hard radiation to effect Geiger counter/ detection of nuclear decay, hidden object sensing); biotoxin sensors (e.g., to sense airborne or surface toxins, bacteria or viruses); cameras (e.g., to detect movement or identify person or objects, for instance, to effect video surveillance or provide imagery of a nearby patient to remote clinicians at the healthcare facility 33); liquid sensors (e.g., to sense presence of water or other liquids); and gas/vapor sensors (e.g., to sense presence of hazardous or harmful gases such as $H_2S$, CO, methane or propane, and/or hazardous or harmful vapors or gases such as chlorine, fluorine, bromine or petroleum vapors; to sense inadequate levels of oxygen, or presence of smoke or combustion products; etc). These examples are presented for illustrative purposes only as the sensor unit 248 may comprise various sensors with various other sensing capabilities.

The wireless interface 242 provides a bidirectional communication capability to connect the drop pack 26$_j$ to the ECAS outstations 28$_1$ ... 28$_M$ (e.g., to report location and sensor information). More particularly, the wireless interface 242 comprises a wireless transmitter to transmit wireless signals destined for one or more of the ECAS outstations 28$_1$ ... 28$_M$ and conveying data generated by the drop pack 26$_j$, such as data derived from a wireless location signal received by its location receiver 243 (e.g., data related to a time of arrival of that signal) and/or data generated by its sensor unit 248. Also, the wireless interface 242 comprises a wireless receiver to receive wireless signals from one or more of the ECAS outstations $28_1 \ldots 28_M$ and conveying data destined for the drop pack $26_j$, such as data indicative of commands to be executed by the drop pack $26_j$ (e.g., commands to activate/deactivate the location receiver 243 and/or one or more sensors of the sensor unit 248).

The processing entity 250 performs various processing operations to implement functionality of the drop pack $26_j$. For example, these processing operations may include operations to: process data generated by the sensor unit 248 and data derived from a wireless location signal received by the location receiver 243 (e.g., data related to a time of arrival of that signal); activate/deactivate components of the drop pack $26_j$ (e.g., the location receiver 243 and/or one or more sensors of the sensor unit 248); cause the wireless interface 242 to transmit a wireless signal conveying data generated by the sensor unit 248 and/or data derived from a wireless location signal received by the location receiver 243 (e.g., data related to a time of arrival of that signal); etc.

The processing operations may also implement a timing and synchronization function to ensure that the location transmitter 241 transmits wireless location signals at precise instants and that times of arrival of wireless locations signals at the location receiver 243 are accurately measured. This measurement may be made based on an absolute timing reference that can be distributed amongst the packs $22_1 \ldots 22_N$, $24_1 \ldots 24_P$, $26_1 \ldots 26_R$ and the ECAS outstations $28_1 \ldots 28_M$. Alternatively, the measurement may be made relative to a local timing of the location transmitter 241, in which case a "relative" time of reception at the location receiver 243 of a wireless location signal transmitted by an unlocated one of the packs $22_1 \ldots 22_N$, $24_1 \ldots 24_P$, $26_1 \ldots 26_R$ can be captured and forwarded to the processing system 20. Since it knows the times of reception of wireless location signals transmitted by the location transmitter 241 and has computed the location of that transmitter, the processing system 20 can compute the distance to and hence time of flight from the location receiver 243 and thus can determine, from the measured and reported relative time, the actual time of arrival at the location receiver 243 of the wireless location signal transmitted by the unlocated pack.

The processing entity 250 comprises one or more processors to perform its various processing operations. A given one of these one or more processors may be a general-purpose processor having access to a storage medium (e.g., semiconductor memory, including one or more ROM and/or RAM memory devices) storing program code for execution by that processor to implement the relevant processing operations. Alternatively, a given one of these one or more processors may be a specific-purpose processor comprising one or more pre-programmed hardware or firmware elements (e.g., ASICs, EEPROMs, etc.) or other related elements to implement the relevant processing operations.

The power supply 244 comprises one or more batteries and/or other power storage elements to supply power to the various components of the drop pack $26_j$. The power supply 244 has a power capacity enabling the drop pack $26_j$ to be used as long as possible for purposes of the first response mission at the incident scene 12 (e.g., several hours or days or even a few weeks in case of a major disaster). The power supply 244 may also have charging circuitry to facilitate its recharging. The power supply 244 may also provide power by other means. For example, it may comprise powering elements to provide power based on solar or vibrational energy, which can be used to supplement its primary energy source (e.g., to keep powering the location transmitter 241 in cases where the drop pack's main power source has depleted, which can be useful, for instance, in recovering the drop pack once the first response mission is completed).

While in this embodiment the drop pack $26_j$ comprises various components, in other embodiments, it may not comprise all of these components and/or may comprise different components.

ECAS Outstations $28_1 \ldots 28_M$

The ECAS outstations $28_1 \ldots 28_M$ are transported to the incident scene 12 by respective ones of the first response vehicles $16_1 \ldots 16_M$ and provide communication, data processing and other functionality between the packs $22_1 \ldots 22_N$, $24_1 \ldots 24_P$, $26_1 \ldots 26_R$ and the ECAS 30 (and other resources within the healthcare facility 33). In particular, in this embodiment, the ECAS outstations $28_1 \ldots 28_M$ enable communications between the incident scene 12 and the healthcare facility 33, communications to and from the $22_1 \ldots 22_N$, $24_1 \ldots 24_P$, $26_1 \ldots 26_R$, reception of wireless location signals to allow nearby ones of these packs to be located and then activated so that their location receivers 43, 143, 243 can contribute to extending the location-awareness area at the incident scene 12, and collection, collation, filtering or other processing of sensor information transmitted by these packs prior to sending this to the ECAS 30 which creates a multi-environmental-plane view of the incident scene 12.

Figure 5:
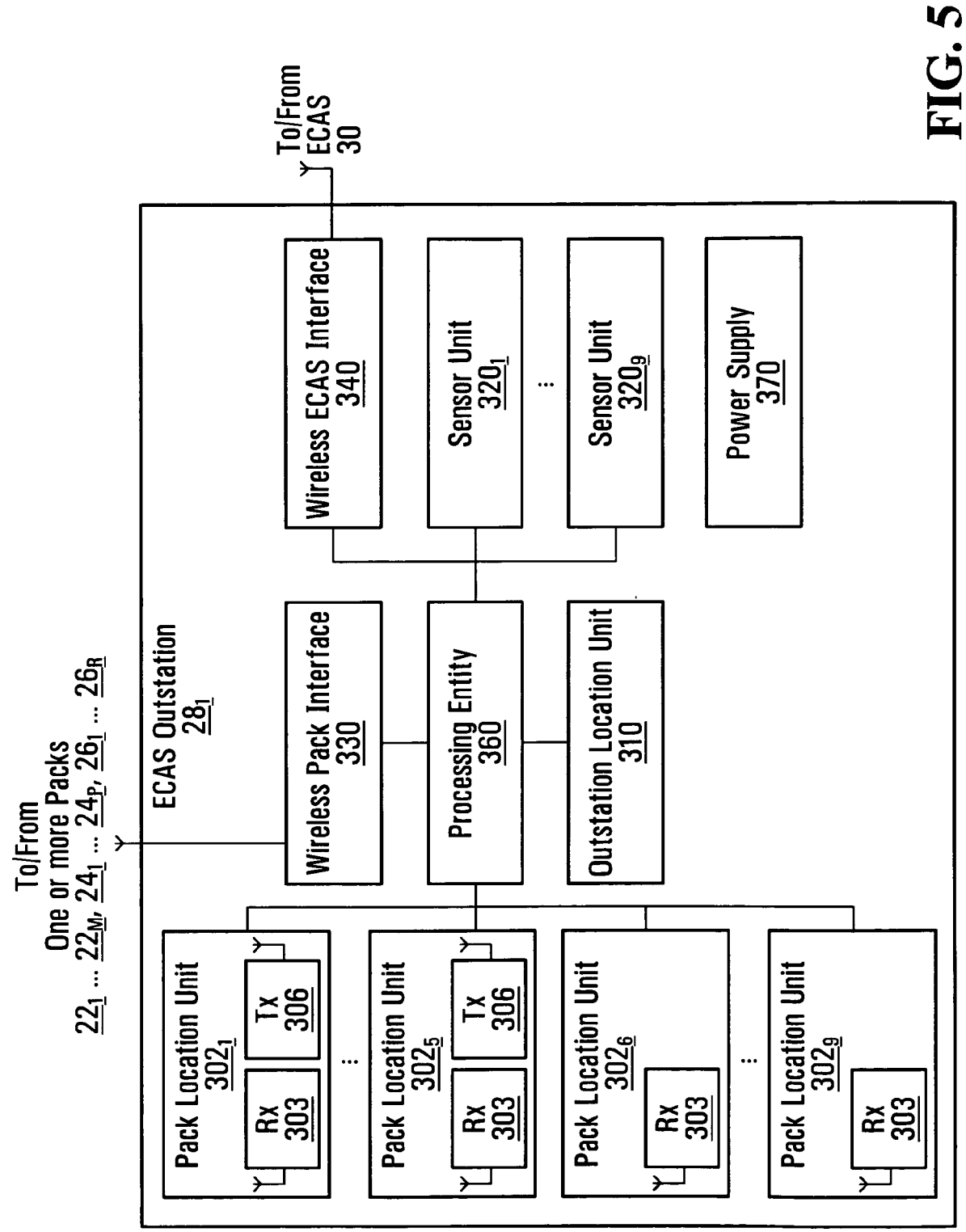
FIG. 5 shows a local processing station of the first response support system, in accordance with an embodiment of the invention.

FIG. 5 shows an embodiment of an ECAS outstation $28_j$ of the ECAS outstations $28_1 \ldots 28_M$ that is transported to the incident scene 12 by a vehicle $16_j$ of the vehicles $16_1 \ldots 16_M$. Other ones of the ECAS outstations $28_1 \ldots 28_M$ may be similarly constructed.

The ECAS outstation $28_j$ comprises suitable hardware and software (which may include firmware) for implementing a plurality of functional components, including, in this embodiment, a plurality of pack location units $302_1 \ldots 302_9$, an outstation location unit 310, a plurality of sensor units $320_1 \ldots 320_9$, a wireless pack interface 330, a wireless ECAS interface 340, a processing entity 360 and a power supply 370. These functional components may be embodied as equipment installed on the vehicle $16_j$ so as to facilitate their transportation to the incident scene 12.

The pack location units $302_1 \ldots 302_9$ are arranged at different positions relative to one another and enable the processing system 20 to determine the locations of individual ones of the packs $22_1 \ldots 22_N$, $26_1 \ldots 26_R$, $24_1 \ldots 24_P$ that are within their range. To that end, each of the pack location units $302_1 \ldots 302_9$ comprises a location receiver 303 to receive wireless location signals transmitted by location transmitters 41, 141, 241 of those packs $22_1 \ldots 22_N$, $26_1 \ldots 26_R$, $24_1 \ldots 24_P$ that are within its range. In order to determine the locations of the packs $22_1 \ldots 22_N$, $26_1 \ldots 26_R$, $24_1 \ldots 24_P$, at least three and preferably more (e.g., four, five or six) location receivers 303 need to "see" the wireless location signals transmitted by these packs. The resolution or precision of the location computation typically depends upon both the distance to the location transmitter 41, 141, 241 of the pack to be located and baseline distances between the location receivers 303 which receive the wireless location signal transmitted by that location transmitter.

More particularly, in this embodiment, the pack location units $302_6 \ldots 302_9$ are fixed at known locations on the vehicle $16_j$. In this case, these locations are non-coplanar to allow location measurements in 3D.

Also, in this embodiment, each of the pack location units $302_1 \ldots 302_5$ is disposed on a tip region of a respective one of a plurality of extensible arms (e.g., booms) $307_1 \ldots 307_5$ that are capable of being extended relative to a body of the vehicle $16_j$. The extensible arms $307_1 \ldots 307_4$ extend substantially horizontally from respective corner regions of the body of the vehicle $16_j$ and are dimensioned to give a certain spread (e.g., 20 to 25 ft) about the body of vehicle $16_j$. This can be done to increase differential path lengths from location receivers to be located and thereby extend a coverage area of sufficient location discrimination by the location receivers 303 of the pack location units $302_1 \ldots 302_4$. The extensible arm $307_5$ extends substantially vertically from a center region of the body of the vehicle $16_j$ to allow the location receiver 303 of the pack location unit $302_5$ to be used in determining z-coordinates of those packs from which it receives wireless location signals. The extensible arms $307_1 \ldots 307_5$ thus provide longer baseline distances between the location receivers 303 of the pack location units $302_1 \ldots 302_5$, thereby providing greater precision and location discrimination out to a greater range.

The locations of the pack location units $302_1 \ldots 302_5$ on the extensible arms $307_1 \ldots 307_5$ have to be known very accurately if these pack location units are to enable the processing system 20 to accurately determine the locations of those packs $22_1 \ldots 22_N$, $26_1 \ldots 26_R$, $24_1 \ldots 24_P$ that are within their range. This can be achieved in various ways. For example, in this embodiment, each of the pack location units $302_1 \ldots 302_5$ comprises a location transmitter (e.g., pinger) 306 to transmit a wireless location signal allowing the processing system 20 to determine a location of that pack location unit. In this case, the processing system 20 determines the location of each of the pack location units $302_1 \ldots 302_5$ based on times of arrival of the wireless location signal transmitted by its location transmitter 306 at three or more of the location receivers 303 of the pack location units $302_6 \ldots 302_9$ at known locations on the vehicle $16_j$ using triangulation techniques. In other embodiments, the locations of the pack location units $302_1 \ldots 302_5$ may be known to the processing system 20 based on engineering and other information regarding the extensible arms $307_1 \ldots 307_5$, such as their actual extension length and orientation, without having to process wireless location signals transmitted by location transmitters such as the location transmitters 306, in which case such location transmitters may be omitted. In yet other embodiments, rather than allow the processing system 20 to effect location computations based on times of arrival of the wireless location signal transmitted by each of the pack location units $302_1 \ldots 302_5$, this wireless location signal may convey data that indicates or otherwise allows computation of the location of that pack location unit (e.g., precise angle of arrival of the signal at each receiver or the signal strength at the receiver, based on clear line-of-sight measurements only or a combination of these).

In the aforementioned cascaded location process which is further detailed later on, the pack location units $302_1 \ldots 302_9$ receive wireless location signals from those packs $22_1 \ldots 22_N$, $26_1 \ldots 26_R$, $24_1 \ldots 24_P$ that are within their range and, based on data derived from these signals (e.g., data relating to their times of arrival at the location receivers 303), the processing entity 360 of the ECAS outstation $28_j$ and/or the ECAS 30 (depending on whether local, remote or distributed location computation is used) can compute the location of each of these packs. Once the locations of these packs are determined, the ECAS outstation $28_j$ can activate the location receivers 43, 143, 243 of these packs and add their measurements to the location computation capability.

As mentioned above, in order to minimize error propagation through the stages of the cascaded location process, the pack location units $302_1 \ldots 302_9$ may employ wireless technology allowing a location of those packs within its range to be determined with an excessive level of precision, such as 1 m or better (e.g., 50 cm or even less), to permit a build-up of tolerances in a concatenated location approach to maintain an adequate final level of accuracy. For example, in this embodiment, the pack location units $302_1 \ldots 302_9$ may employ UWB technology (e.g., UWB tags) which offers increased accuracy, down to tens of centimeters or less.

The outstation location unit 310 allows a location of the ECAS outstation $28_j$ to be determined by the processing system 20. This location can be an absolute location or a relative location (relative to an arbitrary site reference), and in some cases may be accompanied by an orientation of the ECAS outstation $28_j$.

For example, in this embodiment, the outstation location unit 310 may comprise a GPS receiver (with an optional gyroscopic compass) enabling the absolute location (and optionally the orientation) of the ECAS outstation $28_j$ to be determined based on GPS signaling. As the GPS receiver (e.g., a civilian GPS receiver) may yield approximate results, once the ECAS outstation $28_j$ has been located, other ones of the ECAS outstations $28_1 \ldots 28_M$ may have to locate themselves precisely relative to the ECAS outstation $28_j$ by means other than GPS so as to establish accurate baselines between the ECAS outstations $28_1 \ldots 28_M$ to allow their precise relative location to be determined so that location collaboration between them is possible (as described below) to locate packs in intervening spaces between them or to locate packs far away whereby a long baseline is needed should cascaded location not be available. Also, after a precision location map is built up, this can be used to augment the precision of the absolute location of the ECAS outstation $28_j$ (e.g., the ECAS outstation $28_j$ may determine from GPS signaling that its location is within +/−10 meters of 120 meters south of the south wall of 321 Metcalfe Street, but, by measuring the relative location of a drop pack placed at the wall of 321 Metcalfe Street, it may determine that the range to that pack (and hence 321 Metcalfe Street) is 112.3 meters+/−0.7 meters, allowing it to correct its position to being 111.6 to 113 meters south of 321 Metcalfe Street). Furthermore, by using cascaded location capabilities on located ones of the packs $22_1 \ldots 22_N$, $26_1 \ldots 26_R$, $24_1 \ldots 24_P$, combined with an accurate relative location of the ECAS outstations $28_1 \ldots 28_M$, if the locations of all these packs is known relative to any ECAS outstation, they may be known relative to all these ECAS outstations. Thus, any one of the first response vehicles $16_1 \ldots 16_M$ (except the last one) can leave the incident scene 12 as it is loaded with one or more patients, and the location grid will keep operating since those ones of the packs $22_1 \ldots 22_N$, $26_1 \ldots 26_R$, $24_1 \ldots 24_P$ at known locations can bridge across the gap left and report further locations to the remaining vehicles.

In other embodiments, the outstation location unit 310 may comprise a location receiver and a location transmitter to exchange wireless location signals with other ones of the ECAS outstations $28_1 \ldots 28_M$ to allow the absolute or relative location of the ECAS outstation $28_j$ to be determined on a basis of times of arrival of these signals through collaboration between the ECAS outstations $28_1 \ldots 28_M$. In yet other embodiments, relative placement and orientation of the ECAS outstation $28_j$ can be determined from a reference point (e.g. the first one of the first response vehicles $16_1 \ldots 16_M$ on site) by measuring direction and distance to that reference point combined with the orientation of the vehicle $16_j$ to that reference point (e.g., if the reference point is one of the first response vehicles $16_1 \ldots 16_M$, this can be done by use of a high gain/high power version of a UWB location system, which may have a range of up to 1 km or more). In yet other embodiments, the location of the ECAS outstation $28_j$ can be determined with reference to a city level or site level map or with reference to cellular, WiMax or other wireless location technologies that may be available, possibly with appropriate augmentation similar to that applied to the GPS case above to increase location precision once the location grid is established. Location data indicative of the location of the ECAS outstation $28_j$ may be transmitted to the ECAS 30 via the wireless ECAS interface 340 and/or used locally by the ECAS outstation $28_j$ to make location computations.

Each of the sensor units $320_1 \ldots 320_9$ enables the processing system 20 to understand physical conditions of the incident scene 12 around the vehicle $16_j$, allowing detection of various inclement, adverse or hazardous conditions surrounding the vehicle $16_j$, which may improve safety of individuals such as one or more of the first responders $14_1 \ldots 14_N$ or patients $18_1 \ldots 18_P$ who may be in or near the vehicle $16_j$ or heading or expected to head towards it. The sensor units $320_1 \ldots 320_9$ may be co-located with the pack location units $302_1 \ldots 302_9$ or located at other locations.

More particularly, each of the sensor units $320_1 \ldots 320_9$ comprises one or more sensors for sensing one or more physical parameters (e.g., temperature, pressure, chemical concentration, electromagnetic radiation level such as light intensity or hard radiation level, vibration level, etc.) and/or other physical activity (e.g., motion of a person or object) around that sensor unit and generating data indicative of these one or more physical parameters and/or other physical activity. For example, each of the sensor units $320_1 \ldots 320_5$ may comprise one or more of: temperature/heat sensors (e.g., to detect surrounding temperature); pressure sensors (e.g., to detect atmospheric pressure); chemical sensors (e.g., to sense concentrations or traces of chemicals, such as explosive substances); mass/weight sensors (e.g., to sense mass/weight of persons or objects); vibration sensors (e.g., to sense ground vibrations); movement sensors (e.g., to sense movement of persons or objects); sound sensors (e.g., to sense voices, mechanical sounds, sounds from movement); visible light sensors (e.g., to sense visible light intensity) infrared light sensors (e.g., to sense infrared light emitted by persons or objects or effect video surveillance); RF sensors (e.g., to sense RF emissions or interference); hard radiation sensors (e.g., to sense x-rays, gamma rays or other hard radiation to effect Geiger counter/detection of nuclear decay, hidden object sensing); biotoxin sensors (e.g., to sense airborne or surface toxins, bacteria or viruses); cameras (e.g., to detect movement or identify person or objects, for instance, to effect video surveillance or provide imagery of a nearby patient to remote clinicians at the healthcare facility 33); liquid sensors (e.g., to sense presence of water or other liquids); and gas/vapor sensors (e.g., to sense presence of hazardous or harmful gases such as $H_2S$, CO, methane or propane, and/or hazardous or harmful vapors or gases such as chlorine, fluorine, bromine or petroleum vapors; to sense inadequate levels of oxygen, or presence of smoke or combustion products; etc). These examples are presented for illustrative purposes only as each of the sensor units $320_1 \ldots 320_9$ may comprise physical sensors with various other sensing capabilities.

The wireless pack interface 330 enables the ECAS outstation $28_j$ to wirelessly communicate with those packs $22_1 \ldots 22_N, 26_1 \ldots 26_R, 24_1 \ldots 24_P$ that are within its range. To that end, the wireless pack interface 330 comprises a wireless receiver to receive wireless signals transmitted by some of the packs $22_1 \ldots 22_N, 26_1 \ldots 26_R, 24_1 \ldots 24_P$ and conveying data generated by these packs, such as data derived from wireless location signals received by their location receivers 43, 143, 243, data generated by their sensor units 48, 148, 248, and/or data derived from input made by the first responders $14_1 \ldots 14_N$ via the user interface 52 of their first responder packs. In addition, the wireless pack interface 330 comprises a wireless transmitter to transmit wireless signals conveying data destined for some of the packs $22_1 \ldots 22_N, 26_1 \ldots 26_R, 24_1 \ldots 24_P$, such as data indicative of information to be presented to the first responders $14_1 \ldots 14_N$ via the user interface 52 of their first responder packs (e.g., information regarding actions to be performed, such as administering certain medical treatment to one or more of the patients $18_1 \ldots 18_P$, transporting one or more of the patients $18_1 \ldots 18_P$ to a given healthcare facility, moving himself/herself or one or more of the patients $18_1 \ldots 18_P$ to a different location, etc.) and/or data indicative of commands to be executed by those packs (e.g., commands to activate/deactivate their location receivers 43, 143, 243 and/or one or more sensors of their sensor units 48, 148, 248).

The wireless ECAS interface 340 enables the ECAS outstation $28_j$ to wirelessly communicate with the ECAS 30 over the wireless communication link 32, which, for instance, may be implemented by a dedicated emergency services link or a publicly available link. More particularly, the wireless ECAS interface 340 comprises a wireless transmitter to transmit to the ECAS 30 wireless signals conveying data for processing at the ECAS 30, such as: data derived from wireless location signals received by the location receivers 43, 143, 243, 303 (e.g., data related to time of arrivals of these signals) to establish locations of some of the packs $22_1 \ldots 22_N, 26_1 \ldots 26_R, 24_1 \ldots 24_P$; data generated by the sensor units 48, 148, 248 of these packs and by the sensor units $320_1 \ldots 320_9$ of the ECAS outstation $28_j$; and/or data derived from input made by the first responders $14_1 \ldots 14_N$ via the user interface 52 of their first responder packs. The wireless ECAS interface 340 also comprises a wireless receiver to receive wireless signals from the ECAS 30 and conveying data for use locally at the incident scene 12, such as data indicative of information to be presented to some of the first responders $14_1 \ldots 14_N$ via the user interface 52 of their first responder packs (e.g., information regarding actions to be performed, such as administering certain medical treatment to one or more of the patients $18_1 \ldots 18_P$, transporting one or more of the patients $18_1 \ldots 18_P$ to a given healthcare facility, moving himself/herself or one or more of the patients $18_1 \ldots 18_P$ to a different location, etc.) and/or data conveying commands to be executed by some of the packs $22_1 \ldots 22_N, 26_1 \ldots 26_R, 24_1 \ldots 24_P$ (e.g., commands to activate/deactivate their location receivers 43, 143, 243 and/or one or more sensors of their sensor units 48, 148, 248).

While in this embodiment each of the ECAS outstations $28_1 \ldots 28_M$ communicates with the ECAS 30 via the wireless communication link 32, in other embodiments, one or more of these ECAS outstations may communicate with the ECAS 30 via a communication link that is entirely wired or that is partly wired and partly wireless (e.g., established over one or more of a fiber optic metropolitan network or other wired network, a WiMax, cellular or other wireless network, or an emergency band connection).

The processing entity 360 performs various processing operations to implement functionality of the ECAS outstation $28_j$. These processing operations include operations to cause the wireless ECAS interface 340 to transmit wireless signals to the ECAS 30 based on wireless signals received by the ECAS outstation $28_j$ from individual ones of packs $22_1 \ldots 22_N, 26_1 \ldots 26_R, 24_1 \ldots 24_P$. As further discussed below, the ECAS 30 processes data derived from the wireless signals it receives from the ECAS outstation $28_j$ (possibly in conjunction with data derived from wireless signals it receives from other ones of the ECAS outstations $28_1 \ldots 28_M$) in order to determine one or more actions to be taken with respect to the first response mission.

In this embodiment, the processing entity 360 relays to the ECAS 30 data it derives from wireless signals it receives from the individual ones of the packs $22_1 \ldots 22_N$, $26_1 \ldots 26_R$, $24_1 \ldots 24_P$. This data may include data derived from wireless location signals received by the location receivers 43, 143, 243, 303 (e.g., data related to time of arrivals of these signals) to establish locations of some of the packs $22_1 \ldots 22_N$, $26_1 \ldots 26_R$, $24_1 \ldots 24_P$; data generated by the sensor units 48, 148, 248 of these packs and by the sensor units $320_1 \ldots 320_9$ of the ECAS outstation $28_j$; and/or data derived from input made by the first responders $14_1 \ldots 14_N$ via the user interface 52 of their first responder packs. That is, in this embodiment, the ECAS outstation $28_j$ acts as a data collection and relay point whereby the processing entity 360 performs relatively simple processing operations to collect data derived from wireless signals transmitted by individual ones of the packs $22_1 \ldots 22_N$, $26_1 \ldots 26_R$, $24_1 \ldots 24_P$, possibly formats the collected data, and relay the collected (and possibly formatted) data to the ECAS 30 where it is more extensively processed. In other embodiments, the processing entity 360 may perform more extensive processing operations. For example, in some embodiments, the processing entity 360 may locally perform location computations based on data related to time of arrivals of wireless location signals at location receivers 43, 143, 243, 303 of individual ones of packs $22_1 \ldots 22_N$, $26_1 \ldots 26_R$, $24_1 \ldots 24_P$ and the ECAS outstation $28_j$ to generate location data indicating the locations of these packs and may transmit wireless signals conveying the generated location data to the ECAS 30.

In addition, the processing operations performed by the processing entity 360 include operations to cause the wireless pack interface 330 to transmit wireless signals conveying data destined for individual ones of the packs $22_1 \ldots 22_N$, $26_1 \ldots 26_R$, $24_1 \ldots 24_P$, such as data indicative of information to be presented to first responders via the user interface 52 of these first responder packs and/or data indicative of commands to be executed by these packs, on a basis of wireless signals from the ECAS 30. As further discussed below, such wireless signals received from the ECAS 30 may have been transmitted by the ECAS 30 upon determining one or more actions to be taken with respect to the first response mission.

The processing entity 360 comprises one or more processors to perform its various processing operations. A given one of these one or more processors may be a general-purpose processor having access to a storage medium (e.g., semiconductor memory, including one or more ROM and/or RAM memory devices) storing program code for execution by that processor to implement the relevant processing operations. Alternatively, a given one of these one or more processors may be a specific-purpose processor comprising one or more pre-programmed hardware or firmware elements (e.g., ASICs, EEPROMs, etc.) or other related elements to implement the relevant processing operations.

The power supply 370 comprises one or more batteries and/or other power generation elements to supply power to the various components of the ECAS outstation $28_j$. The power supply 370 has a power capacity sufficient to enable the ECAS outstation $28_j$ to be used for purposes of the first response mission at the incident scene 12. The power supply 370 may also have charging circuitry to facilitate its recharging.

While in this embodiment the ECAS outstation $28_j$ comprises various components, in other embodiments, it may not comprise all of these components and/or may comprise different components.

ECAS 30

Figure 6:
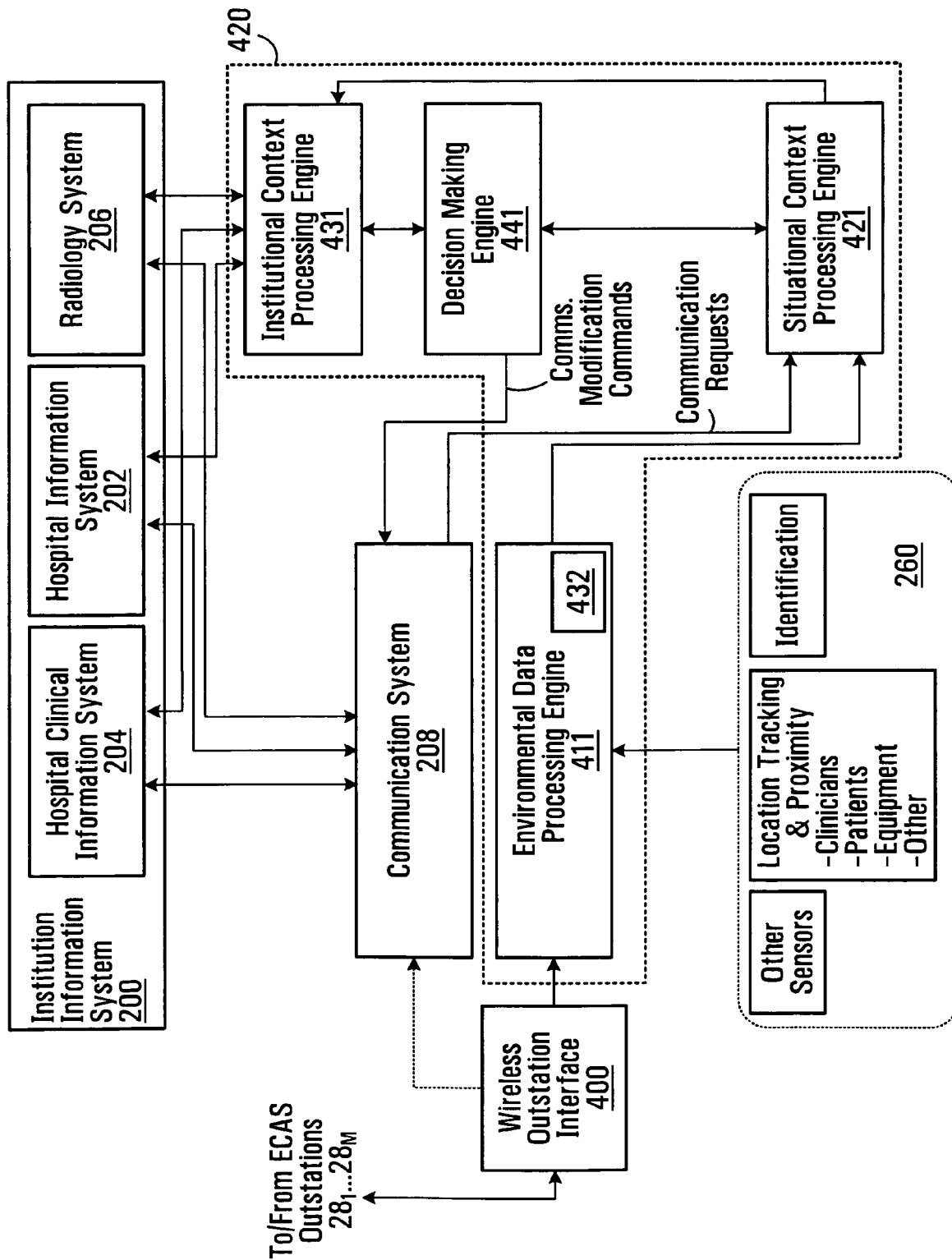
FIG. 6 shows components of a healthcare facility that includes an environment- and context-aware system of the first response support system, in accordance with an embodiment of the invention.

FIG. 6 shows an embodiment of the ECAS 30, which, in this embodiment, is located at the healthcare facility 33 remote from the incident scene 12.

The ECAS 30 comprises a processing entity 420 having access to a sensor system 260, a communication system 208 and an institutional information system 200 of the healthcare facility 33 in order to provide various services within the healthcare facility 33. In accordance with an embodiment of the invention, the processing entity 420 of the ECAS 30 also utilizes a wireless outstation interface 400 linked to the ECAS outstations $28_1 \ldots 28_M$ at the incident scene 12 via the wireless communication links 32 in order to provide various services in relation to the first response mission at the incident scene 12.

Generally speaking, the ECAS 30 uses location data, physical environment data and communication data derived from the sensor system 260, the communication system 208 and the wireless outstation interface 400 (i.e., from the ECAS outstations $28_1 \ldots 28_M$ at the incident scene 12) as well as institutional data from the institutional information system 20 such as policies, guidelines, user lists and profiles, etc., in order to render significant and useful decisions concerning services provided within the healthcare facility 33 or in relation to the first response mission at the incident scene 12. Specifically, the ECAS 30 enables decisions to be made regarding what actions should be taken that are consistent with a particular service, when certain "situations" are deemed to occur, based on data relating to the particular service that is derived from the sensor system 260, the communication system 208 and/or the wireless outstation interface 400.

The decisions taken by the ECAS 30 can result in adaptation or optimization of communications taking place in the communication system 208 and/or involving the first responders $14_1 \ldots 14_N$ at the incident scene 12, which may or may not be to such an extent as to enable improved, enhanced or even new clinical workflows and processes to result. This may mean preferentially feeding appropriate information to an authenticated user (including information determined to be relevant to the user's situation), preventing communications to an inappropriate user, adapting communications to the circumstances of the user or the user's equipment, establishing machine-to-machine communication with unattended equipment, initiating communications when certain circumstances arise, and so on.

In this manner, the ECAS 30 can provide adaptive, smart communications, based upon environmental awareness on plural environment-planes (including a location plane and a physical environment plane) and deduced situations, as well as access to permissions and authorization/authentication profiles, policy databases and other institutional information. Thus, services can be provided that adapt to the actual communications needs of users, such as clinicians at the healthcare facility 33 and the first responders $14_1 \ldots 14_N$ at the incident scene 12, taking into account both an environment in which they operate and their clinical workflow state.

An understanding of application of an ECAS such as the ECAS 30 to a healthcare facility such as the healthcare facility 33, as well as details regarding services that can be provided within the healthcare facility, can be obtained by consulting U.S. patent application Ser. No. 12/003,206 entitled "METHODS AND SYSTEMS FOR USE IN THE PROVI- SION OF SERVICES IN AN INSTITUTIONAL SETTING SUCH AS A HEALTHCARE FACILITY", filed on Dec. 20, 2007 by Graves et al., and hereby incorporated by reference herein.

In accordance with an embodiment of the invention, the ECAS outstations $28_1 \ldots 28_M$ in cooperation with the packs $22_1 \ldots 22_N$, $26_1 \ldots 26_R$, $24_1 \ldots 24_P$ enable capabilities of the ECAS 30 to be extended into the first response area at the incident scene 12. This allows the ECAS 30 to provide services relevant to the first response mission at the incident scene 12 (some of which being analogous to services provided within the healthcare facility 33, while others are specific to first response scenarios), thereby optimizing communications involving the first responders $14_1 \ldots 14_N$ and increasing first responder effectiveness, quality of care to patients, patient/first responder safety, speed of processing and overall first response site safety.

The aforementioned components of the ECAS 30, as well as examples of services which can be provided by the ECAS 30, will now be discussed in greater detail.

a) Institutional Information System 200

The institutional information system 200 manages institutional information pertaining to the healthcare facility 33. More particularly, in this embodiment, the institutional information system 200 comprises a healthcare information system (HIS) 202, a healthcare clinical information system (HCIS) 204, and a radiology system 206.

The HIS 202 may comprise databases for storing a variety of data, examples of which include general institution data, such as financial data, building maintenance schedules, and so on. The HIS 202 may also comprise databases for storing information about which clinicians (i.e., doctors, nurses, first responders and other medical professionals) are accredited, what their rights and privileges are, their work schedule and preferences (including their IT preferences), etc. The databases in the HIS 202 may also contain information about other healthcare facility support staff, such as orderlies, maintenance staff, administrative staff, or biomedical engineers. The databases in the HIS 202 may also contain information about visiting clinicians who have approval to work in the healthcare facility 33, yet are not formally part of the facility's staff. In that sense, the databases in the HIS 202 can contain information on dynamic/interim users, data, rights and privileges, as well as more formal and more permanent users, data, rights and privileges. The databases in the HIS 202 do not contain clinical information about a patient base of the healthcare facility 33 although they may contain non-clinical data about the patient base.

The HCIS 204 may include: a healthcare clinical information system (HCIS) core, which links and supports clinical databases of multiple departments and databases; departmental systems, many of which may have been acquired as stand-alone functions and may have had to have been subsequently integrated together; local Electronic Health Records (EHRs—or Electronic Patient Records (EPRs)) for patients in the healthcare facility 33 or who have been treated by the healthcare facility 33; test laboratory IT systems and databases with their different functions, modalities and outputs; firewalled secure gateways out to other locations for connectivity to centralized business continuity/disaster recovery (BC/DR), remote centralized EHR, etc.

The HIS 202 and the HCIS 204 may thus comprise databases for storing a variety of data, examples of which include: policies (which define actions to be taken under various situations and for various services in order to achieve desired results); lists of entities (such as doctors, nurses, medical equipment) and associated IDs and AAA information; patient medical status; patient test data; patient schedule data; patient-clinician association data; EHR data; EPR data; EMR data (clinical-based applications); ordered patient treatment data; diagnosis data; prognosis data; staff skills lists; and duty rosters.

These examples of data that may be stored in the HIS 202 and the HCIS 204 are presented for illustrative purposes only as various other data may be stored in these systems. For example, the databases in the HIS 202 and the HCIS 204 may also store policies which describe minimal and optimal combinations of resources (including people, machines, data, network, etc.) to perform certain functions. For instance, the formation of a "Code Blue" team requires certain clinicians and equipment to be reserved within a severely limited time to try and save a patient's life. Other "code names" have their own requirements as well as other processes. It should be appreciated that although the "code names" vary between clinical jurisdictions, a healthcare facility's underlying need for the associated services does not. The names used here are those used as of 2005 in the Doctors Hospital, Columbus, Ohio.

The radiology system 206 comprises a suite of non-visible light imaging modalities, such as X-ray, Magnetic Resonance Imaging (MRI), Computed Tomography (CT) scan, Positron Emission Tomography (PET)-scan as well as a Radiology Information System (RIS) which may include a Picture Archiving and Communication System (PACS) to move imaging data between modalities and diagnostic terminals and radiologists as well as archiving and accessing information stored in a radiology information database.

b) Communication System 208

The communication system 208 provides communication capabilities throughout the healthcare facility 33. For example, this can be achieved by one or more of the following communication networks:

voice network;

data network;

converged multimedia network: may use VoIP soft switches to provide voice services, which in turn provides more opportunity for communication sessions via SIP;

regional and metro networks: many healthcare facilities are geographically diverse or operate on multiple campuses or have regional operating entities or fall under common administration. Thus, there can be an inter-institutional metropolitan network, which may consist of high-capacity fiber links between healthcare facilities and data centers, for the purposes of data storage, PACS and health records systems, disaster recovery, voice communications, etc. The metropolitan network also allows the healthcare facilities to communicate with EMS and city services;

video conferencing and telemedicine network: a specialized infrastructure may exist to support video conferencing and telemedicine systems requiring higher resolution and/or time-sensitive performance;

wireless network: an example of a wireless local area network (WLAN) for voice and data point-of care applications. WLAN-capable user equipment integrate with, for example, nurse call systems which send informative text to the WLAN-capable user equipment as the nurse is being called. Other examples include cell phones or smart phones, which can be used for scheduling and contact in the WLAN;

legacy paging system;

equipment monitoring network: some equipment uses legacy 802.11 standards for point-to-point communications (e.g. wireless EKG monitors). Equipment such as infusion pumps may or may not contain an 802.11 WLAN communications capability; and clinical and virtual private network (VPN) access: satellite clinics access the HIS 202 and HCIS 204 via T1, digital subscriber line (DSL), or VPN. For remote clinicians, such as outpatient nurses, personal VPN access over the cellular data network can be used.

These examples of networks which may enable the communication system 208 to provide communication capabilities throughout the healthcare facility 33 are presented for illustrative purposes only as various other networks may be used to provide such communication capabilities.

c) Sensor System 260

The sensor system 260 senses and collects data primitives about various environment planes (including a location plane, a physical environment plane that takes into account heat/temperature, humidity, light, radiation, presence of specific gases or compounds, physical states such as door openings and other physical aspects of the environment, and a physiological plane in respect of patients within the healthcare facility 33) and filters or otherwise pre-processes these data primitives to a point where they can be fed to the processing entity 420.

To that end, the sensor system 260 comprises various sensors distributed throughout the healthcare facility 33 to provide a sensory awareness in multiple environment planes within the healthcare facility 33, such as location and/or movement of people and objects, physical parameters (e.g., temperature, pressure, radiation level, chemical concentrations, etc.) in the healthcare facility 33, physiological parameters (e.g., heart rate, blood pressure, toxin levels) of patients in the healthcare facility 33, etc. For example, the sensor system 260 may comprise one or more of:

location sensors (with reception and possibly transmission capabilities): absolute location or relative location (e.g., proximity sensors), active and passive;

cameras: movement detection and object identification using picture and video or processed derivations of components therein;

clinical sensors including stand-alone, on-body, in-body (ingestible or implanted) and on-equipment sensors;

sound sensors: voices, mechanical sounds, sounds from movement;

vibration sensors: fence vibrations, ground vibrations from intrude inadvertent interaction;

movement sensors: motion sensors, contact openings, closings, e.g., on gates, doors, entry points;

visible light sensors: video surveillance (manual or automatic analysis), photobeam disruption;

infra-red light sensors: video surveillance (manual or automatic analysis), photobeam disruption, changes in reflected energy, self-radiation (hot persons, objects);

wireless signals: interaction of objects, personnel with RF fields (quasi-radar or interferometric), active RF emissions (inadvertent/clandestine or deliberate/IFF);

mass/weight/pressure sensors: ground perimeter pressure sensors for personnel, objects with significant mass, matching mass to expected mass;

chemical sensors: chemical trace analysis, explosives detection;

biotoxin sensors: airborne, surface bacteria, virus sensing;

hard radiation sensors: Geiger counter/detection of nuclear decay, hidden object sensing (X-ray, nuclear scanners);

liquids/fluids/water sensors: fluid sensors/floats, humidity sensing; and gas/vapor sensors: hazardous gas detection (e.g., $H_2S$ sensor, CO sensor or sensors for more problematic gases).

These examples of sensors are presented for illustrative purposes only as the sensor system 260 may comprise various other types of sensors to sense various aspects of the healthcare facility 33. Also, some of these or other sensors may be accompanied by complementary actuators (e.g., door position sensors may be accompanied by door lock actuators).

At the incident scene 12, the sensor units and location units of the packs $22_1 \ldots 22_N$, $26_1 \ldots 26_R$, $24_1 \ldots 24_P$ and the ECAS outstations $28_1 \ldots 28_M$ as well as the processing entities 360 of the ECAS outstations $28_1 \ldots 28_M$ can collaborate to implement functionality similar to a distributed version of the functionality of the sensor system 260 of the healthcare facility 33.

d) Wireless Outstation Interface 400

The wireless outstation interface 400 enables the ECAS 30 to wirelessly communicate with the ECAS outstations $28_1 \ldots 28_M$ over the wireless communication links 32, either directly or via an interposed network which may be wireless or wired (e.g., a fiber optic metropolitan network or other wired network, a WiMax, cellular or other wireless network, or an emergency band connection).

More particularly, in this embodiment, the wireless outstation interface 400 comprises a wireless receiver to receive wireless signals transmitted by the ECAS outstations $28_1 \ldots 28_M$ and conveying data regarding the incident scene 12, such as data derived from wireless location signals received by the location receivers 43, 143, 243, 303 (e.g., data related to time of arrivals of these signals) to establish locations of the packs $22_1 \ldots 22_N$, $26_1 \ldots 26_R$, $24_1 \ldots 24_P$; data generated by the sensor units 48, 148, 248 of these packs and by the sensor units $320_1 \ldots 320_9$ of the ECAS outstations $28_1 \ldots 28_M$; and/or data derived from input made by the first responders $14_1 \ldots 14_N$ via the user interface 52 of their first responder packs. The wireless ECAS interface 340 also comprises a wireless transmitter to transmit wireless signals destined for the ECAS outstations $28_1 \ldots 28_M$ and conveying data for use at the incident scene 12, such as data indicative of information to be presented to the first responders $14_1 \ldots 14_N$ via the user interface 52 of their first responder packs (e.g., information regarding actions to be performed, such as administering certain medical treatment to one or more of the patients $18_1 \ldots 18_P$, transporting one or more of the patients $18_1 \ldots 18_P$ to a given healthcare facility, moving himself/herself or one or more of the patients $18_1 \ldots 18_P$ to a different location, etc.) and/or data conveying commands to be executed by the packs $22_1 \ldots 22_N$, $26_1 \ldots 26_R$, $24_1 \ldots 24_P$ (e.g., commands to activate/deactivate their location receivers 43, 143, 243 and/or one or more sensors of their sensor units 48, 148, 248).

In other embodiments, such as those where the ECAS 30 interfaces to a wired network feeding a local wireless drop to the ECAS outstations $28_1 \ldots 28_M$, the wireless outstation interface 400 may be replaced by an equivalent wired network access interface.

e) Processing Entity 420

Through interaction with the sensor system 260, the communication system 208, the wireless outstation interface 400 and the institutional information system 200, the processing entity 420 of the ECAS 30 provides various services within the healthcare facility 33 and, in accordance with an embodiment of the invention, various services in relation to first response missions such as the first response mission at the incident scene 12.

Figure 7A:
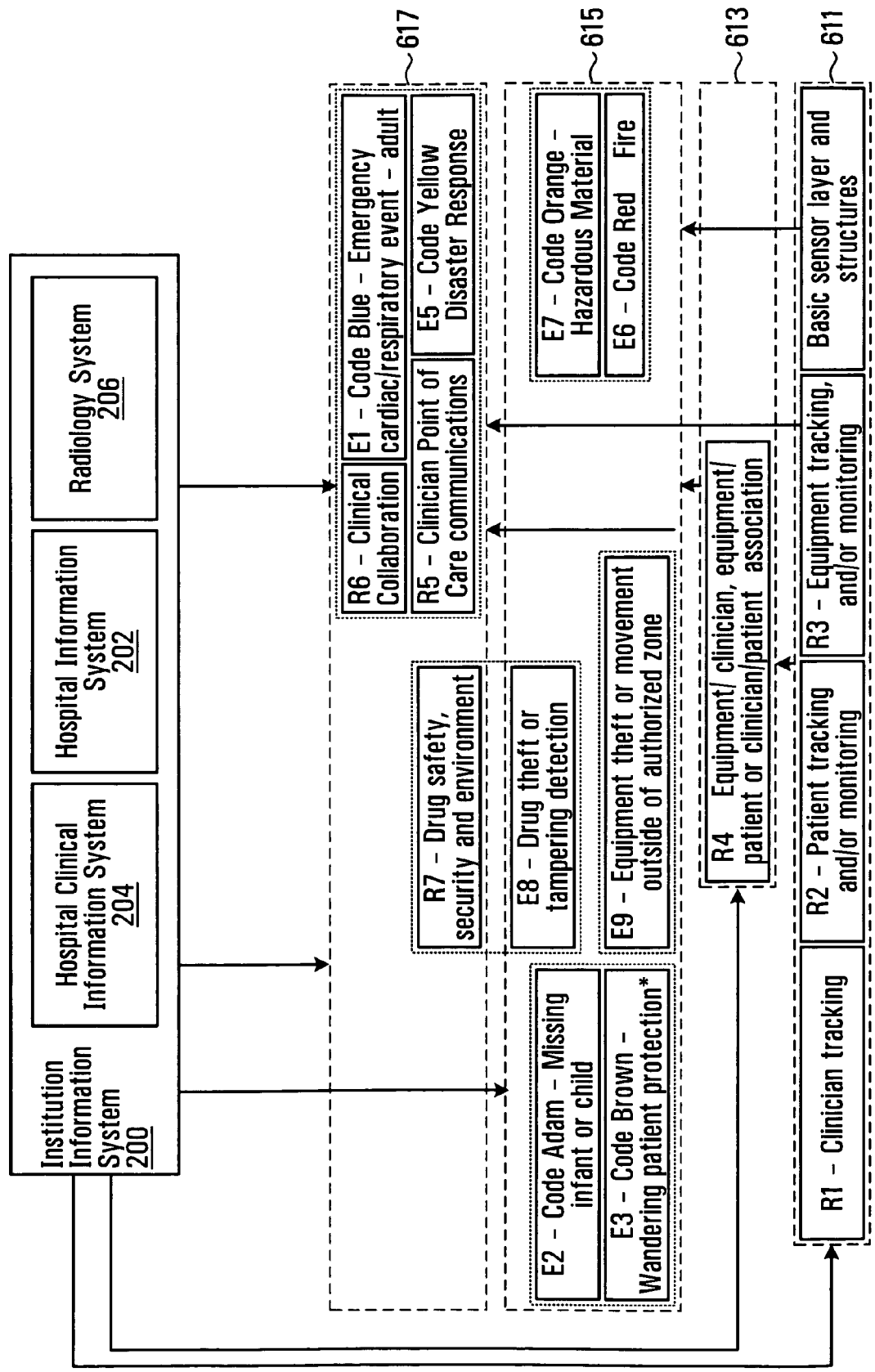
FIG. 7A shows services that can be provided within the healthcare facility by the environment- and context-aware system, in accordance with an embodiment of the invention.

FIG. 7A shows examples of services that can be provided by the ECAS 30 within the healthcare facility 33, including:

- a "clinician tracking" service: tracks the locations of clinicians, such as doctors, nurses and other clinicians within the healthcare facility 33;
- a "patient tracking and/or monitoring" service; tracks the locations and/or monitors the conditions of patients within the healthcare facility 33;
- an "equipment tracking and/or monitoring" service; tracks the locations and/or monitors the conditions of equipment within the healthcare facility 33;
- an "equipment/clinician, equipment/patient or clinician patient association" service: monitors associations between clinicians, patients and equipment at the healthcare facility 33;
- a "clinician point of care communications" service: implements tools enabling clinicians to access information and perform clinical tasks (e.g., decisions, treatment orders, etc.) at the point of care of patients within the healthcare facility 33);
- a "clinical collaboration" service: implements tools enabling collaboration between clinicians at the healthcare facility 33;
- a "code blue/pink—emergency cardiac/respiratory event—adult/pediatric" service: performs various actions, including identification and location of the code blue/pink event and victim and communication to form a code blue/pink team within the healthcare facility 33;
- a "code Adam—missing infant or child" service: acts to prevent abduction or loss of infants within the healthcare facility 33 (e.g., by tracking them) and to find a missing infant when he/she goes missing (e.g., by issuing alerts);
- a "code brown—wandering patient protection" service: acts to prevent wandering of patients within the healthcare facility 33 (e.g., by tracking them) and to find a missing patient when he/she goes missing (e.g., by issuing alerts);
- a "code yellow—disaster response" service: performs actions to prepare the healthcare facility 33 for incoming casualties, including communications to form the code yellow team, and to support the code yellow team during initial treatment of incoming casualties;
- a "code red—fire" service: detects, assesses and tracks a fire at the healthcare facility 33 or remote therefrom (e.g., at the incident scene 12) and issues communications to respond to the fire (e.g., alerts, areas and directions to evacuate, commands to close doors, control ventilation, validate via the location sensing system that all locatable clinicians, staff and patients are evacuated from evacuation areas, identification of the location of locatable hazardous or inflammable material relative to the fire);
- a "code orange—hazardous material" service: detects, assesses and tracks hazardous material at the healthcare facility 33 or remote therefrom (e.g., at the incident scene 12) and issues communications to respond to the hazardous material (e.g., alerts, areas and directions to evacuate, commands to close doors, control ventilation, validate via the location sensing system that all locatable clinicians, staff and patients are evacuated from evacuation areas);
- a "drug safety, security and environment" service: tracks drugs within the healthcare facility 33 or remote therefrom (e.g., at the incident scene 12), manages their inventory and protects them from being misplaced, stolen or exposed to harmful environmental conditions; and
- an "equipment theft or movement outside of authorized zone—detection" service; detects theft or unauthorized movement of equipment within the healthcare facility 33 and/or remote therefrom (e.g., the drop packs $26_1 \ldots 26_R$ at the incident scene 12).

Figure 7B:
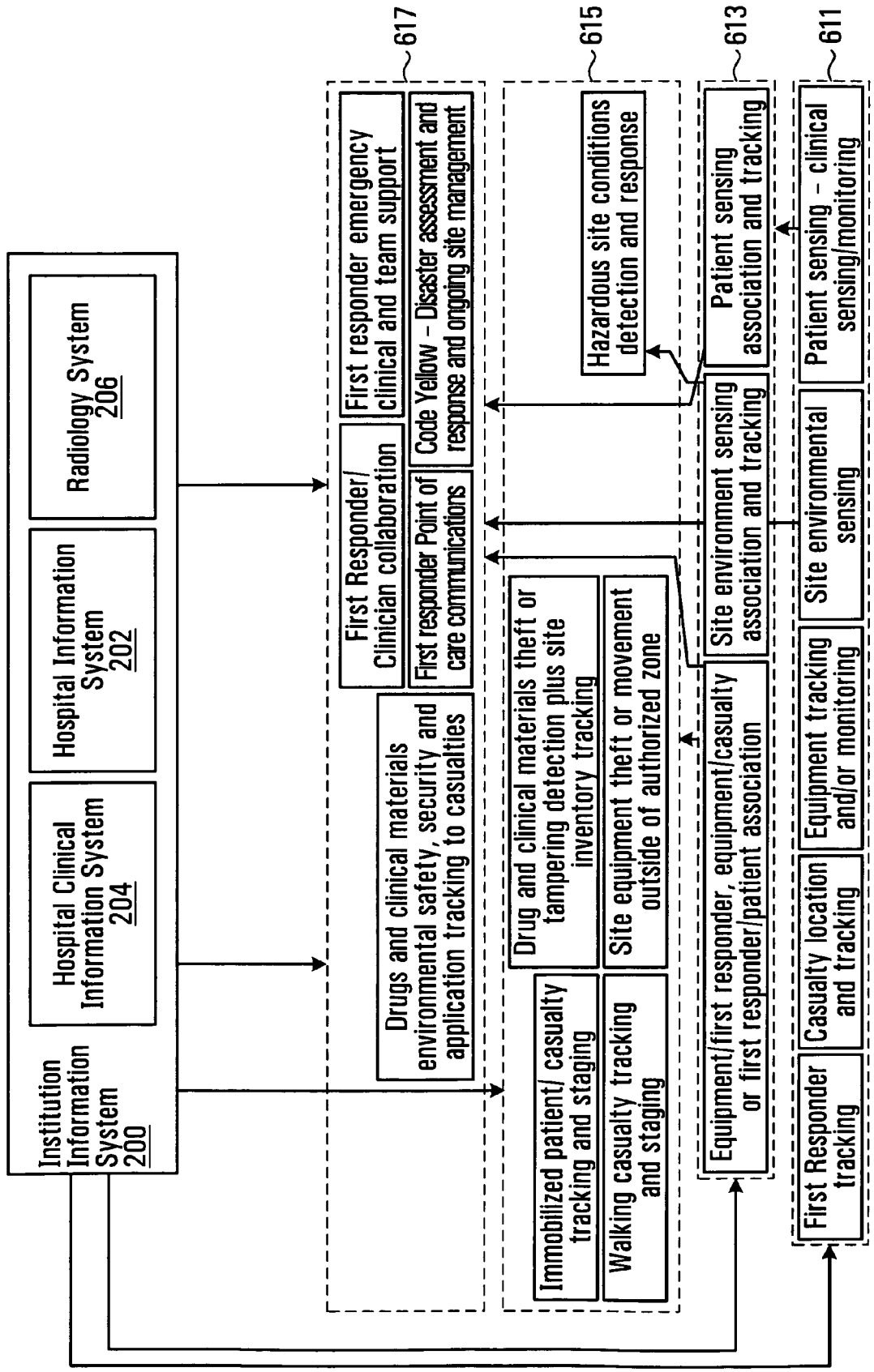
FIG. 7B shows services that can be provided in support of the first response mission by the environment- and context-aware system, in accordance with an embodiment of the invention.

For its part, FIG. 7B shows examples of services that can be provided by the ECAS 30 in support of first response missions such as the first response mission at the incident scene 12, in accordance with an embodiment of the invention. These "first response support" services include:

- a "first responder location and tracking" service: tracks the locations of the first responders $14_1 \ldots 14_N$ at the incident scene 12;
- a "patient location and tracking" service: tracks the locations of the patients $18_1 \ldots 18_P$ at the incident scene 12;
- an "equipment tracking and/or monitoring" service: tracks the locations and/or monitors the conditions of equipment (e.g., field medical equipment and the drop packs $26_1 \ldots 26_R$) at the incident scene 12;
- a "site environmental sensing" service: collects information about environmental conditions at the incident scene 12 from the sensor units 48, 148, 248 of the packs $22_1 \ldots 22_N, 26_1 \ldots 26_R, 24_1 \ldots 24_P$ and the sensor units $320_1 \ldots 320_9$ of the ECAS outstations $28_1 \ldots 28_M$;
- a "patient medical sensing" service: collects data about patient conditions from the medical sensors of the sensor units 148 associated with the patients $18_1 \ldots 18_P$ at the incident scene 12;
- an "equipment/first responder, equipment/patient or first responder/patient association" service: monitors associations between the first responders $14_1 \ldots 14_N$, the patients $18_1 \ldots 18_P$ and equipment (e.g., the packs $22_1 \ldots 22_N, 26_1 \ldots 26_R, 24_1 \ldots 24_P$) at the incident scene 12;
- a "site environmental sensing association and tracking" service: observes data from the various sensing planes of the sensor units 48, 148, 248 of the packs $22_1 \ldots 22_N$, $26_1 \ldots 26_R, 24_1 \ldots 24_P$ and the sensor units $320_1 \ldots 320_9$ of the ECAS outstations $28_1 \ldots 28_M$, establishes the profiles on those planes, and looks for inter-plane associations that may be indicative of developing site condition issues for the incident scene 12;
- a "patient medical sensing association and tracking" service: correlates and tracks data derived from each patient's medical sensors (in its sensor unit 148) and identifies potential conditions needing clinical/first responder notification and/or treatment;
- an "immobilized patient tracking and staging" service: tracks at what stage each patient is at and maps it into required activities such as a reserved ambulance slot for transportation;
- a "walking patient" tracking and staging service: tracks where the patients $18_1 \ldots 18_P$ are on site, when they are mobile and may be wandering about, and maps them into appropriate transportation away from the incident scene 12 (e.g., via ambulance or otherwise);
- a "site equipment theft or movement outside of authorized zone" service: ensures that equipment (e.g., the packs $22_1 \ldots 22_N, 26_1 \ldots 26_R, 24_1 \ldots 24_P$) at the incident scene 12 does not "wander" without the first responders $14_1 \ldots 14_N$ being aware of it (e.g., due to legitimate use by other first responders or by theft by bystanders);
- a "drugs and similar clinical materials (e.g. blood plasma) theft, tampering detection plus site inventory tracking service": ensures that these are not stolen or tampered with so are safe to use and can be located when need and ensures that, if the incident scene 12 starts running short of specific supplies (e.g., blood plasma) more can be dispatched before they run out;

a "hazardous site conditions detection and response" service: examines outputs of the site environmental tracking service and the locations and numbers of patients and first responders and determines whether action needs to be taken (e.g., evacuate a specific area of the incident scene 12 first due to deteriorating conditions in that area);

a "drugs and clinical materials environmental safety, security and application tracking to casualties" service: ensures, through monitoring with sensors drugs and clinical materials at the incident scene 12, that these clinical supplies have not been spoiled by exposure to a harmful environment (e.g., excess heat) and are being used by approved personnel, and tracks which patients they are used on so as to provide a "history on demand" for each patient (e.g., helps to avoid problems such as two first responders dosing patients with morphine and hence giving them a morphine overdose);

a "first responder point of care/point of stabilization communications" service: implements tools enabling the first responders $14_1 \ldots 14_N$ to access information and perform clinical tasks (e.g., decisions, stabilizing treatment and transportation orders, etc.) at the point of first care of the patients $18_1 \ldots 18_P$ at the incident scene 12;

a "first responder/clinician collaboration" service (and its equivalent "first responder/first responder collaboration" service): implements tools enabling collaboration between the first responders $14_1 \ldots 14_N$ at the incident site 12 and clinicians at the healthcare facility 33 (or between different ones of the first responders $14_1 \ldots 14_N$);

a "first responder emergency clinical and team support" service: invoked by a first responder when faced with a patient who is in a critical declining condition beyond the first responder's skills or training or when other additional help is needed with a critical patient, forms a first response team to help from amongst other ones of the first responders $14_1 \ldots 14_N$ on-site and opens channels to high quality clinical support from the healthcare facility 33; and a "code yellow—disaster assessment and response and ongoing site management" service: looks at all clinical activities being performed by the first responders $14_1 \ldots 14_N$ and situations of the patients $18_1 \ldots 18_P$ and provides a view to the healthcare facility 33 of estimated support resources needed as the patients $18_1 \ldots 18_P$ are transported as well as helps to optimize deployment of first response personnel at the incident scene 12; in cases where it is clear that the first response personnel is overwhelmed, can trigger additional resources to be called in and, as the first response personnel complete their work, can release them and can check (via the patient packs $24_1 \ldots 24_P$) that all patients needing transportation have been transported).

As shown in FIGS. 7A and 7B, these and other services that can be provided by the ECAS 30 can be categorized into four distinct layers, namely a "basic environmental services" layer 611, an "associative and alerting environmental services" layer 613, a "non-clinical and clinical support services" layer 615, and a "clinical services" layer 617. Each of these service layers can have specific constraints and requirements. For instance, services in the clinical services layer 617 services can be subject to intense scrutiny (e.g., under the Health Insurance Portability and Accountability Act (HIPAA)) to ensure patient information safety and confidentiality is maintained.

In order to provide these services, the processing entity 420 of the ECAS 30 comprises suitable hardware and software (which may include firmware) for implementing a plurality of functional components, which, in this embodiment, include an environmental data processing engine 411, a situational context processing engine 421, an institutional context processing engine 431 and a decision making engine 441. Examples of such processing engines and their functionality, particularly in respect of the services provided in a healthcare facility such as the healthcare facility 33, can be obtained by consulting U.S. patent application Ser. No. 12/003,206 referenced previously herein.

Considering specifically the first response support services contemplated herein, and taking as an example the first response mission at the incident scene 12, the environmental data processing engine 411 processes data transmitted by the ECAS outstations $28_1 \ldots 28_M$ and received via the wireless outstation interface 400, such as data related to times of arrival of wireless location signals transmitted by the packs $22_1 \ldots 22_N$, $26_1 \ldots 26_R$, $24_1 \ldots 24_P$, data generated by the sensor units 48, 148, 248 of these packs, data generated by the sensor units $320_1 \ldots 320_9$ of these ECAS outstations, and/or data derived from input made by the first responders $14_1 \ldots 14_N$ via the user interface 52 of their first responder packs, in order to derive data indicative of an "environment" at the incident scene 12. This environment can be viewed as an aggregation of people, objects, conditions, and influences present at the incident scene 12. It can be observed along a plurality of environment planes, such as a location plane which considers locations of people and objects at the incident scene 12, a physical environment plane which considers heat/temperature, humidity, light, radiation, presence of specific gases or compounds, physical states such as door openings and other physical aspects of the environment at the incident scene 12, and a physiological plane which considers physiological/medical conditions of patients at the incident scene 12. Thus, the data indicative of the environment at the incident scene 12 that is derived by the environmental data processing engine 411 comprises data indicative of various aspects of the environment, such as: locations of the first responders $14_1 \ldots 14_N$, the patients $18_1 \ldots 18_P$, and the drop packs $26_1 \ldots 26_R$ at the incident scene 12; physical parameters such as temperature, pressure, chemical concentration, radiation level, etc., at the incident scene 12; and physiological parameters such as heart rate, body temperature, etc., of the patients $18_1 \ldots 18_P$ at the incident scene 12.

The situational context processing engine 421 processes the data indicative of the environment at the incident scene 12 to compare, correlate or otherwise consider different aspects of the environment (e.g., locational, physical, physiological aspects) and determine that one or more "situations" have occurred in relation to the first response mission at the incident scene 12. Each of these one or more situations is a set of circumstances surrounding an event or group of events, a previous history of that event/those events and any associated factors. Collectively, the one or more situations can be viewed as a "situational context" of the first response mission at the incident scene 12.

For example, the situational context processing engine 421 may: compare the locations of the first responders $14_1 \ldots 14_N$, the patients $18_1 \ldots 18_P$, and the drop packs $26_1 \ldots 26_R$ amongst one another (e.g., to detect that a first responder $14_i$ is next to a patient $18_i$ and infer from this proximity that the first responder $14_i$ is treating the patient $18_i$); track physical parameters sensed by the packs $22_1 \ldots 22_N$, $26_1 \ldots 26_R$, $24_1 \ldots 24_P$ over time (e.g., to detect a sudden increase in temperature around one of these packs or detect that a hazardous contaminant is spreading in a specific area at the incident scene 12); compare physiological parameters of the patients $18_1 \ldots 18_P$ sensed by their packs $24_1 \ldots 24_P$ at different times (e.g., to detect a significant drop in vital signs of a patient $18_j$); etc.

In determining the one or more situations deemed to have occurred, the situational context processing engine 421 may also process data other than the data indicative of the environment at the incident scene 12. For example, the situational context processing engine 421 may process data derived from the communication system 208 of the healthcare facility 33, such as data relating to communications made the first responders $14_1 \ldots 14_N$ using their packs $14_1 \ldots 14_N$ (e.g., reports about patients or conditions at the incident scene 12) and/or data relating to communications (e.g., telephonic communications, pages, sessions at computer terminals) involving clinicians at the healthcare facility 33. As another example, the situational context processing engine 421 may process data indicative of an environment at the healthcare facility 33 and derived by the environmental data processing engine 411, such as locations of clinicians and/or equipment within the healthcare facility 33.

Examples of situations that can be deemed to have occurred in relation to the first response mission are presented below. For now, suffice it to say that the situational context processing engine 421 outputs data indicative of the one or more situations deemed to have occurred, i.e., data indicative of the situational context of the first response mission.

The institutional context processing engine 431 consults the institutional information system 200 based on the data indicative of the one or more situations deemed to have occurred in order to provide to the decision making engine 441 institutional data relevant to these one or more situations. The institutional data can be viewed as data indicative of an "institutional context" that specifies, for example, what is allowable (e.g., policies), what resources are available (e.g., people, skills, duty roster, equipment list), what should normally happen (e.g., history) and/or how to proceed (e.g., procedures, rules, guidelines) in respect of the one or more situations. Examples of institutional data that can be provided by the institutional context processing engine 431 are presented below Based on the data indicative of the one or more situations deemed to have occurred (provided by the situational context processing engine 421) and the institutional data relevant to these one or more situations (provided by the institutional context processing engine 431), the decision making engine 441 determines one or more actions to be taken with respect to the first response mission in order to address these one or more situations.

For example, the decision making engine 441 may determine that one or more communication actions are to be taken to address the one or more situations, such as transmitting one or more messages to the first responders $14_1 \ldots 14_N$ at the incident scene 12 and/or clinicians at the healthcare facility 33, establishing a communication link between a first responder at the incident scene 12 and a clinician at the healthcare facility 33, etc. The decision making engine 441 can then command the communication system 208 to perform the one or more communication actions that are to be taken (e.g., send commands to the communication system 208 to transmit messages to the first responders $14_1 \ldots 14_N$, establish a communication link between a first responder at the incident scene 12 and a clinician at the healthcare facility 33, etc.).

Figure 8:
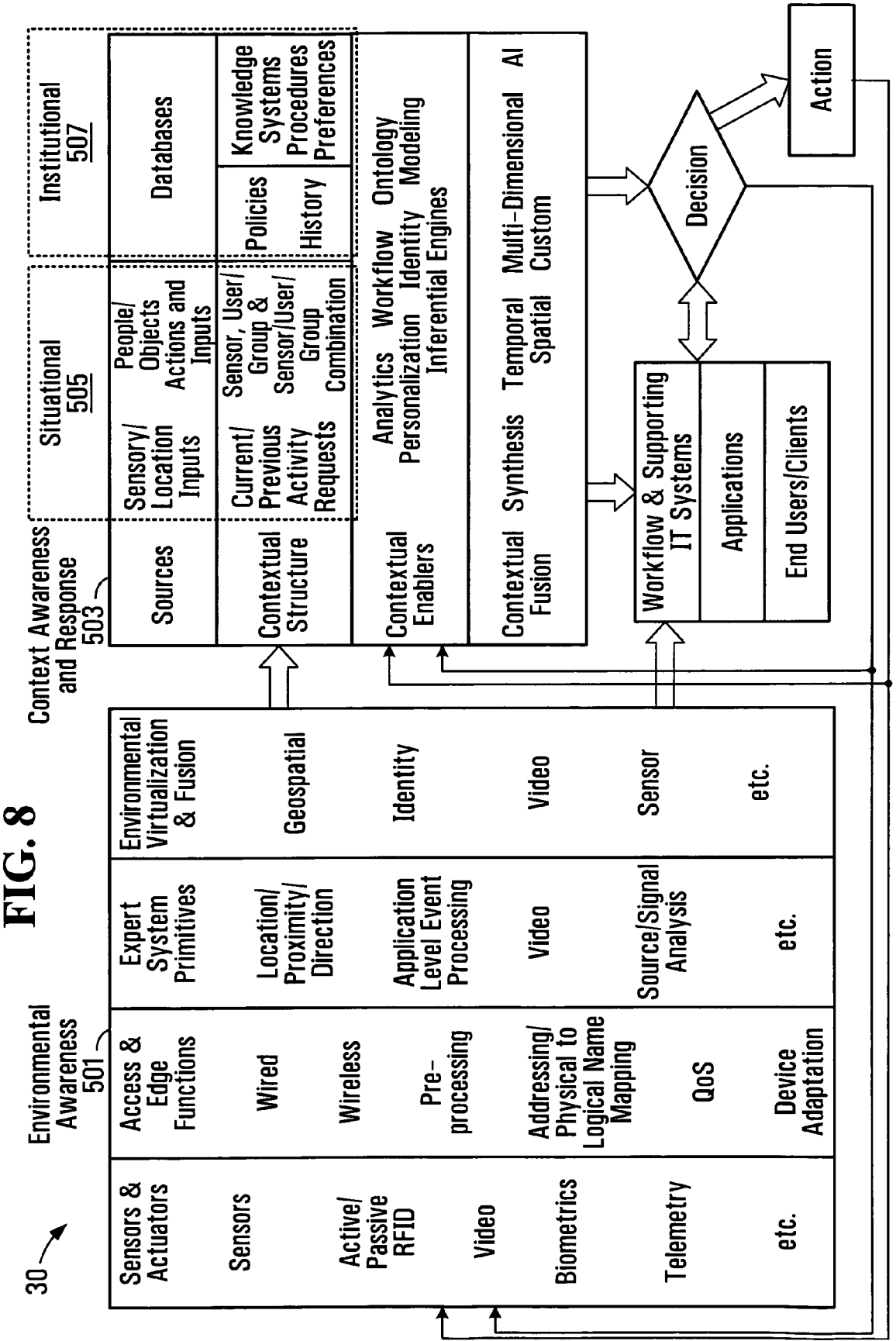
FIG. 8 shows at a high level an environmental awareness component and a contextual awareness and response component of the environment- and context-aware system, in accordance with an embodiment of the invention.

Thus, by virtue of its processing engines 411, 421, 431, the processing entity 420 of the ECAS 30 has both an environmental awareness and a contextual awareness that enables it to make relevant decisions and cause actions to be taken based on these decisions. This can be seen from FIG. 8, which provides a high level view of an "environmental awareness" component 501 and a "contextual awareness and response" component 503 of the processing entity 420 of the ECAS 30.

The environmental awareness component 501, which can be implemented by the environmental data processing engine 411, enables a comprehensive understanding of the environment in which a person or object is, by collecting data from various sensors and other devices (e.g., the packs $22_1 \ldots 22_N$, $26_1 \ldots 26_R$, $24_1 \ldots 24_P$), bringing this data to a point where data reduction can be applied, whereby it can be logically mapped and correlated and expert system primitives can be derived allowing the detection of various conditions (e.g. proximity of a first responder with his/her assigned patient) and data useful to the situational context processing engine 421 can be formulated. By collecting, aggregating, fusing, and virtualizing this information, a much deeper understanding can be created. This heightened environmental awareness is beneficial on its own merits as an independent functional block for use by other functional blocks and applications. It can also be useful to integrate the result of the environmental awareness component 501 into the contextual awareness and response component 503.

Specifically, the contextual awareness and response component 503 has two parts, namely a situational part 505, which can be implemented by the situational context processing engine 421, and an institutional part 507, which can be implemented by the institutional context processing engine 431. As mentioned above, situational context can be viewed as one or more situations deemed to have occurred in substantially real time, while institutional context can be viewed as the context of what the institution's or facility's policies, procedures and the like would indicate ought to be happening. As a whole, the contextual awareness and response component 503 takes raw information, databases, environmental awareness information and other types of "inputs" and melds this into situationally appropriate awareness and responses. To this end, the contextual awareness and response component 503 may implement contextual fusion (such as synthesis, artificial intelligence, spatial, temporal, multi-dimensional and customized fusion) based on contextual enablers (such as analytics, modeling, personalization, workflow, ontology, identity and inferential engines).

The combination of both environmental awareness (i.e., the environmental data processing engine 411) and contextual awareness and response (i.e., the situational context processing engine 421 and the institutional context processing engine 431), enables a comprehensive understanding of conditions and provides the ability to leverage that understanding to make decisions and take actions by a wide range of workflow and supporting IT systems, applications, and end users or their clients.

The environmental data processing engine 411, the situational context processing engine 421, the institutional context processing engine 431 and the decision making engine 441 may comprise one or more processors to perform their processing operations. A given one of these one or more processors may be a general-purpose processor having access to a storage medium (e.g., semiconductor memory, including one or more ROM and/or RAM memory devices) storing program code for execution by that processor to implement the relevant processing operations. Alternatively, a given one of these one or more processors may be a specific-purpose processor comprising one or more pre-programmed hardware or firmware elements (e.g., ASICs, EEPROMs, etc.) or other related elements to implement the relevant processing operations.

To illustrate how the environmental data processing engine 411, the situational context processing engine 421, the institutional context processing engine 431 and the decision making engine 441 can provide the first response support services contemplated herein, various examples of situations which can arise will now be considered.

EXAMPLE 1

By processing the data indicative of the environment at the incident scene 12 (i.e., location data, physical data, physiological data) produced by the environmental data processing engine 411, the situational context processing engine 421 determines that the following situation has occurred: vital signs of a patient $18_x$ have dropped significantly (based on physiological data from the patient pack $24_x$ of the patient $18_x$); none of the first responders $14_1 \ldots 14_N$ is currently treating the patient $18_x$ (based on their location); a first responder $14_k$ who initially treated the patient $18_x$ is now far away and treating another patient (based on their location and/or other determinants of the situational context, such as communications involving the first responder $14_k$ or a state of that other patient's patient pack); a first responder $14_y$ is close to the patient $18_x$ (based on their location); and the first responder $14_y$ is not currently treating any of the patients $18_1 \ldots 18_P$ (based on their location and/or other determinants of the situational context, such as communications involving the first responder $14_y$ or a lack of any current association between the first responder $14_y$ and any of the patients).

Based on the data indicative of this situation, the institutional context processing engine 431 consults the institutional information system 200 to obtain institutional data relevant to this situation. For instance, the institutional data may include: data indicating that immediate treatment needs to be administered to the patient $18_x$ (based on his/her vitals signs); data describing the required treatment; and data defining a skill set of the first responder $14_y$ (based on his/her identity).

The decision making engine 441 determines, on a basis of the data indicative of the situation and the institutional data relevant to the situation, that a message is to be sent to the first responder $14_y$ to indicate that the patient $18_x$ needs immediate treatment, convey the location of the patient $18_x$ (and/or directions thereto), and convey information on the required treatment to be administered. The decision making engine 441 causes the message to be transmitted to the first responder pack $22_y$ of the first responder $14_y$, via the communication system 208 and/or the wireless outstation interface 400.

In some cases, depending upon policies of the healthcare facility 33, a certain level of preference to have the first responder $14_k$ who initially treated the patient $18_x$ return or notified of actions performed by the first responder $14_y$ may be invoked for continuity of care reasons (e.g., to avoid "double dose of morphine" or other problems from uncoordinated treatments). This may also be managed through a medical file associated with the patient $18_x$, which may be made available to the first responder $14_k$ or any other authorized first responder approaching into a proximate relationship with the patient $18_x$ after being treated by the first responder $14_y$.

EXAMPLE 2

By processing the data indicative of the environment at the incident scene 12 produced by the environmental data processing engine 411 and by processing data relating to communications effected via the communication system 208, the situational context processing engine 421 determines that the following situation has occurred: a patient $18_y$ is currently being treated by a first responder $14_z$ (based on their location); and the first responder $14_z$ has requested treatment information for the patient $18_y$ using his/her first responder pack $22_z$, for example, by describing a physical condition or symptoms of the patient $18_y$ and requesting assistance from a doctor to determine what treatment to give.

Based on the data indicative of this situation, the institutional context processing engine 431 consults the institutional information system 200 to obtain institutional data relevant to this situation. For instance, the institutional data may include: data indicative that Dr. Smith is available (based on his schedule and communication status) and qualified (based on his skill set) to provide assistance to the first responder $14_z$.

The decision making engine 441 determines, on a basis of the data indicative of the situation and the institutional data relevant to the situation, that a message is to be sent to Dr. Smith to request his assistance and put him in contact with the first responder $14_z$ at the incident scene 12 to determine what treatment to give to the patient $18_y$.

The decision making engine 441 causes the message to be transmitted to Dr. Smith via the communication system 208. If and when Dr. Smith is reached, the decision making engine 441 may cause a communication link to be established between Dr. Smith and the first responder $14_z$ via the communication system 208 and the first responder pack $22_z$ of the first responder $14_z$. In some cases, this communication link may enable filtered shared viewing of information concerning the patient $18_y$ such as the on-site treatment records to date, vital signs and other physiological data history or the patient's HER, if available.

EXAMPLE 3

By processing the data indicative of the environment at the incident scene 12 produced by the environmental data processing engine 411 (and possibly by processing data relating to communications effected via the communication system 208), the situational context processing engine 421 determines that the following situation has occurred: twenty patients $18_1 \ldots 18_{20}$ at the incident scene 12 have low vital signs (based on physiological data from their patient packs $24_1 \ldots 24_{20}$ and possibly based on reports provided by the first responders $14_1 \ldots 14_N$ using their first responder packs $22_1 \ldots 22_N$).

Based on the data indicative of this situation, the institutional context processing engine 431 consults the institutional information system 200 to obtain institutional data relevant to this situation. For instance, the institutional data may include: data indicative that seventeen of the patients $24_1 \ldots 24_{20}$ need immediate transportation to an ER (based on their vital signs); data indicative that the ER of the healthcare facility 33 currently has a capacity to handle a maximum of ten additional patients (based on the current number of admitted patients and the available resources, such as doctors and nurses); and data indicative of another nearby healthcare facility to which patients may be transported.

The decision making engine 441 determines, on a basis of the data indicative of the situation and the institutional data relevant to the situation, that messages are to be sent to the first responders $14_1 \ldots 14_N$ to indicate that ten of the patients $18_1 \ldots 18_{20}$ who need immediate transportation are to be immediately transported to the ER of the healthcare facility 33 and that the other seven of these patients who need immediate transportation are to be transported to the other nearby healthcare facility. The decision making engine 441 causes the messages to be transmitted to the first responder packs $22_1 \ldots 22_N$ of the first responders $14_1 \ldots 14_N$, via the communication system 208 and/or the wireless outstation interface 400.

EXAMPLE 4

By processing the data indicative of the environment at the incident scene 12 produced by the environmental data processing engine 411, the situational context processing engine 421 determines that the following situation has occurred: concentration of a toxic gas (e.g., carbon monoxide) has increased significantly in a particular area at the incident scene 12 (based on physical data and location data from one or more of the drop packs $26_1 \ldots 26_R$); a first responder $14_x$ and a patient $18_z$ are located in that particular area (based on their location); no toxic gas has been sensed in other areas at the incident scene 12 (based on physical data and location data from one or more of the packs $26_1 \ldots 26_R$, $22_1 \ldots 22_N$, $24_1 \ldots 24_P$).

Based on the data indicative of this situation, the institutional context processing engine 431 consults the institutional information system 200 to obtain institutional data relevant to this situation. For instance, the institutional data may include data indicating that immediate evacuation from the given area is required (based on the concentration of the toxic gas).

The decision making engine 441 determines, on a basis of the data indicative of the situation and the institutional data relevant to the situation, that a message is to be sent to the first responder $14_x$ to indicate that he/she and the patient $18_z$ need to immediately move away from their current location and convey the location of the nearest safe area (and/or directions thereto). The decision making engine 441 causes the message to be transmitted to the first responder pack $22_x$ of the first responder $14_x$, via the communication system 208 and/or the wireless outstation interface 400.

EXAMPLE 5

By processing the data indicative of the environment at the incident scene 12 produced by the environmental data processing engine 411, the situational context processing engine 421 determines that the following situation has occurred: hazardous conditions (e.g., fire, toxic gas, intense structural vibrations) exist in a given area at the incident scene 12 (based on physical data and location data from one or more of the packs $26_1 \ldots 26_R$, $22_1 \ldots 22_N$, $24_1 \ldots 24_P$); two first responders $14_y$ and $14_z$ and a patient $18_z$ they are carrying are moving on a path that passes through that given area (based on their location and movement direction); no hazardous conditions have been sensed in other areas at the incident scene 12 (based on physical data and location data from one or more of the packs $26_1 \ldots 26_R$, $22_1 \ldots 22_N$, $24_1 \ldots 24_P$). In some embodiments, knowledge of the hazardous conditions in the given area at the incident scene 12 and of the lack of such hazardous conditions in the other areas at the incident 12 may be derived from pre-existing data sources (e.g., sensors, information systems) available at the incident scene 12 and to which the ECAS outstations $28_1 \ldots 28_M$ may be connected.

Based on the data indicative of this situation, the institutional context processing engine 431 consults the institutional information system 200 to obtain institutional data relevant to this situation. For instance, the institutional data may include data indicating that immediate evacuation from the given area is required (based on the detected hazardous conditions).

The decision making engine 441 determines, on a basis of the data indicative of the situation and the institutional data relevant to the situation, that a message is to be sent to the first responders $14_y$ and $14_z$ to indicate that they are to take an alternate path and to convey directions describing this alternate path. The decision making engine 441 causes the message to be transmitted to the first responder packs $22_y$ and $22_z$ of the first responders $14_y$ and $14_z$, via the communication system 208 and/or the wireless outstation interface 400.

These examples of situations which can arise and actions that can be taken are presented for illustrative purposes only as various other situations can arise and may be addressed by the ECAS 30.

It will thus be appreciated that the first response support system 10 facilitates the first response mission at the incident scene 12 in that it provides the first responders $14_1 \ldots 14_N$ with bidirectional communication capability, real-time support for their information needs, and knowledge about their environment as they stabilize and transport the patients $18_1 \ldots 18_P$ under what may be hazardous conditions. By acting on automated decisions based on data on the location and state of the patients $18_1 \ldots 18_P$ and the first responders $14_1 \ldots 14_N$ and their equipment, the efficiency of first response mission can be improved.

For example:

Data about the patients $18_1 \ldots 18_P$ may be uploaded to the healthcare facility 33 (and/or one or more other receiving healthcare facilities) and data to support their treatment and transportation may be downloaded to the first responder packs $14_1 \ldots 14_N$. Vital signs of the patients $18_1 \ldots 18_P$ may be monitored and tracked/analyzed while they are being prepared for transportation and during transportation.

Locations of the first responders $14_1 \ldots 14_N$ and the patients $18_1 \ldots 18_P$, as well as evolution of hazardous conditions at the incident scene 12, may be tracked and alerts may be sent to the first responders as the environment at the incident scene 12 changes.

Clinical workflows of the first responders $14_1 \ldots 14_N$ can be integrated with workflows of the healthcare facility 33, allowing its ER (or other receiving department) to prepare for incoming ones of the patients $18_1 \ldots 18_P$. Specifically, the healthcare facility 33 receives information indicative of the number, type and condition of the patients $18_1 \ldots 18_P$, both from the first responders $14_1 \ldots 14_N$ who provide assessments and/or communicates with clinicians using their first responder packs $22_1 \ldots 22_N$ and from the ECAS 30 which analyzes the ongoing dynamic, monitoring the location, vital condition, environmental conditions of each patient, allowing the ECAS 30 to build up a patient record, combine this with any previous EPR, EMR, EHR, flag issues (e.g. allergies) to the first responder and the general clinical team and to take various actions as-needed based on multiple factors including clinician skills and availability, first responder skills, availability and proximity to the patient, etc. according to policies, procedures appropriate to the deemed situation as well as flag other threats to the patient before or during transportation.

The ECAS 30 can monitor a patient $18_j$ and, based upon his/her dynamic patient clinical condition, may instruct actions to be carried out, such as immediate or more urgent transportation of the patient $18_j$, may request activity of a first responder $14_j$ on the patient $18_j$ and/or may present its findings to a hospital clinician to trigger these events or may put the clinician in contact with the first responder $14_j$, or may forward the patient information to an appropriate clinician for their determination of a course of action, based upon hospital policies and procedures.

Based upon the collected data, the ECAS 30 can communicate with an appropriate clinician on a basis of factors such as skills, availability/current and planned workload, duty roster, assignment (e.g. to ER), and can establish communications between the clinician and one or more of the first responders $14_1 \ldots 14_N$, especially the first responder who is with or nearest to a particular patient whose treatment requires information from the clinician.

Assessments of the number, condition, and likely level of treatment of the patients $18_1 \ldots 18_P$ can be made to route those patients who require further treatment to the healthcare facility 33 and/or one or more other receiving healthcare facilities which is/are best suited, allowing load leveling across the ERs of multiple hospitals and allowing the entire ER resources of multiple hospitals to be brought to bear without ending up with too many cases at one ER, while another one is under-loaded.

Verbal assessments about the incident scene 12 made by the first responders $14_1 \ldots 14_N$ may not only be communicated to personnel at the healthcare facility 33, but may also be integrated with other data generated by the packs $22_1 \ldots 22_N$, $24_1 \ldots 24_P$, $26_1 \ldots 26_R$. For instance, in some embodiments, the communication system 208 of the healthcare facility 33 may implement speech processing unit that can parse a verbal assessment made by a first responder $14_j$ using the communication unit 59 of his/her first responder pack $22_j$ to identify relevant items of information contained in the first responder's verbal assessment and provide data conveying this information to the ECAS 30 (e.g., to the environmental data processing engine 411 or the situational context processing engine 421). For example, the first responder $14_j$ arrives at the incident scene 12 and realizes that multiple people are injured. The first responder $14_j$ can very quickly recognize and diagnose (at a certain level) various medical related attributes of an injured person and verbally express his/her assessment (e.g., "Medical emergency. Victim female, no identification, Jane Doe, age ~25-30, second degree burns on left arm and leg. Possible fractured left leg. Heavy bleeding above right eye. Collecting pulse and BP from sensor pack"), which is processed by the speech processing unit that parses the verbal assessment, identifies relevant items of information contained therein, assigns meta-tags, and send the resulting data to the ECAS 30 where it is integrated with all other appropriate sensor/context information associated with that person's condition.

While these examples illustrate certain benefits that can be provided by the first response support system 10, it will be appreciated that various other benefits may arise from use of the first response support system 10.

Cascaded Location Process

As mentioned above, in this embodiment, the processing system 20 implements the cascaded location process to extend its location-awareness capability across the incident scene 12. Generally, with the cascaded location process, the processing system 20 determines the locations of the first responder packs $22_1 \ldots 22_N$, the drop packs $26_1 \ldots 26_R$, and the patient packs $24_1 \ldots 24_P$ in multiple stages, whereby located ones of these packs are used to receive wireless location signals from unlocated ones of these packs and transmit wireless signals to the processing system 20 on a basis of the wireless location signals that they receive in order to enable the locations of the unlocated packs to be determined.

The cascaded location process will now be further discussed with reference to FIGS. 9A to 9E, in an example scenario where three vehicles $16_x$, $16_y$, $16_z$ transporting three ECAS outstations $28_x$, $28_y$, $28_z$ arrive at the incident scene 12.

A location of each of the ECAS outstations $28_x$, $28_y$, $28_z$ is determined by the ECAS 30 using the outstation location unit 310 of these outstations. More particularly, in this embodiment, the GPS receiver of the outstation location unit 310 of each of the ECAS outstations $28_x$, $28_y$, $28_z$ allows each of these outstations to transmit location data indicative of its location to the ECAS 30 via its wireless ECAS interface 340.

Each of the ECAS outstations $28_x$, $28_y$, $28_z$ extends its extensible arms $307_1 \ldots 307_5$ on which are disposed its pack location units $302_1 \ldots 302_5$. Locations of the pack location units $302_1 \ldots 302_5$ of each of the ECAS outstations $28_x$, $28_y$, $28_z$ are determined by the processing system 20. In this embodiment, the processing system 20 determines the location of each of the pack location units $302_1 \ldots 302_5$ of each of the ECAS outstations $28_x$, $28_y$, $28_z$ based on times of arrival of a wireless location signal transmitted by its location transmitter 306 at three or more of the location receivers 303 of the pack location units $302_6 \ldots 302_9$ (fixed at known locations) of that ECAS outstation (or otherwise, such as based on engineering and other information regarding the extensible arms $307_1 \ldots 307_5$, such as their actual extension length and orientation). Once located, the pack location units $302_1 \ldots 302_5$ of each of the ECAS outstations $28_x$, $28_y$, $28_z$ have their location receivers 303 activated.

The location receivers 303 of the ECAS outstations $28_x$, $28_y$, $28_z$ create respective "primary" coverage areas $A1_x$, $A1_y$, $A1_z$ of these outstations. The primary coverage area $A1_x$ refers to an area in which each point is within the respective ranges of at least three location receivers 303 of the ECAS outstation $28_x$, thereby allowing a location transmitter in that area to be located through application of triangulation techniques based on a wireless location signal transmitted by that location transmitter and received at these location receivers. The primary coverage areas $A1_y$ and $A1_z$ of the ECAS outstations $28_y$ and $28_z$ are similarly defined.

In addition, the location receivers 303 of the ECAS outstations $28_x$, $28_y$, $28_z$ create respective "secondary" coverage areas $A2_x$, $A2_y$, $A2_z$ and respective "tertiary" coverage areas $A3_x$, $A3_y$, $A3_z$ of these outstations. The secondary coverage area $A2_x$ refers to an area in which each point is within the respective ranges of only two location receivers 303 of the ECAS outstation $28_x$, while the tertiary coverage area $A3_x$ refers to an area in which each point is within the range of only one location receiver 303 of the ECAS outstation $28_x$. The secondary coverage areas $A2_y$ and $A2_z$ and the tertiary coverage areas $A3_y$ and $A3_z$ of the ECAS outstations $28_y$ and $28_z$ are similarly defined. While a location transmitter located in only one of the secondary coverage areas $A2_x$, $A2_y$, $A2_z$ and tertiary coverage areas $A3_x$, $A3_y$, $A3_z$ cannot be located by the processing system 20, a location transmitter located in a region where two or more of these secondary and tertiary coverage areas overlap may be locatable by the processing system 20. In other words, a location transmitter lying outside the primary coverage areas $A1_x$, $A1_y$, $A1_z$ of the ECAS outstations $28_x$, $28_y$, $28_z$ and transmitting a wireless location signal can be located by the processing system 20 when this wireless location signal is received by three or more location receivers 303 distributed among two or all three of the ECAS outstations $28_x$, $28_y$, $28_z$.

While they are shown as circles for simplicity, the coverage areas $A1_x$, $A1_y$, $A1_z$, $A2_x$, $A2_y$, $A2_z$, $A3_x$, $A3_y$, $A3_z$ will typically have more complex configurations depending on the number, relative positions and nature (e.g., omnidirectional or directional, range, etc.) of the location receivers 303 of the ECAS outstations $28_x$, $28_y$, $28_z$ and possibly other factors (e.g., signal path impairments and/or blockages, etc.).

Figure 9A:
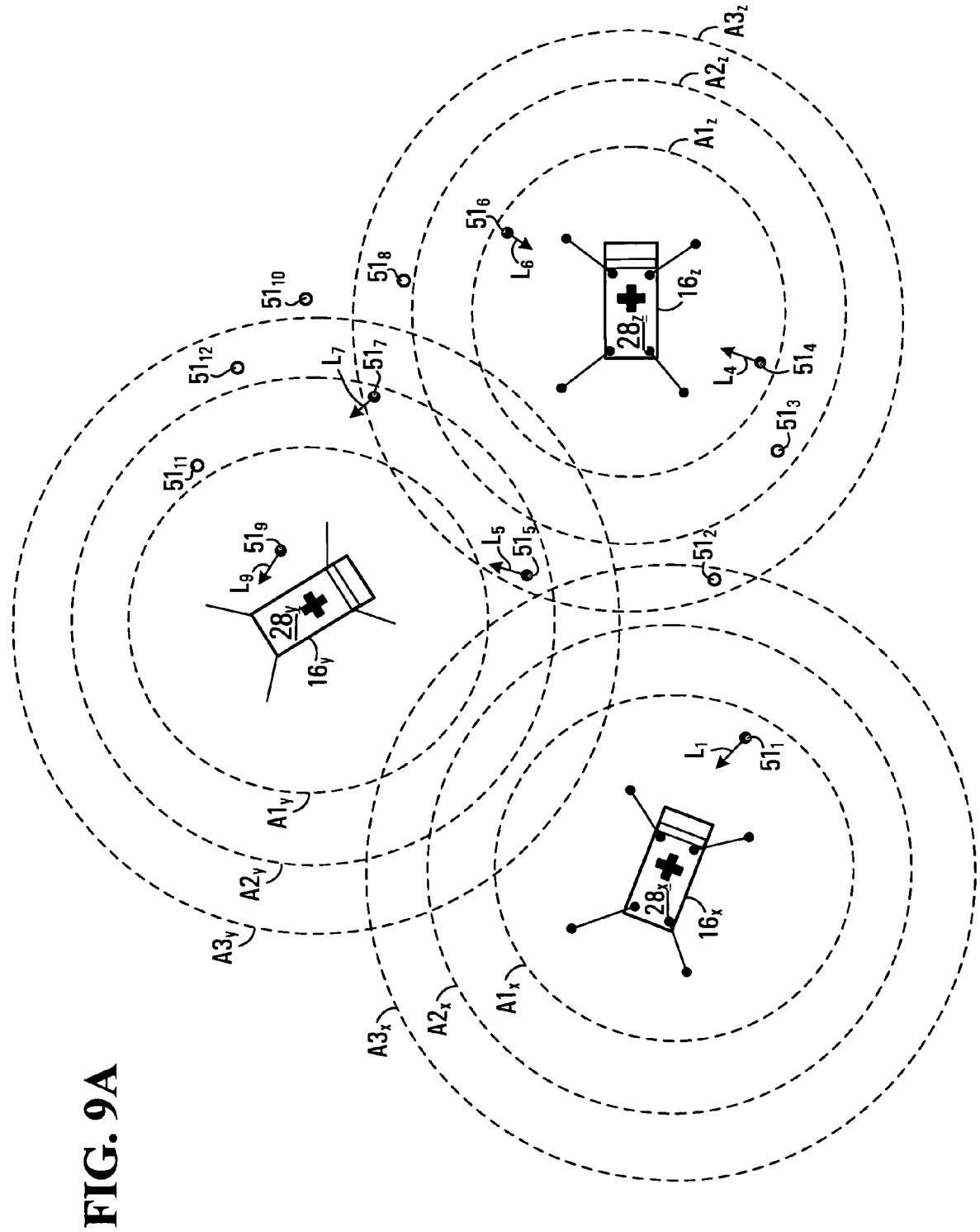
FIGS. 9A to 9E show a cascaded location process to extend a location-awareness capability of the first response support system across the incident scene, in accordance with an embodiment of the invention.

Meanwhile, some of the first responders $14_1 \ldots 14_N$ who arrived on the vehicles $16_x$, $16_y$, $16_z$ are deployed, carrying with them some of the first responder packs $22_1 \ldots 22_N$ as well as some of the patient packs $24_1 \ldots 24_P$ and some of the drop packs $26_1 \ldots 26_R$. For purposes of this example, it is assumed that, at a particular moment, these packs, which are denoted $51_1 \ldots 51_{12}$ (where each pack $51_j$ is one of the packs $22_1 \ldots 22_N$, $24_1 \ldots 24_P$, $26_1 \ldots 26_R$), are distributed at the incident scene 12 as shown in FIG. 9A.

First Stage

The packs $51_1$, $51_4$, $51_6$, $51_9$ are located in the primary coverage areas $A1_x$, $A1_y$, $A1_z$ of the ECAS outstations $28_x$, $28_y$, $28_z$ and are thus locatable. For example, the location transmitter 41, 141, 241 of the pack $51_1$ transmits a wireless location signal $L_1$ that is received by three or more location receivers 303 of the ECAS outstation $28_x$. Based on the wireless location signal $L_1$, the processing system 20 proceeds to determine a location of the pack $51_1$.

More particularly, in this embodiment, the processing entity 360 of the ECAS outstation $28_x$ transmits data derived from the wireless location signal $L_1$ to the ECAS 30 via its wireless ECAS interface 340. In this case, the data derived from the wireless location signal $L_1$ comprises data relating to times of arrival of that signal at the three or more location receivers 303 of the ECAS outstation $28_x$. Also, in this case, the data derived from the wireless location signal $L_1$ comprises identification data conveyed by that signal and provided by the identification unit 46, 146, 246 of the pack $51_1$.

Upon receiving the data derived from the wireless location signal $L_1$ via the wireless outstation interface 400, and with knowledge of the location of the ECAS outstation $28_x$, the processing entity 420 of the ECAS 30 determines the location of the pack $51_1$ based on this data. More particularly, in this embodiment, the environmental data processing engine 411 implements a location determination unit 432 that determines the location of the pack $51_1$ based on the data relating to the times of arrival of the wireless location signal $L_1$ at the three or more location receivers 303 of the ECAS outstation $28_x$. The location determination unit 432 can employ any suitable triangulation technique (or any other suitable location determination technique or range and direction determination technique).

Figure 10A:
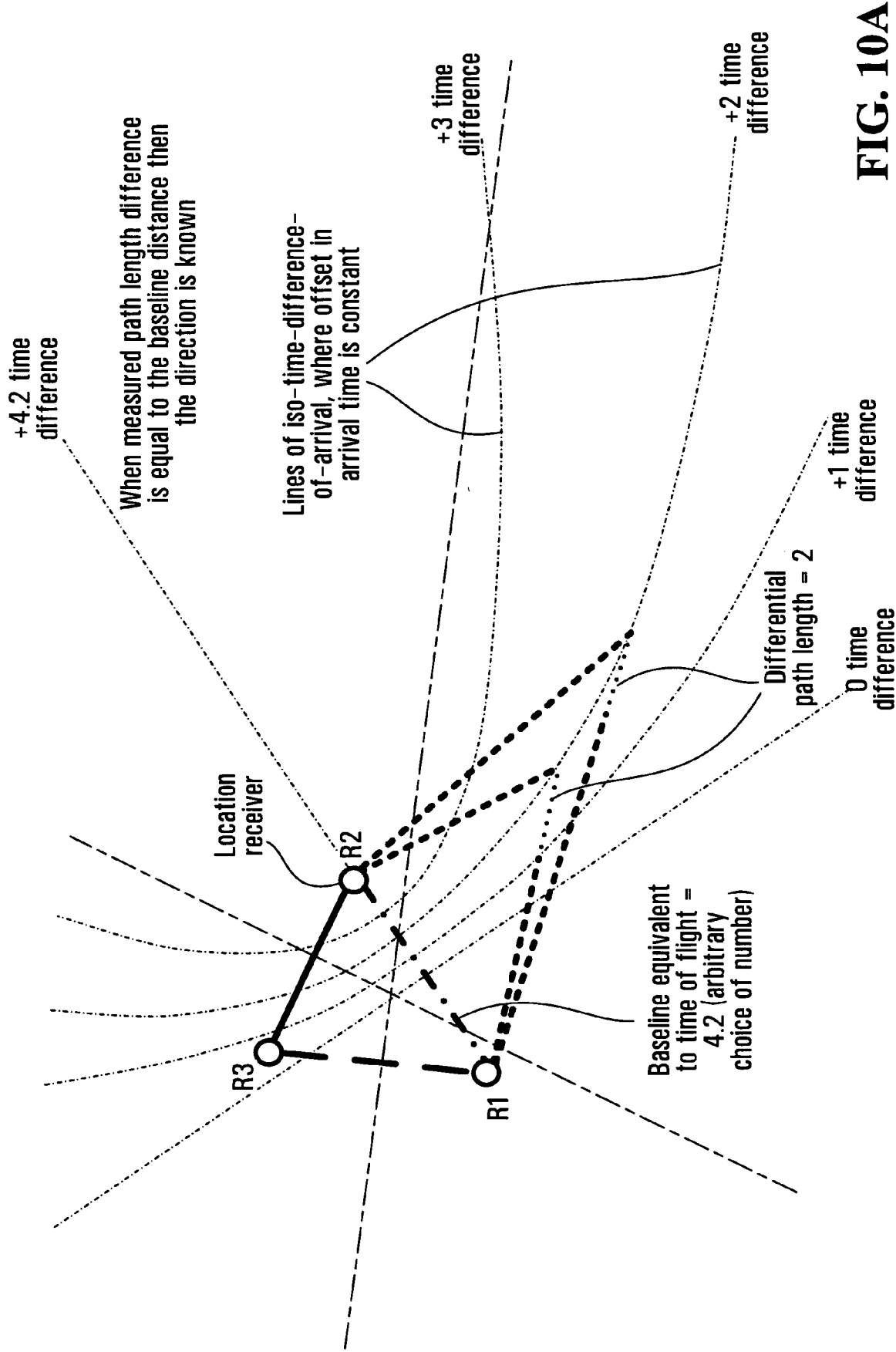
Figure 10B:
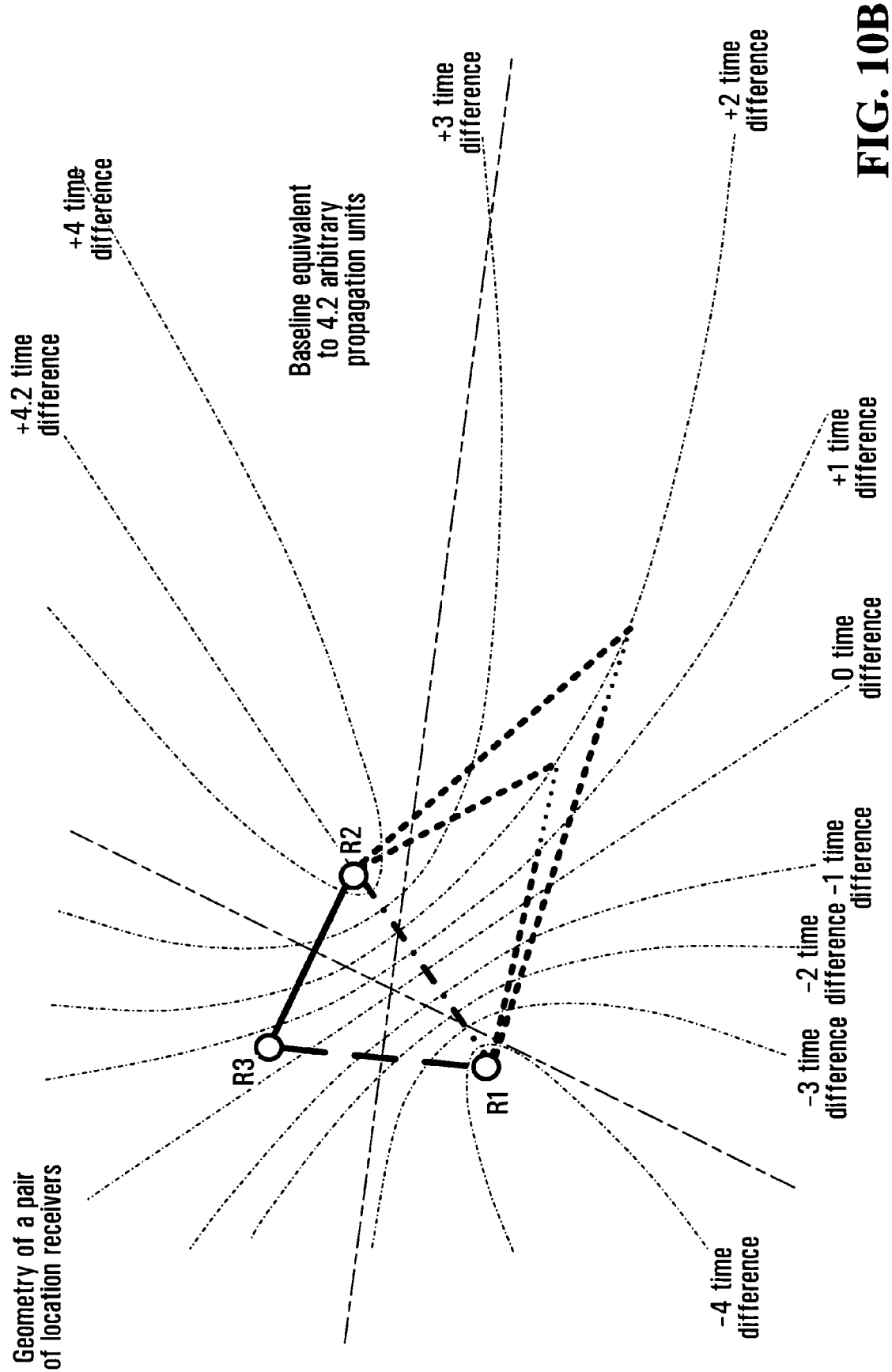
Figure 10C:
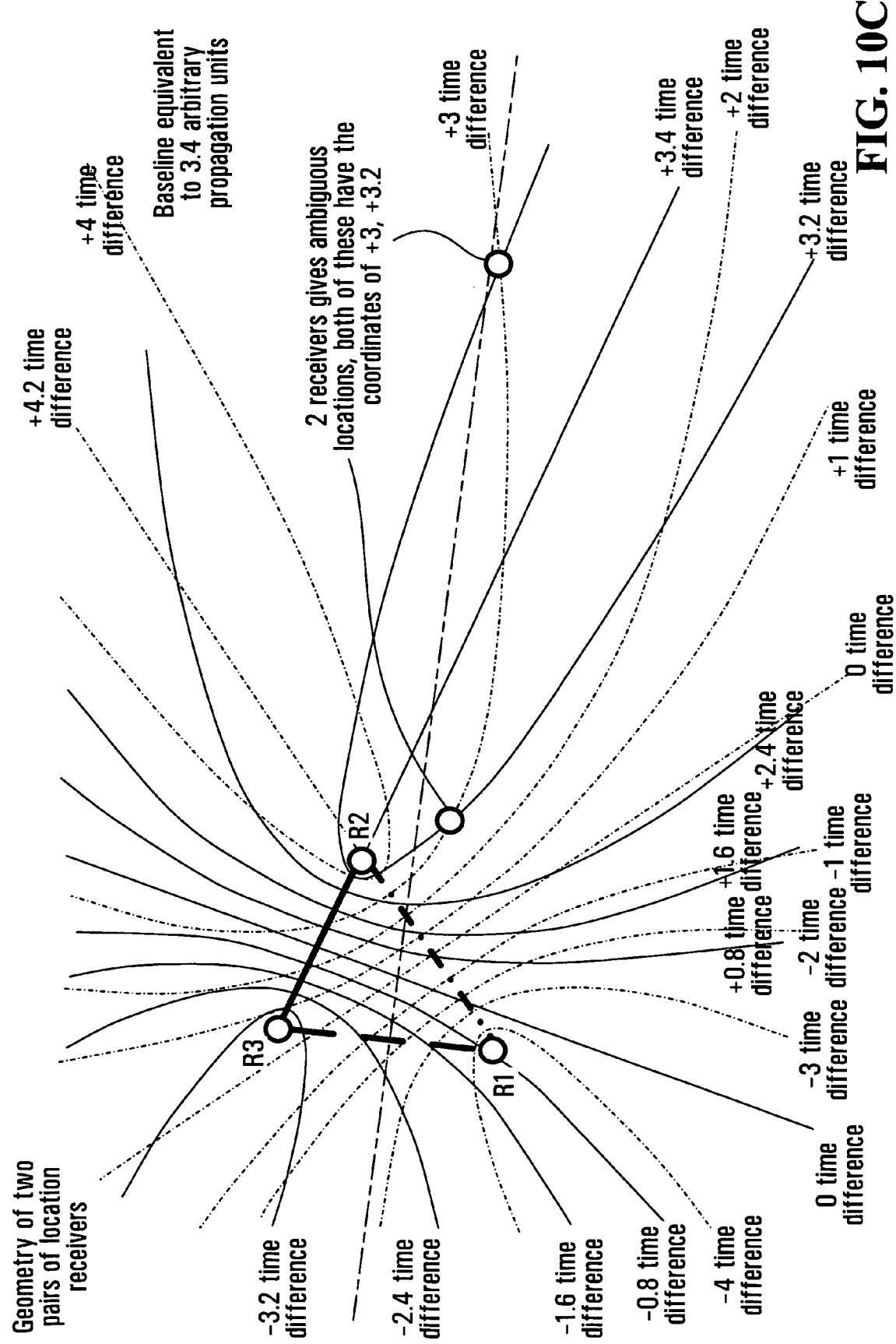

For example, FIGS. 10A to 10D show an example of a geometry associated with a location determination process based on a differential time of arrival solution. Considering FIG. 10A, this shows a case where three location receivers R1, R2, and R3 (which can be any three location receivers 303 of the ECAS outstation $28_x$) receive the wireless location signal $L_1$ transmitted by the pack $51_1$ and where the location receivers R1 and R2 have cooperated to determine that R1 received the signal $L_1$ at time +2 relative to when R2 received the signal $L_1$. Thus, the time of flight of the signal $L_1$ to the location receiver R1 is longer by a factor of the time difference multiplied by the propagation velocity, which in this case is the speed of light. The locus or curve of locations which can meet this criterion can be plotted, as shown as "+2 time difference" in FIG. 10A. Other time differences result in other locus curves but the pack $51_1$ could be located anywhere along that curve. FIG. 10B shows the complete set of locus curves for the location receivers R1 and R2. FIG. 10C overlays the R1-R2 locus curves with the locus curves developed by comparing the time of reception of the signal $L_1$ at location receivers R3 and R2. While the locus curves are similar in structure to the locus curves of R1 and R2 they are developed around a different baseline, that of R2 to R3, and so do not coincide with the R1-R2 locus curves Hence, by combining these measurements the actual location can be narrowed down to one or sometimes two locations. Repeating this with the third available baseline, R1 to R3, allows the ambiguity to be resolved as is shown in FIG. 10D. As is also shown in these figures, the system becomes less precise at greater distances due to the reduced subtended angle between the source and the receiver baselines. This can be improved by increasing the receiver baselines, either by extending the arms $307_1 \ldots 307_5$ of the first response vehicle $16_x$ or, once the baseline between various vehicles and/or located packs is determined, using those as a long baseline measuring capability. While this example illustrates one type of location determination process, various other location determination processes may be used in other examples The environmental data processing engine 411 thus obtains data indicative of the location of the pack $51_1$ from its location determination unit 432. In other embodiments, the location determination unit 432 may be distinct from but connected to the environmental data processing engine 411 to which it may feed the data indicative of the location of the pack $51_1$ when generated.

In a similar manner, the processing system 20 proceeds to determine a location of each of the packs $51_4$, $51_6$, $51_9$ based on wireless location signals $L_4$, $L_6$, $L_9$ transmitted by these packs and received by three or more location receivers 303 of the ECAS outstation $28_y$, $28_z$.

The packs $51_5$, $51_7$ are located in a region where the secondary coverage area $A2_y$ of the ECAS outstation $28_y$ and the tertiary coverage area $A3_z$ of the ECAS outstation $28_z$ overlap, and are thus also locatable. For example, the location transmitter 41, 141, 241 of the pack $51_5$ transmits a wireless location signal $L_5$ that is received by only two location receivers 303 of the ECAS outstation $28_y$, but that is also received by a single one of the location receivers 303 of the ECAS outstation $28_z$. Based on the wireless location signal $L_5$, the processing system 20 proceeds to determine a location of the pack $51_5$.

More particularly, the processing entity 360 of the ECAS outstation $28_y$ transmits data derived from the wireless location signal $L_5$ to the ECAS 30 via its wireless ECAS interface 340, where this data comprises data relating to times of arrival of that signal at the two location receivers 303 of the ECAS outstation $28_y$ as well as identification data conveyed by that signal and provided by the identification unit 46, 146, 246 of the pack $51_5$. Similarly, the processing entity 360 of the ECAS outstation $28_z$ transmits data derived from the wireless location signal $L_5$ to the ECAS 30 via its wireless ECAS interface 340, where this data comprises data relating to a time of arrival of that signal at the single one of the location receivers 303 of the ECAS outstation $28_z$ as well as identification data conveyed by that signal and provided by the identification unit 46, 146, 246 of the pack $51_5$.

Upon receiving the data derived from the wireless location signal $L_5$ from the ECAS outstations $28_y$, $28_z$ via the wireless outstation interface 400, and with knowledge of the location of each of the ECAS outstations $28_y$, $28_z$, the processing entity 420 of the ECAS 30 determines the location of the pack $51_5$ based on this data. More particularly, the location determination unit 432 implemented by the environmental data processing engine 411 determines the location of the pack $51_5$ based on the data relating to the times of arrival of the wireless location signal $L_5$ at the two location receivers 303 of the ECAS outstation $28_y$ and at the single one of the location receivers 303 of the ECAS outstation $28_z$. The environmental data processing engine 411 thus obtains data indicative of the location of the pack $51_5$.

In a similar manner, the processing system 20 proceeds to determine a location of the pack $51_7$ based on a wireless location signal $L_7$ transmitted by that pack and received by only two location receivers 303 of the ECAS outstation $28_y$, but also received by a single one of the location receivers 303 of the ECAS outstation $28_z$.

Second Stage

Having determined the locations of the packs $51_1$, $51_4$, $51_5$, $51_6$, $51_7$, $51_9$, the processing system 20 may use these known locations to determine the locations of other ones of the packs $51_1 \ldots 51_{12}$.

Figure 9B:
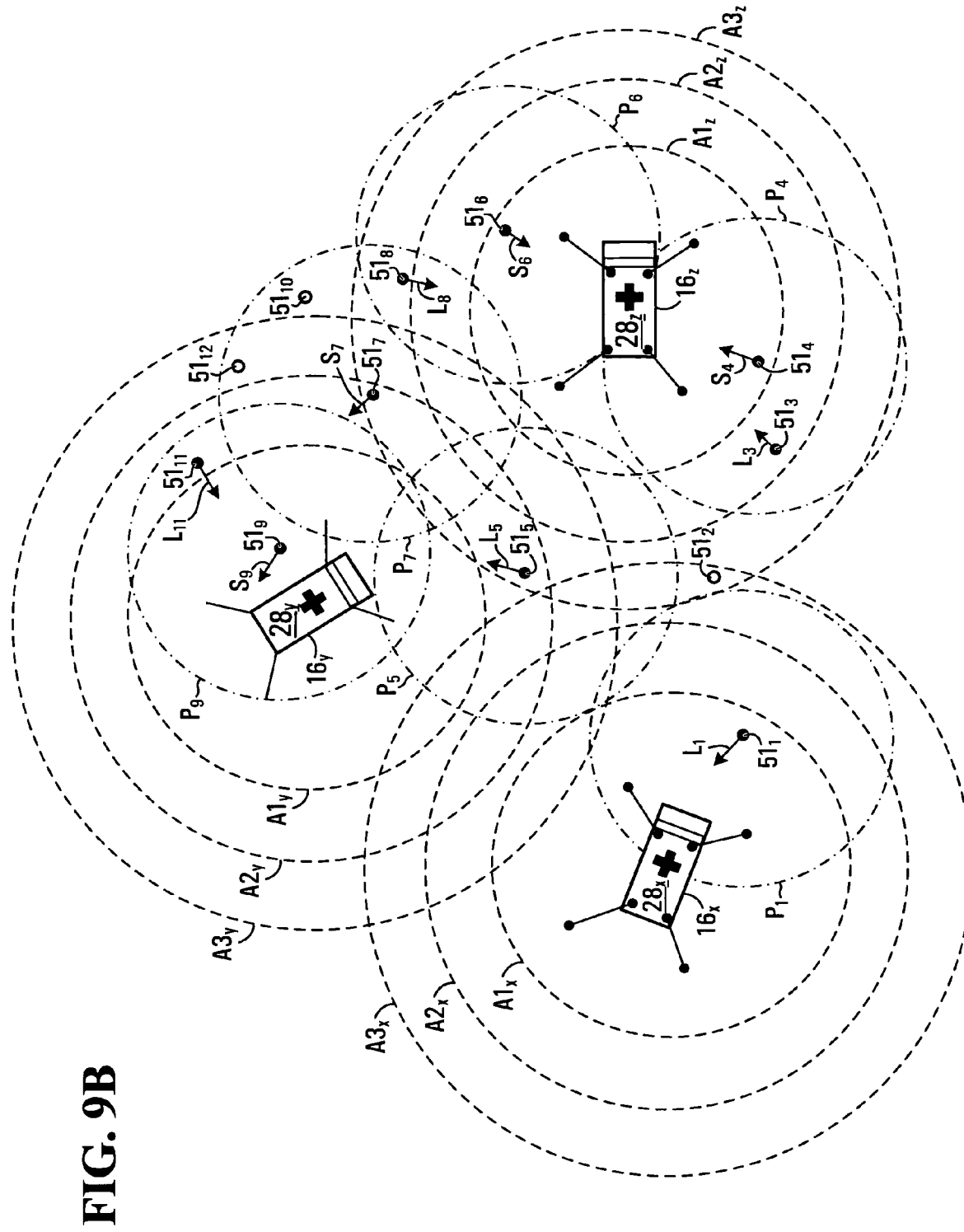

Specifically, the ECAS outstation $28_x$, $28_y$, $28_z$ send wireless signals to the packs $51_1$, $51_4$, $51_5$, $51_6$, $51_7$, $51_9$ conveying commands to activate their location receiver 43, 143, 243 in order to receive wireless location signals from other ones of the packs $51_1 \ldots 51_{12}$ that might be within their range. As shown in FIG. 9B, the location receivers 43, 143, 243 of the packs $51_1$, $51_4$, $51_5$, $51_6$, $51_7$, $51_9$ have respective ranges that create respective coverage areas $P_1$, $P_4$, $P_5$, $P_6$, $P_7$, $P_9$, whereby a wireless signal transmitted by a location transmitter within the coverage area $P_1$ is received by the pack $51_1$, a wireless signal transmitted by a location transmitter within the pack coverage area $P_2$ is received by the pack $51_2$, and so on. While they are shown as circles for simplicity, the coverage areas $P_1$, $P_4$, $P_5$, $P_6$, $P_7$, $P_9$ may have more complex configurations depending on the nature (e.g., omnidirectional or directional, range, etc.) of the location receivers 43, 143, 243 of the packs $51_1$, $51_4$, $51_5$, $51_6$, $51_7$, $51_9$ and possibly other factors (e.g., signal path impairments and/or blockages, etc.).

The coverage areas $P_1$, $P_4$, $P_5$, $51_6$, $P_7$, $P_9$ of the packs $51_1$, $51_4$, $51_5$, $51_6$, $51_7$, $51_9$ can be combined with one or more of the secondary coverage areas $A2_x$, $A2_y$, $A2_z$ and tertiary coverage areas $A3_x$, $A3_y$, $A3_z$ of the ECAS outstations $28_x$, $28_y$, $28_z$ in order to locate other ones of the packs $51_1 \ldots 51_{12}$. Specifically, a location transmitter located in a region where one or more of the coverage areas $P_1$, $P_4$, $P_5$, $51_6$, $P_7$, $P_9$ and one of the secondary coverage areas $A2_x$, $A2_y$, $A2_z$ overlap or in a region where one or more of the coverage areas $P_1$, $P_4$, $P_5$, $51_6$, $P_7$, $P_9$ and two of the tertiary coverage areas $A3_x$, $A3_y$, $A3_z$ overlap can be located by the processing system 20. Also, depending on distribution of the coverage areas $P_1$, $P_4$, $P_5$, $51_6$, $P_7$, $P_9$, a location transmitter located in a region where three or more of the coverage areas $P_1$, $P_4$, $P_5$, $51_6$, $P_7$, $P_9$ overlap can be located by the processing system 20. In other words, a location transmitter can be located by the processing system 20 when a wireless location signal that it transmits is received by three or more location receivers 303, 43, 143, 243 that are distributed among two or more of the ECAS outstations $28_x$, $28_y$, $28_z$ and the packs $51_1$, $51_4$, $51_5$, $51_6$, $51_7$, $51_9$.

In this case, the pack $51_3$ is located in a region where the secondary coverage area $A2_z$ of the ECAS outstation $28_z$ and the coverage area $P_4$ of the pack $51_4$ overlap, the pack $51_8$ is located in a region where the tertiary coverage area $A3_z$ of the ECAS outstation $28_z$ and the coverage areas $P_6$, $P_7$ of the packs $51_6$, $51_7$ overlap, and the pack $51_{11}$ is located in a region where the secondary coverage area $A2_y$ of the ECAS outstation $28_y$ and the coverage area $P_9$ of the pack $51_9$ overlap. As such, the packs $51_3$, $51_8$, $51_{11}$ are locatable.

For example, the location transmitter 41, 141, 241 of the pack $51_3$ transmits a wireless location signal $L_3$ that is received by only two location receivers 303 of the ECAS outstation $28_z$, but that is also received by the location receiver 43, 143, 243 of the pack $51_4$. Based on the wireless location signal $L_3$, the processing system 20 proceeds to determine a location of the pack $51_3$.

More particularly, the pack $51_4$ sends a wireless signal $S_4$ to the ECAS outstation $28_z$ via its wireless interface 42, 142, 242, in response to receipt of the wireless location signal $L_3$ by its location receiver 43, 143, 243. The wireless signal $S_4$ conveys data derived from the wireless location signal $L_3$, i.e., data conveyed by the signal $L_3$ and/or data generated upon reception of the signal $L_3$. In this case, the data conveyed by the wireless signal $S_4$ comprises data relating to a time of arrival of the signal $L_3$ at the location receiver 43, 143, 243 of the pack $51_4$ as well as identification data conveyed by the signal $L_3$ and provided by the identification unit 46, 146, 246 of the pack $51_3$. The wireless signal $S_4$ also conveys the identification data provided by the identification unit 46, 146, 246 of the pack $51_4$ in order to allow the ECAS outstation $28_z$ to identify the pack $51_4$ from which it receives the signal $S_4$.

The processing entity 360 of the ECAS outstation $28_z$ transmits data derived from the wireless location signal $L_3$ to the ECAS 30 via its wireless ECAS interface 340. In this case, the data derived from the wireless location signal $L_3$ comprises data relating to times of arrival of the signal $L_3$ at the two location receivers 303 of the ECAS outstation $28_z$ and at the location receiver 43, 143, 243 of the pack $51_4$, as well as the identification data conveyed by the signal $L_3$ and provided by the identification unit 46, 146, 246 of the pack $51_3$. The processing entity 360 of the ECAS outstation $28_z$ also transmits to the ECAS 30 via its wireless ECAS interface 340 the identification data conveyed by the wireless signal $S_4$, which identifies the pack $51_4$ at which the signal $L_3$ was also received.

Upon receiving the data derived from the wireless location signal $L_3$ and the identification data identifying the pack $51_4$ from the ECAS outstation $28_z$ via the wireless outstation interface 400, and with knowledge of the location of each of the ECAS outstation $28_z$ and the pack $51_4$, the processing entity 420 of the ECAS 30 determines the location of the pack $51_3$ based on this data. More particularly, the location determination unit 432 implemented by the environmental data processing engine 411 determines the location of the pack $51_3$ based on the data relating to the times of arrival of the wireless location signal $L_3$ at the two location receivers 303 of the ECAS outstation $28_z$ and at the location receiver 43, 143, 243 of the pack $51_4$. The environmental data processing engine 411 thus obtains data indicative of the location of the pack $51_3$.

In a similar manner, the processing system 20 proceeds to determine a location of the pack $51_{11}$ based on a wireless location signal $L_{11}$ transmitted by that pack and received by only two location receivers 303 of the ECAS outstation $28_y$, but also received by the location receiver 43, 143, 243 of the pack $51_9$, which transmits a wireless signal $S_9$ to the ECAS outstation $28_y$ in response to receiving the signal $L_{11}$. Also, the processing system 20 proceeds to determine a location of the pack $51_8$ based on a wireless location signal $L_8$ transmitted by that pack and received by only one location receiver 303 of the ECAS outstation $28_z$ but also received by the location receivers 43, 143, 243 of the packs $51_6$, $51_7$, which transmit wireless signals $S_6$, $S_7$ to the ECAS outstations $28_z$, $28_y$ in response to receiving the signal $L_8$.

Subsequent Stages

Having determined the locations of the packs $51_1$, $51_3$, $51_4$, $51_5$, $51_6$, $51_7$, $51_8$, $51_9$, $51_{11}$, the processing system 20 may use these known locations to determine the locations of remaining ones of the packs $51_1 \ldots 51_{12}$.

Figure 9C:
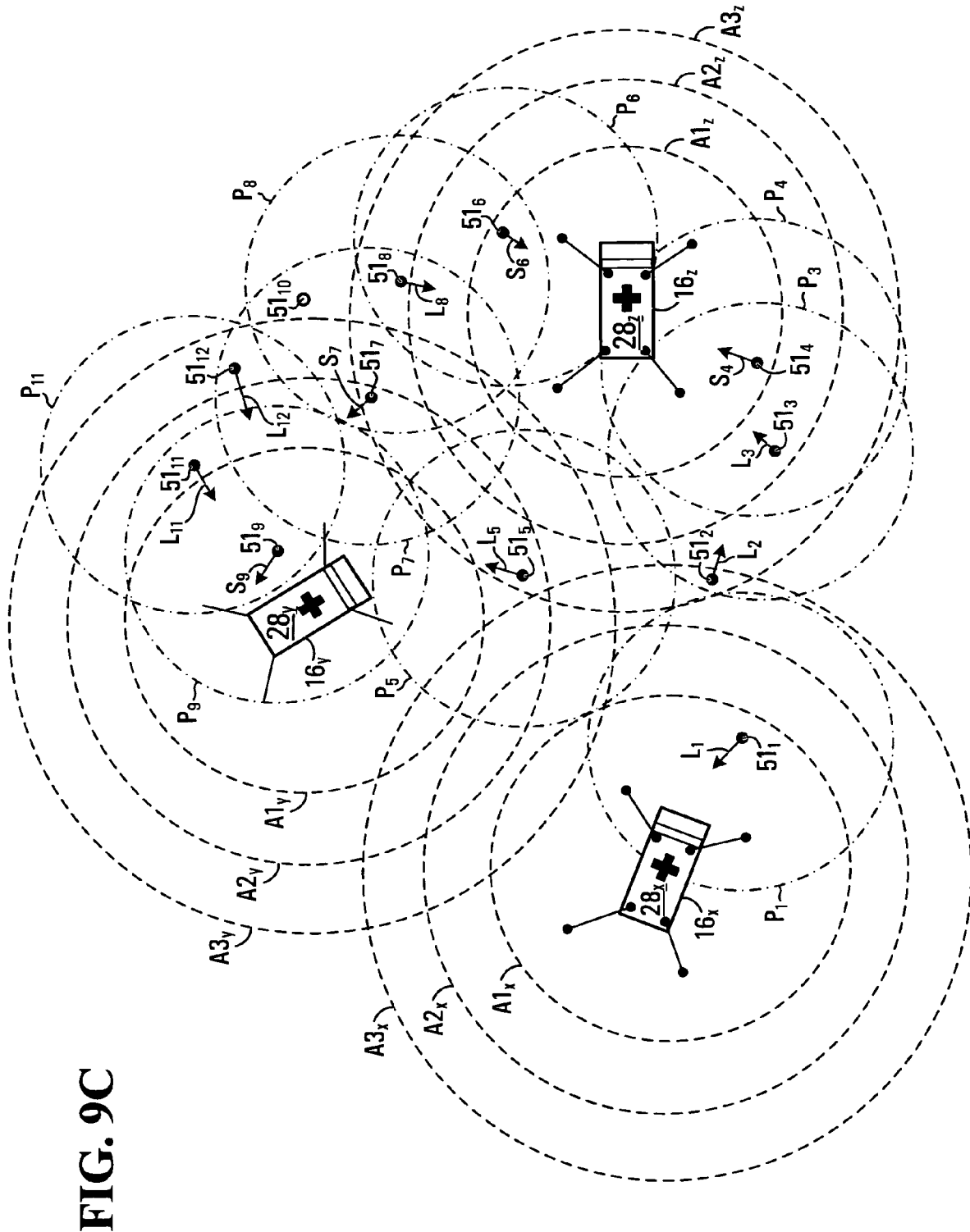

Specifically, as described above for the second stage, the ECAS outstation $28_x$, $28_y$, $28_z$ send wireless signals to the packs $51_3$, $51_8$, $51_{11}$ conveying commands to activate their location receiver 43, 143, 243 in order to receive wireless location signals from other ones of the packs $51_1 \ldots 51_{12}$ that might be within their range. As shown in FIG. 9C, this results in creation of respective coverage areas $P_3$, $P_8$, $P_1$ of the packs $51_3$, $51_8$, $51_{11}$, thereby further expanding the overall coverage area. Through overlapping ones of the coverage areas $P_1$, $P_3$, $P_4$, $P_5$, $P_6$, $P_7$, $P_8$, $P_9$, $P_{11}$ of the packs $51_1$, $51_3$, $51_4$, $51_5$, $51_6$, $51_7$, $51_8$, $51_9$, $51_{11}$ and the secondary coverage areas $A2_x$, $A2_y$, $A2_z$ and tertiary coverage areas $A3_x$, $A3_y$, $A3_z$ of the ECAS outstations $28_x$, $28_y$, $28_z$, other ones of the packs $51_1 \ldots 51_{12}$ can be located by the processing system 20. Indeed, a location transmitter can be located by the processing system 20 when a wireless location signal that it transmits is received by three or more location receivers 303, 43, 143, 243 that are distributed among two or more of the ECAS outstations $28_x$, $28_y$, $28_z$ and the packs $51_1$, $51_4$, $51_5$, $51_6$, $51_7$, $51_9$, $51_1$, $51_3$, $51_4$, $51_5$, $51_7$, $51_8$, $51_9$, $51_{11}$, in a manner similar to that described above for the second stage.

In this case, the pack $51_2$ is located in a region where the tertiary coverage areas $A3_x$, $A3_z$ of the ECAS outstations $28_x$, $28_z$ and the coverage area $P_3$ of the pack $51_3$ overlap, and the pack $51_{12}$ is located in a region where the tertiary coverage area $A3_y$ of the ECAS outstation $28_y$ and the coverage areas $P_{11}$, $P_7$ of the packs $51_{11}$, $51_7$ overlap. As such, the packs $51_2$, $51_{12}$ are located by the processing system 20 based on wireless locations signals $L_2$, $L_{12}$ that they transmit, in a manner similar to that describe above for the second stage.

Figure 9D:
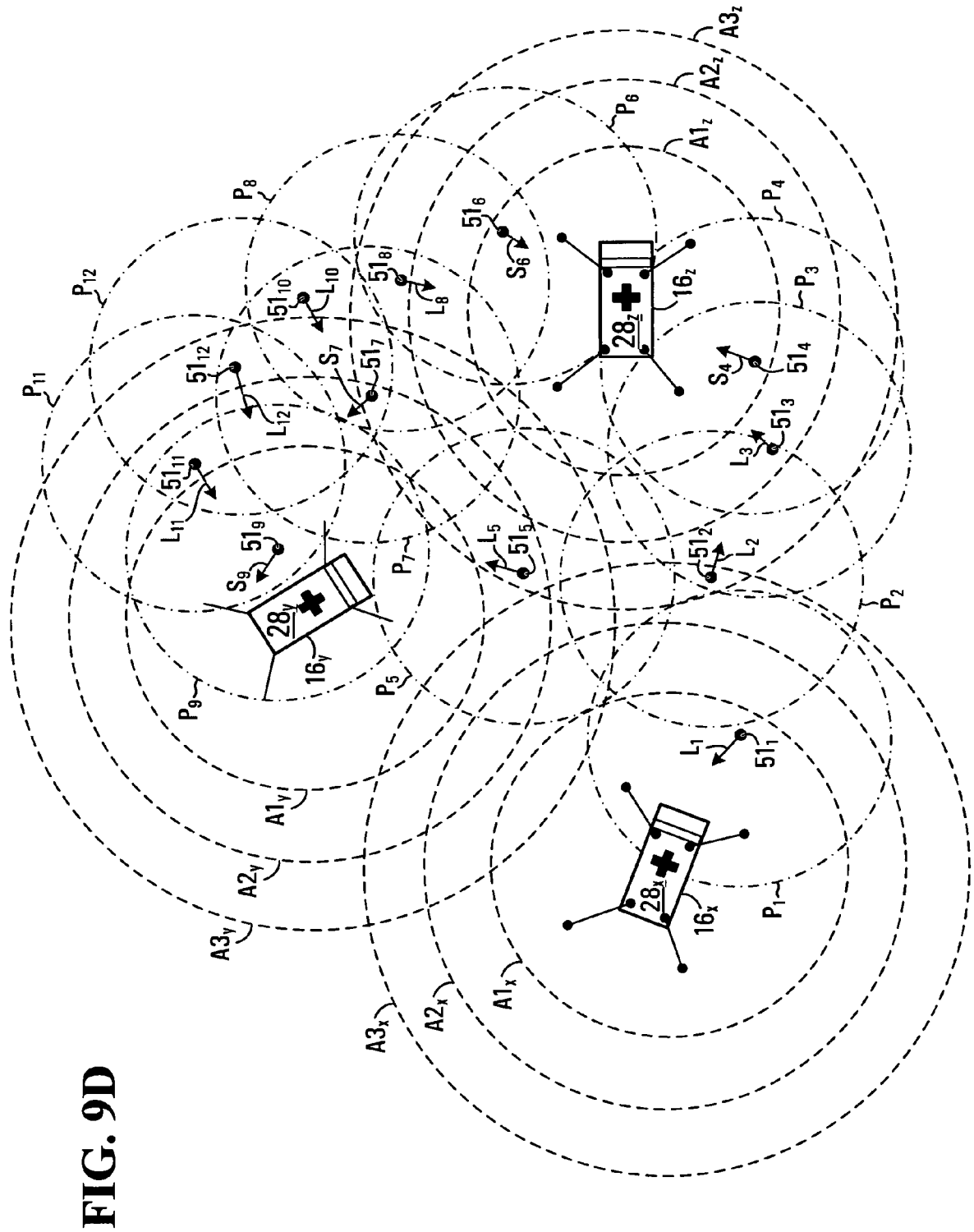

With the locations of the packs $51_2$, $51_{12}$ determined, the ECAS outstation $28_x$, $28_y$, $28_z$ send wireless signals to these packs conveying commands to activate their location receiver 43, 143, 243 in order to receive wireless location signals from other ones of the packs $51_1 \ldots 51_{12}$ that might be within their range. As shown in FIG. 9D, this results in creation of respective coverage areas $P_2$, $P_{12}$ of the packs $51_2$, $51_{12}$, thereby further expanding the overall coverage area.

Figure 9E:
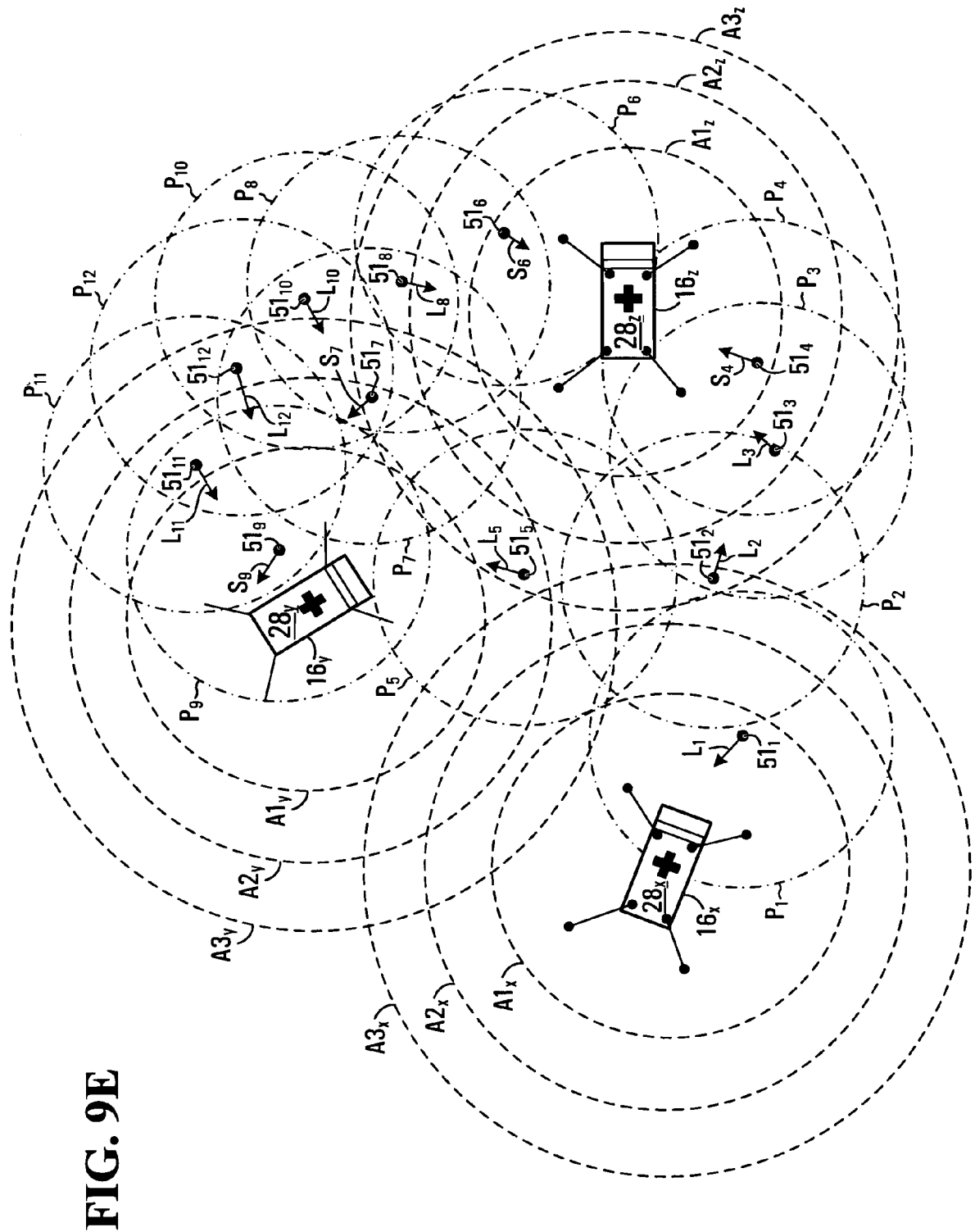

This latest expansion of the overall coverage area results in the pack $51_{10}$ being located in a region where the coverage areas $P_7$, $P_8$, $P_{12}$ of the packs $51_7$, $51_8$, $P_{12}$ overlap. As such, the pack $51_{10}$ is located by the processing system 20 based on a wireless locations signal $L_{10}$ that it transmits, leading to addition of its coverage area $P_{10}$ to the overall coverage area, as shown in FIG. 9E.

It will thus be appreciated that, through its multiple stages, the cascade location process enables the processing system 20 to extend its location-awareness capability across the incident scene 12 in an efficient manner by essentially "daisy-chaining" some of the first responder packs $22_1 \ldots 22_N$, patient packs $24_1 \ldots 24_P$ and drop packs $26_1 \ldots 26_R$ that are deployed at the incident scene 12.

In order for the cascaded location process to precisely locate the packs $22_1 \ldots 22_N$, $26_1 \ldots 26_R$, $24_1 \ldots 24_P$, error propagation through the stages of the process should be minimized. To that end, and as mentioned previously, the location units 40, 140, 240 of the packs $22_1 \ldots 22_N$, $26_1 \ldots 26_R$ $24_1 \ldots 24_P$ and the pack location units $302_1 \ldots 302_9$ of the ECAS outstations $28_1 \ldots 28_M$ may employ wireless technology allowing a location of each of these components to be determined with an excessive level of precision, such as 1 m or less, to permit a build-up of tolerances in a concatenated location approach to maintain an adequate final level of accuracy. For example, in this embodiment, these location units may employ UWB technology (e.g., UWB tags) which offers increased precision, down to tens of centimeters or less. In addition to permitting an expanded range of applications, such as associating a pack with a person near it, or two people together such as one of the first responders $14_1 \ldots 14_N$ and one of the patients $18_1 \ldots 18_P$, the increased accuracy of UWB technology helps to minimize error propagation through the stages of the cascaded location process.

While each of the packs $22_1 \ldots 22_N$, $26_1 \ldots 26_R$ $24_1 \ldots 24_P$ may normally be located when a wireless location signal that it transmits is received by at least three location receivers 303, 43, 143, 243 that are distributed among two or more of the ECAS outstations $28_x$, $28_y$, $28_z$ and other ones of these packs, it may be useful to use four, five, six or even more location receivers, when possible, to determine the location of a given pack. For example, in some embodiment, a location algorithm implemented by the location determination unit 432 may: determine which location receivers 303, 43, 143, 243 are at known locations, i.e., the "located" location receivers; list all the location transmitters 41, 141, 241 of the packs $22_1 \ldots 22_N$, $26_1 \ldots 26_R$ $24_1 \ldots 24_P$ that can be seen by five, four or three of the located location receivers; compute the locations of those packs that can be seen by the maximum number of located location receivers first, which, in this example, is assumed to be five (in other examples, this may be different depending on the number of location receivers at known locations); and once the locations of those packs is established, their location receivers are turned on, themselves becoming "located" location receivers, and their measurements added to the location computation capability. This is then repeated forming a new list of unlocated location transmitters 41, 141, 241 of the packs $22_1 \ldots 22_N$, $26_1 \ldots 26_R$ $24_1 \ldots 24_P$ that can be seen by five, four or three located location receivers and calculating the location of those unlocated location transmitters which can be seen by the maximum number of located location receivers. In cases where less than five located location receivers can see an unlocated location transmitter, the process can be continued at a level of four located location receivers, still allowing the determination of the location of the unlocated location transmitter in 3D, or even with three located location receivers, although this can allow location in 2D. Starting with five (or more) located location receivers rather than just four or three, may help to counter errors which may otherwise be introduced due to various factors, such as a non-deterministic propagation path associated with the wireless location technology used. For instance, using five located location receivers enables five different 3D computations ($Rx_{1,2,3,4}$, $Rx_{1,2,3,5}$, $Rx_{1,2,4,5}$, $Rx_{1,3,4,5}$ and $Rx_{2,3,4,5}$) or ten different 2D computations ($Rx_{1,2,3}$, $Rx_{1,2,4}$, $Rx_{1,2,5}$, $Rx_{1,3,4}$, $Rx_{1,3,5}$, $Rx_{1,4,5}$, $Rx_{2,3,4}$, $Rx_{2,3,5}$, $Rx_{2,4,5}$ and $Rx_{3,4,5}$) to be carried out, allowing detection of potential "outlier" results due to impairments on one path or in one receiver to be detected, whereas using four located location receivers allows a single 3D computation or up to four 2D computations.

With the first responders $14_1 \ldots 14_N$ and the patients $18_1 \ldots 18_P$ being mobile, in some cases running or otherwise moving very rapidly, the location determination unit 432 implemented by the environmental data processing engine 411 of the ECAS 30 may employ fast-tracking interpolative algorithms to keep track of the locations of the first responder packs $22_1 \ldots 22_N$ and the patient packs $24_1 \ldots 24_P$. For example, if a first responder $14_i$ is moving at 8 feet per second (~5 mph), successive location readings on a 250 msec resolution will place him 2 feet from his/her previous location. If 2 feet is larger than an acceptable error for the system, and if his/her first responder pack $22_i$ is being used to locate other packs, it may be necessary to reduce effects of this error. For instance, if a wireless location signal from a remote pack is received at 102.453 ms after the last wireless location signal transmitted by the pack $22_i$, then at 8 feet per second the first responder $14_i$ will have covered 0.811624 ft and so the location computation can take into account that offset.

Although in this embodiment, location computations to determine the locations of the packs $22_1 \ldots 22_N$, $26_1 \ldots 26_R$, $24_1 \ldots 24_P$ are carried out remotely by the ECAS 30, in other embodiments, such location computations may be performed locally by one or more of the ECAS outstations $28_1 \ldots 28_M$. For example, in some embodiments, each of the ECAS outstations $28_1 \ldots 28_M$ may effect location computations to determine the locations of those packs that are located inside its primary coverage area A1 and/or that are located in a region where its secondary coverage area A2 or tertiary coverage area A3 overlaps with the coverage area P of one or more packs from which it receives wireless signals. The ECAS outstations $28_1 \ldots 28_M$ may then collaborate to exchange the locations of the packs that they have individually determined and to determine the locations of those packs that are located in regions where their secondary and tertiary coverage areas A2, A3 overlap. In other embodiments, one of the ECAS outstations $28_1 \ldots 28_M$ may be a "master" outstation to which other ones of these outstations (i.e., "slave" outstations) transmit data derived from wireless signals they receive from packs in order to allow the master outstation to effect the location computations. Location data indicative of the locations of the packs may then be transmitted by each of the ECAS outstations $28_1 \ldots 28_M$ or the master outstation, as the case may be, to the ECAS 30.

More generally, while in embodiments considered above the processing system 20 is distributed between locations that are remote from one another (i.e., distributed between the ECAS outstations $28_1 \ldots 28_M$ at the incident scene 12 and the ECAS 30 located remotely from the incident scene 12), in other embodiments, the processing system 20 may reside entirely in a single location (i.e., its functionality may be implemented entirely by one of the ECAS outstations $28_1 \ldots 28_M$ or the ECAS 30).

Those skilled in the art will appreciate that, in some embodiments, certain functionality of a given component described herein (e.g., the processing entity 50, 150, 250, 360 or 420) may be implemented as pre-programmed hardware or firmware elements (e.g., application specific integrated circuits (ASICs), electrically erasable programmable read-only memories (EEPROMs), etc.) or other related elements. In other embodiments, a given component described herein (e.g., the processing entity 50, 150, 250, 360 or 420) may comprise a general-purpose processor having access to a storage medium that is fixed, tangible, and readable by the general-purpose processor and that stores program code for operation of the general-purpose processor to implement functionality of that given component. The storage medium may store data optically (e.g., an optical disk such as a CD-ROM or a DVD), magnetically (e.g., a hard disk drive, a removable diskette), electrically (e.g., semiconductor memory, including ROM such as EPROM, EEPROM and Flash memory, or RAM), or in any another suitable way. Alternatively, the program code may be stored remotely but transmittable to the given component via a modem or other interface device connected to a network over a transmission medium. The transmission medium may be either a tangible medium (e.g., optical or analog communications lines) or a medium implemented using wireless techniques (e.g., RF, microwave, infrared or other wireless transmission schemes).

Although various embodiments and examples have been presented, this was for the purpose of describing, but not limiting, the invention. Various modifications and enhancements will become apparent to those of ordinary skill in the art and are within the scope of the invention, which is defined by the appended claims.

The invention claimed is:

1. A method for locating a plurality of portable modules at an incident scene, said method comprising:
   receiving first data derived from a wireless signal transmitted by a first one of the portable modules and received by at least three receivers of a plurality of receivers mounted to at least one vehicle transported to the incident scene, at least some of the plurality of receivers disposed on a plurality of extensible arms that are capable of being extended relative to a body of each vehicle;
   determining a location of the first one of the portable modules based on the first data;
   receiving second data derived from a wireless signal transmitted by a second one of the portable modules and received by the first one of the portable modules; and
   determining a location of the second one of the portable modules based on the second data and the location of the first one of the portable modules.

2. A method as claimed in claim 1, wherein the first data comprises data related to times of arrival of the wireless signal transmitted by the first one of the portable modules at the at least three receivers, and the second data comprises data related to a time of arrival of the wireless signal transmitted by the second one of the portable modules at the first one of the portable modules.

3. A method as claimed in claim 2, wherein the wireless signal transmitted by the second one of the portable modules is received by at least one receiver of the plurality of receivers, and the second data comprises data related to a time of arrival of the wireless signal transmitted by the second one of the portable modules at each of the at least one receiver.

4. A method as claimed in claim 2, wherein the wireless signal transmitted by the second one of the portable modules is received by two receivers of the plurality of receivers, and the second data comprises data related to times of arrival of the wireless signal transmitted by the second one of the portable modules at the two receivers.

5. A method as claimed in claim 2, comprising:
   receiving third data related to times of arrival of a wireless signal transmitted by a third one of the portable modules and received by at least three entities amongst the plurality of receivers and the plurality of portable modules; and
   determining a location of the third one of the portable modules based on the third data;

wherein the wireless signal transmitted by the second one of the portable modules is received by one receiver of the plurality of receivers and by the third one of the portable modules, the second data comprises data related to times of arrival of the wireless signal transmitted by the second one of the portable modules at the one receiver and the third one of the portable modules, and said determining the location of the second one of the portable modules comprises determining the location of the second one of the portable modules based on the second data, the location of the first one of the portable modules and the location of the third one of the portable modules.

6. A method as claimed in claim 2, wherein the time of arrival of the wireless signal transmitted by the second one of the portable modules at the first one of the portable modules is measured relative to a time of transmission of the wireless signal transmitted by the first one of the portable modules.

7. A method as claimed in claim 1, comprising:
receiving third data derived from a wireless signal transmitted by a third one of the portable modules and received by the second one of the portable modules; and
determining a location of the third one of the portable modules based on the third data and the location of the second one of the portable modules.

8. A method as claimed in claim 7, wherein the first data comprises data related to times of arrival of the wireless signal transmitted by the first one of the portable modules at the at least three receivers, the second data comprises data related to a time of arrival of the wireless signal transmitted by the second one of the portable modules at the first one of the portable modules, and the third data comprises data related to a time of arrival of the wireless signal transmitted by the third one of the portable modules at the second one of the portable modules.

9. A method as claimed in claim 1, wherein the at least one vehicle comprises a plurality of vehicles and the at least three receivers are distributed amongst at least two of the vehicles.

10. A method as claimed in claim 1, wherein the location of the first one of the portable modules and the location of the second one of the portable modules are determined with a precision of 1 m or better.

11. A method as claimed in claim 1, wherein the wireless signal transmitted by the first one of the portable modules is transmitted by a UWB transmitter of the first one of the portable modules, and the wireless signal transmitted by the second one of the portable modules is transmitted by a UWB transmitter of the second one of the portable modules.

12. A method as claimed in claim 11, wherein the plurality of portable modules comprises at least one portable drop module to be placed at at least one fixed location at the incident scene by the at least one first responder.

13. A method as claimed in claim 1, wherein the plurality of portable modules comprises at least one portable first responder module to be carried by at least one first responder at the incident scene and at least one portable patient module to be associated with at least one patient at the incident scene.

14. A system for locating a plurality of portable modules at an incident scene, said system comprising:
a plurality of receivers, mounted to at least one vehicle, transportable to the incident scene, at least some of the plurality of receivers disposed on a plurality of extensible arms that are capable of being extended relative to a body of each vehicle; and
a processing entity configured to:
determine a location of a first one of the portable modules based on first data derived from a wireless signal transmitted by the first one of the portable modules and received by at least three receivers of the plurality of receivers; and
determine a location of a second one of the portable modules based on the location of the first one of the portable modules and second data derived from a wireless signal transmitted by the second one of the portable modules and received by the first one of the portable modules.

15. A system as claimed in claim 14, wherein the first data comprises data related to times of arrival of the wireless signal transmitted by the first one of the portable modules at the at least three receivers, and the second data comprises data related to a time of arrival of the wireless signal transmitted by the second one of the portable modules at the first one of the portable modules.

16. A system as claimed in claim 15, wherein the wireless signal transmitted by the second one of the portable modules is received by at least one receiver of the plurality of receivers, and the second data comprises data related to a time of arrival of the wireless signal transmitted by the second one of the portable modules at each of the at least one receiver.

17. A system as claimed in claim 15, wherein the wireless signal transmitted by the second one of the portable modules is received by two receivers of the plurality of receivers, and the second data comprises data related to times of arrival of the wireless signal transmitted by the second one of the portable modules at the two receivers.

18. A system as claimed in claim 15, wherein the processing entity is configured to:
determine a location of a third one of the portable modules based on third data related to times of arrival of a wireless signal transmitted by the third one of the portable modules and received by at least three entities amongst the plurality of receivers and the plurality of portable modules;
wherein the wireless signal transmitted by the second one of the portable modules is received by one receiver of the plurality of receivers and by the third one of the portable modules, the second data comprises data related to times of arrival of the wireless signal transmitted by the second one of the portable modules at the one receiver and the third one of the portable modules, and, to determine the location of the second one of the portable modules, said processing entity is configured to determine the location of the second one of the portable modules based on the second data, the location of the first one of the portable modules and the location of the third one of the portable modules.

19. A system as claimed in claim 14, wherein the processing entity is configured to determine a location of a third one of the portable modules based on the location of the second one of the portable modules and third data derived from a wireless signal transmitted by the third one of the portable modules and received by the second one of the portable modules.

20. A system as claimed in claim 19, wherein the first data comprises data related to times of arrival of the wireless signal transmitted by the first one of the portable modules at the at least three receivers, the second data comprises data related to a time of arrival of the wireless signal transmitted by the second one of the portable modules at the first one of the portable modules, and the third data comprises data related to a time of arrival of the wireless signal transmitted by the third one of the portable modules at the second one of the portable modules.

21. A system as claimed in claim 14, wherein the at least one vehicle comprises a plurality of vehicles and the at least three receivers are distributed amongst at least two of the vehicles.

22. A system as claimed in claim 14, wherein the location of the first one of the portable modules and the location of the second one of the portable modules are determined with a precision of 1 m or better.

23. A system as claimed in claim 14, wherein the wireless signal transmitted by the first one of the portable modules is transmitted by a UWB transmitter of the first one of the portable modules, and the wireless signal transmitted by the second one of the portable modules is transmitted by a UWB transmitter of the second one of the portable modules.

24. A system as claimed in claim 14, wherein the plurality of portable modules comprises at least one portable first responder module to be carried by at least one first responder at the incident scene and at least one portable patient module to be associated with at least one patient at the incident scene.

25. A system as claimed in claim 24, wherein the plurality of portable modules comprises at least one portable drop module to be placed at at least one fixed location at the incident scene by the at least one first responder.

26. Computer-readable media containing computer-readable program code executable by a computing apparatus to implement a process for locating a plurality of portable modules at an incident scene, said computer-readable program code comprising:
  first program code for causing the computing apparatus to be attentive to receipt of first data derived from a wireless signal transmitted by a first one of the portable modules and received by at least three receivers of a plurality of receivers mounted to at least one vehicle transported to the incident scene, at least some of the plurality of receivers disposed on a plurality of extensible arms that are capable of being extended relative to a body of each vehicle;
  second program code for causing the computing apparatus to determine a location of the first one of the portable modules based on the first data;
  third program code for causing the computing apparatus to be attentive to receipt of second data derived from a wireless signal transmitted by a second one of the portable modules and received by the first one of the portable modules; and
  fourth program code for causing the computing apparatus to determine a location of the second one of the portable modules based on the second data and the location of the first one of the portable modules.

* * * * *